United States Patent [19]

DiNinno et al.

[11] Patent Number: 5,532,261

[45] Date of Patent: Jul. 2, 1996

[54] CARBAPENEM ANTIBIOTICS, COMPOSITIONS CONTAINING SUCH COMPOUNDS AND METHODS OF USE

[75] Inventors: Frank P. DiNinno, Old Bridge; Ravindra N. Guthikonda, Edison; Laura C. Meurer, Scotch Plains, all of N.J.

[73] Assignee: Merck & Co., Inc., Rahway, N.J.

[21] Appl. No.: 353,868

[22] Filed: Dec. 12, 1994

[51] Int. Cl.$^6$ .......................... C07D 487/04; A61K 31/40
[52] U.S. Cl. .............................. 514/210; 540/302
[58] Field of Search ............................. 514/210; 540/302

[56] References Cited

U.S. PATENT DOCUMENTS

| | | |
|---|---|---|
| 4,962,101 | 10/1990 | DiNinno et al. . |
| 5,004,739 | 4/1991 | DiNinno et al. . |
| 5,004,740 | 4/1991 | DiNinno et al. . |
| 5,006,519 | 4/1991 | DiNinno et al. . |
| 5,025,006 | 6/1991 | DiNinno et al. . |
| 5,025,007 | 6/1991 | Greenlee et al. . |
| 5,025,008 | 6/1991 | DiNinno et al. . |
| 5,034,384 | 7/1991 | Greenlee et al. . |
| 5,034,385 | 7/1991 | DiNinno et al. . |
| 5,037,820 | 8/1991 | DiNinno et al. . |
| 5,128,335 | 7/1992 | Guthikonda et al. . |
| 5,144,028 | 9/1992 | Greenlee et al. . |
| 5,153,185 | 10/1992 | DiNinno et al. . |
| 5,153,186 | 10/1992 | DiNinno et al. . |
| 5,157,033 | 10/1992 | DiNinno et al. . |
| 5,162,314 | 11/1992 | DiNinno et al. . |
| 5,177,202 | 1/1993 | DiNinno et al. . |
| 5,182,384 | 1/1993 | DiNinno et al. . |
| 5,196,529 | 3/1993 | DiNinno et al. . |
| 5,216,146 | 6/1993 | DiNinno et al. . |
| 5,240,920 | 8/1993 | DiNinno et al. . |
| 5,247,074 | 9/1993 | DiNinno et al. . |
| 5,294,610 | 3/1994 | DiNinno et al. . |
| 5,328,904 | 7/1994 | DiNinno et al. . |
| 5,336,674 | 8/1994 | DiNinno et al. . |
| 5,342,933 | 8/1994 | DiNinno et al. . |
| 5,362,723 | 11/1994 | DiNinno et al. . |

*Primary Examiner*—Rebecca Cook
*Attorney, Agent, or Firm*—Richard C. Billups; Mark R. Daniel

[57] ABSTRACT

Compounds are disclosed represented by the formula:

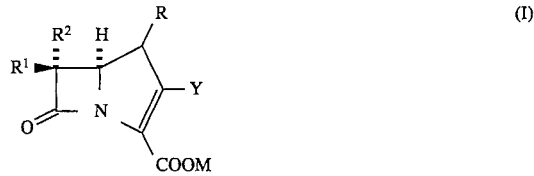

wherein Y is:

a)

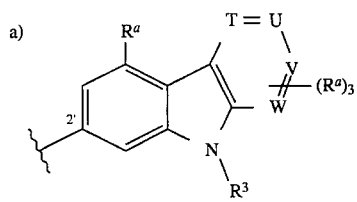

or b)

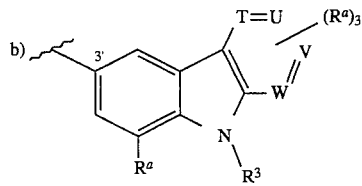

or a pharmaceutically acceptable salt or ester thereof.

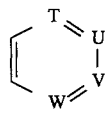

represents an aromatic 6 membered ring; zero or one of T, U, V and W represents $N^+R^y$ and the remainder of T, U, V and W are independently selected from C and N, such that one of T, U, V and W represents $N^+R^y$ or N.

Pharmaceutical compositions and methods of use are also included.

24 Claims, No Drawings

CARBAPENEM ANTIBIOTICS, COMPOSITIONS CONTAINING SUCH COMPOUNDS AND METHODS OF USE

BACKGROUND OF THE INVENTION

The present invention relates to carbapenem antibiotics, which are substituted in the 2-position with a carbolinyl derivative.

Thienamycin was an early carbapenem antibacterial agent having a broad spectrum; it has the following formula:

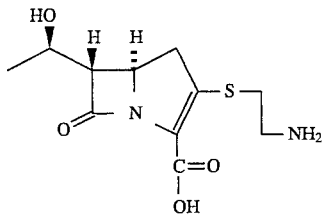

Later, N-formimidoyl thienamycin was discovered; it has the formula:

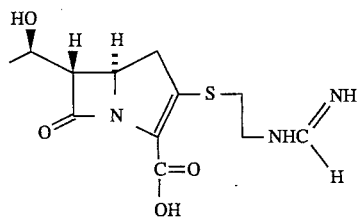

U.S. Pat. Nos. 5,011,832 and 5,025,006 relate to carbapenems of the structure shown below which exhibit antimicrobial activity against strains of methicillin resistant staphylococci (MRSA). The carbapenems described therein possess a meta-disposed biphenyl moiety attached to the C-2 position of the carbapenem ring.

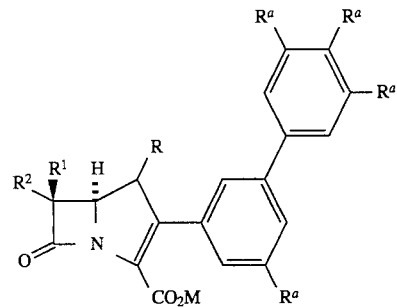

More recently, U.S. Pat. No. 5,034,384 issued to Greenlee, et al. and EPA 472 306 published on Feb. 26, 1992 addressing compounds of the formula:

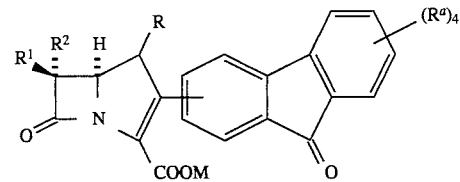

Such compounds have MRSA and MRCNS activity.

U.S. Pat. No. 5,128,335 issued to DiNinno, et al. on Jul. 7, 1992 addressing compounds of the formula:

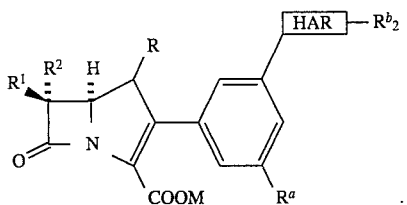

U.S. Pat. No. 5,294,610 issued to DiNinno, et al. on Mar. 15, 1994 addressing compounds of the formula:

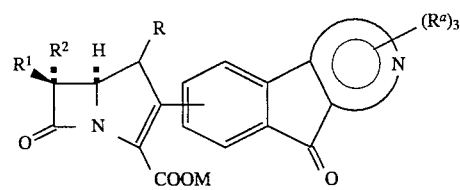

The carbolinyl carbapenems of the present invention are particularly useful in treating infections caused by gram positive organisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. There is an increasing need for agents effective against such pathogens (MRSA/MRCNS). In addition, certain members of the class have been found to possess a broader spectrum of activity which includes gram negative bacteria.

SUMMARY OF THE INVENTION

The present invention provides carbapenem compounds represented by the formula:

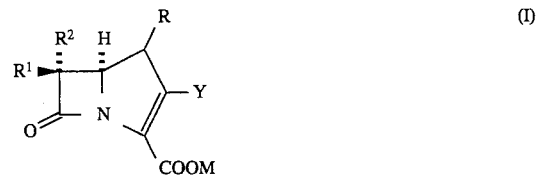

(I)

or a pharmaceutically acceptable salt thereof, wherein:

Y is:

a) 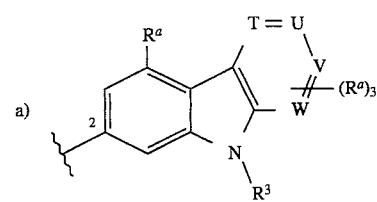

or b) 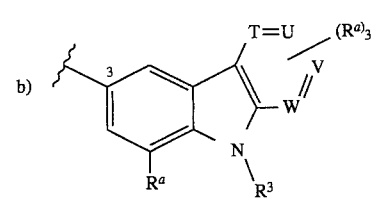

R and R³ represent H or CH₃;

R¹ and R² are independently H, CH₃—, CH₃CH₂—, —(CH₃)₂CH—, HOCH₂—, CH₃CH(OH)—, (CH₃)₂C(OH), FCH₂CH(OH)—, F₂CHCH(OH)—, F₃CCH(OH)—, CH₃CH(F)—, CH₃CF₂—, or (CH₃)₂C(F)—;

M is selected from:
i) hydrogen;
ii) a pharmaceutically acceptable esterifying group or removable carboxyl protecting group, or
iii) a negative charge which is balanced by a positively charged group;

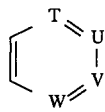

represents an aromatic 6 membered ring;

one of T, U, V and W represents $N^+R^y$ or N, and the others represent C;

$R^y$ is selected from the group consisting of: —H, —O⁻, —C₁₋₄alkyl, —OC₁₋₄alkyl, —NH₂, —NHC₁₋₄alkyl, —N(C₁₋₄alkyl)₂, —C₁₋₄ alkyl(R^q)₁₋₃, —OC₁₋₄alkyl(R^q)₁₋₃, —NHC₁₋₄ alkyl(R^q)₁₋₃ and —N[C₁₋₄alkyl(R^q)₁₋₃]₂ wherein Rq is as defined below;

four $R^a$ groups are present, each independently selected from the group consisting of hydrogen, Type I and Type II set forth below, provided that 0–1 $R^a$ groups are selected from Type I and the remaining $R^a$ groups are selected from H and Type II;

Type I substituents are selected from the group consisting of:

(a) 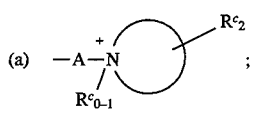

wherein A is $(CH_2)_m$—Q—$(CH_2)_n$, in which m is 0–6, n is 1–6 and Q is selected from the group consisting of: a covalent bond, —O—, —S—, —SO—, —SO₂—, —NH—, —SO₂NH—, —NHSO₂—, —CONH—, —NHCO—, —SO₂N(C₁₋₄alkyl)—, —N(C₁₋₄alkyl)SO₂—, —CON(C₁₋₄alkyl)—, —N(C₁₋₄alkyl)CO—, —CH=CH—, —CO—, —OC(O)—, —C(O)O— and —N(C₁₋₄ alkyl);

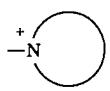

is a 5- or 6-membered monocyclic heterocycle or an 8-, 9- or 10-membered bicyclic heterocycle, said heterocycle containing a first nitrogen in an aromatic 5- or 6-membered first ring, with attachment of the heterocycle to A by way of said first nitrogen, said first nitrogen being tertiary or quaternary, with the first ring containing 0–1 of either O or S, with the first ring containing 0–3 additional nitrogen atoms, with the first ring optionally fused to a 3- or 4-membered moiety to form an optional second ring, with the moiety containing at least one carbon atom, with the moiety containing 0–1 of either O or S, with the moiety containing 0–2 nitrogen atoms, and with the moiety being saturated or unsaturated and the second ring being aromatic or non-aromatic;

each $R^c$ independently represents H or $R^a$ as defined below under Type II;

(b) 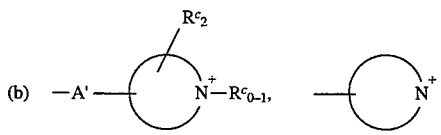

is a 5- or 6-membered monocyclic heterocycle or an 8-, 9- or 10-membered bicyclic heterocycle, the heterocycle containing a first nitrogen in an aromatic 5- or 6-membered first ring, 0–1 of either O or S, and 0–2 additional nitrogen atoms, said first nitrogen being quaternary, with the first ring optionally fused to a 3- or 4-membered moiety to form an optional second ring which is aromatic or non-aromatic, said moiety containing at least one carbon atom, 0–1 of O or S, and 0–2 additional nitrogen atoms, said moiety being saturated or unsaturated;

$R^c$ is as defined above;

A' represents $(CH_2)_m$—Q—$(CH_2)_{n'}$, where m is as defined above and n' independently represents 0–6;

Q is as defined above except that when m and n' are both 0, Q is not a covalent bond;

where $R^x$ and $R^z$ are as defined under Type II below, or $R^x$ and $R^z$ together represent a $C_{2-4}$ alkylidene radical which forms a ring (optionally substituted with 1–3 groups selected from $R^q$ as defined below) optionally interrupted by $N(O)R^e$ or $N^+(R^e)_2$ (where $R^e$ is hydrogen, $C_{1-4}$ alkyl, or $C_{1-4}$ alkyl substituted with 1–3 groups selected from $R^q$ as defined below), when present, $R^y$ is as defined above;

or $R^x$, $R^y$ and $R^z$ are taken together and represent a $C_{5-10}$ tertiary alkylidene radical which with $N^+$ forms a bicyclic ring, said tertiary alkylidene radical being optionally substituted with 1–3 groups selected from Rq as defined below, and the tertiary carbon of the tertiary alkylidene radical is optionally replaced with a member selected from the group consisting of: N, $N^+$—$R^e$ (where $R^e$ is as previously defined) and $N^+$—$O^-$;

A is as defined above, and p is 0 or 1;

(d) 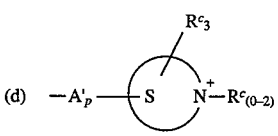

where

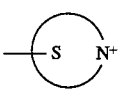

represents a 4-, 5- or 6-membered monocyclic heterocycle or an 8-, 9- or 10-membered bicyclic heterocycle, said heterocycle containing a first nitrogen in a first ring, with the fast ring being non-aromatic and either saturated or unsaturated, said first nitrogen being a quaternary nitrogen, said first ring containing in addition to carbon and the first nitrogen, 0 or 1 member selected from the group consisting of N, O, S, S(O), S(O)$_2$ and NR$^e$, where R$^e$ is as defined above, said first non-aromatic ring being optionally fused to a 2-, 3- or 4-membered moiety to form an optional second ring;

A' is defined above;
p is defined above; and
R$^q$ is defined below;
and

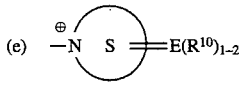

wherein
E represents C, N or N$^+$ attached to the ring by a double bond;

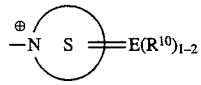

represents a 4-, 5- or 6-membered monocyclic heterocycle, either saturated or unsaturated, said fast nitrogen being a quaternary nitrogen, said ring containing in addition to carbon and the fast nitrogen, 0 or 1 member selected from the group consisting of N, O, S, S(O), S(O)$_2$ and NR$^e$, where R$^e$ is as defined above;

R$^{10}$ represents H, C$_{1-4}$ alkyl or C$_{1-4}$ alkyl substituted with from 1–3 R$^q$ groups, with R$^q$ as defined below;

and wherein the Type 1I substituents are selected from the group consisting of:

a) —CF$_3$;
b) a halogen atom selected from the group consisting of: —Br, —Cl, —F and —I;
c) —OC$_{1-4}$ alkyl, wherein the alkyl is optionally substituted with 1–3 groups selected from R$^q$, wherein R$^q$ represents a member selected from the group consisting of: —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

d) —OH;
e) —O(C=O)R$^s$, where R$^s$ is C$_{1-4}$ alkyl or phenyl, each of which is optionally substituted by 1–3 R$^q$ groups as defined above;
f) —O(C=O)N(R$^x$)R$^z$, where R$^x$ and R$^z$ are independently H, C$_{1-4}$ alkyl (optionally substituted by 1–3 R$^q$ groups as defined above), together a 3- to 5-membered alkylidene radical to form a ring (optionally substituted with 1–3 R$^q$ groups as defined above) or together a 2- to 4-membered alkylidene radical, interrupted by —O—, —S—, —S(O)— or —S(O)$_2$— to form a ring (where the ring is optionally substituted with 1–3 R$^q$ groups as defined above);

g) —S(O)$_q$—R$^s$ where q=0–2, and R$^s$ is defined above;
h) —SO$_2$N(R$^x$)R$^z$ where R$^x$ and R$^z$ are as defined above;
i) —N$_3$;
j) —N(R$^t$)(C=O)H, where R$^t$ is H or C$_{1-4}$ alkyl, and the C$_{1-4}$ alkyl portion thereof is optionally substituted with 1–3 R$^q$ groups, wherein R$^q$ is as defined above;
k) —N(R$^t$)(C=O)C$_{1-4}$ alkyl, wherein R$^t$ is as defined above, and the alkyl group is optionally substituted by 1–3 R$^q$ groups, with R$^q$ as defined above;
l) —N(R$^t$)(C=O)OC$_{1-4}$ alkyl, wherein R$^t$ is as defined above,
and the alkyl portion thereof is optionally substituted with 1–3 R$^q$ groups, with R$^q$ as defined above;
m) —N(R$^t$)(C=O)N(R$^y$)R$^z$ wherein R$^t$, R$^y$ and R$^z$ are as defined above;
n) —N(R$^t$)SO$_2$R$^s$, wherein R$^s$ and R$^t$ are as defined above;
o) —CN;
p) —(C=O)H or —CH(OCH$_3$)$_2$;
q) —C(OCH$_3$)$_2$C$_{1-4}$ alkyl, wherein the alkyl portion thereof is optionally substituted with 1–3 R$^q$ groups, with R$^q$ as defined above;
r) —(C=O)R$^s$, wherein R$^s$ is as defined above;
s) —(C=NOR$^z$)R$^y$ wherein R$^y$ and R$^z$ are as defined above, except they may not be joined together to form a ring;
t) —(C=O)OC$_{1-4}$ alkyl, wherein the alkyl portion thereof is optionally substituted with 1–3 R$^q$ groups, with R$^q$ as defined above;
u) —(C=O)N(R$^y$)R$^z$ wherein R$^y$ and R$^z$ are as defined above;
v) —(C=O)—N(OR$^y$)R$^z$ wherein R$^y$ and R$^z$ are as defined above, except they may not be joined together to form a ring;
w) —(C=S)N(R$^y$)R$^z$ wherein R$^y$ and R$^z$ are as defined above;
x) —COOM$^b$, wherein M$^b$ is as defined above;
y) —SCN;
z) —SCF$_3$;
aa) tetrazolyl, where the point of attachment is the carbon atom of the tetrazole ring and one of the nitrogen atoms is mono-substituted by hydrogen, an alkali metal or a C$_1$–C$_4$ alkyl optionally substituted by R$^q$ as defined above;
ab) an anionic function selected from the group consisting of: phosphono: [P=O(OM$^b$)$_2$]; alkylphosphono: {P=O(OM$^b$)-[O(C$_1$–C$_4$ alkyl)]}; alkylphosphinyl: [P=O(OM$^b$)—(C$_1$–C$_4$-alkyl)]; phosphoramido: [P=O(OM$^b$)N(R$^y$)R$^z$ and P=O(OM$^b$)NHR$^w$]; sulfino: (SO$_2$M$^b$); sulfo: (SO$_3$M$^b$); acylsulfonamides selected from the structures: CONM$^b$SO$_2$R$^w$, CONM$^b$SO$_2$N(R$^y$)R$^z$, SO$_2$NM$^b$CON(R$^y$)R$^z$; and SO$_2$NM$^b$CN, where R$^w$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which form 1 to 2 additional carbon atoms are optionally replaced by a nitrogen heteroatom, and where the phenyl and heteroaryl are optionally substituted with 1–3 R$^q$ groups, wherein R$^q$ is as defined above; M$^b$ is as defined above; and R$^y$ and R$^z$ are as defined above;

ac) $C_5$–$C_7$ cycloalkyl group in which one of the carbon atoms in the ring is replaced by a heteroatom selected from O, S, NH, or N($C_1$–$C_4$ alkyl) and in which one additional carbon may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$–$C_4$ alkenyl radical, optionally substituted with 1–3 substituents a) to ac) above and phenyl which is optionally substituted by 1–3 $R^q$ groups, with $R^q$ as defined above;

ae) $C_2$–$C_4$ alkynyl radical, optionally substituted by one to three of the substituents a) to ac) above;

af) $C_1$–$C_4$ alkyl radical;

ag) $C_1$–$C_4$ alkyl substituted with 1–3 of the substituents a)–ac) above;

ah) a 2-oxazolidinonyl moiety in which the point of attachment is the nitrogen atom of the oxazolidinone ring, the ring oxygen atom is optionally replaced by a heteroatom selected from S and $NR^t$ (where $R^t$ is as defined above) and one of the saturated carbon atoms of the oxazolidinone ring is optionally monosubstituted by one of the substituents a) to ag) above.

DETAILED DESCRIPTION

The invention is described herein in detail using the terms defined below unless otherwise specified.

When a group is termed "substituted", unless otherwise indicated, this means that the group contains from 1 to 3 substituents $R^q$ thereon.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. Alkyl as used herein also includes substituted alkyl groups. When substituted, alkyl groups may be substituted with up to three substituent groups, $R^q$, at any available point of attachment. When the alkyl group is said to be substituted with an alkyl group, this can be used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical, straight, branched or cyclic, containing from 2 to 10 carbon atoms and at least one carbon to carbon double bond. Alkenyl includes substituted alkenyl groups. Preferred alkenyl groups include ethenyl, propenyl, butenyl and cyclohexenyl.

The term "alkynyl" refers to a hydrocarbon radical straight, branched or cyclic, containing from 2 to 10 carbon atoms and at least one carbon to carbon triple bond. Alkynyl includes substituted alkynyl groups. Preferred alkynyl groups include ethynyl, propynyl and butynyl.

Aryl refers to aromatic rings e.g., phenyl, substituted phenyl and the like, groups as well as rings which are fused, e.g., naphthyl, phenanthrenyl and the like. Aryl groups thus contain at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl includes substituted aryl groups.

The term "heteroaryl" is a specie of aryl and of heterocyclyl, referring to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to four $R^q$ groups.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyridine, pyrimidine and pyrazine and triazine.

The heterocyclic group of $R^x$ may optionally be substituted with 1–3 groups selected from $R^q$.

The term "heterocycloalkyl" refers to a cycloalkyl group (nonaromatic) in which one of the carbon atoms in the ring is replaced by a heteroatom selected from O, S, NH, or N($C_1$–$C_4$ alkyl), and in which up to three additional carbon atoms may be replaced by said hetero groups. Heterocycloalkyl includes substituted heterocycloalkyl groups.

The term "quaternary nitrogen" refers to a tetravalent positively charged nitrogen atom including, e.g., the positively charged nitrogen in a tetraalkylammonium group (e.g., tetramethylammonium, N-methylpyridinium), the positively charged nitrogen in a protonated ammonium species (e.g., trimethylhydroammonium, N-hydropyridinium), the positively charged nitrogen in an amine N-oxide (e.g., N-methylmorpholine-N-oxide, pyridine-N-oxide), and the positively charged nitrogen in an N-amino-ammonium-N-oxide), group (e.g., N-aminopyridinium).

The term "heteroatom" means O, S or N, selected on an independent basis.

Alkylene (alkylidene or alkanediyl) and arylene refer to the groups noted above, with two points of attachment, for example, at any of the 1, 1-1, 2-, 1, 3- or 1, 4-positions. Alkylene and arylene include substituted alkylene and substituted arylene groups, respectively.

Examples of alkylene include —$CH_2$—, —$CH_2CH_2$—, —$CH_2CH_2CH_2$—,

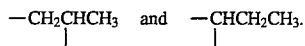

Similarly, alkanetriyl refers to an alkane-derived group with three points of attachment. Alkanetriyl groups contain from five to fifteen carbon atoms, which may be straight, branched, cyclic or multicyclic.

Aralkyl is a specie of substituted alkyl, containing up to three aryl groups substituted on a straight, branched or cycloalkyl group. The most preferred aralkyl group is benzyl.

Halogen, and "halo" refer to bromine, chlorine, fluorine and iodine.

Alkoxy refers to $C_1$–$C_4$ alkyl —O—, with the alkyl portion thereof optionally substituted with 1–3 $R^q$ groups.

Carbonyloxy refers to the radical: —OC(O)$R^s$, where $R^s$ is $C_{1-4}$ alkyl or phenyl, each of which is optionally substituted with 1–3 $R^q$ groups.

Carbamoyloxy refers to the radical: —OC(O)N($R^y$)$R^z$, where $R^y$ and $R^z$ are independently H, $C_{1-4}$ alkyl, (optionally substituted with 1–3 $R^q$ groups as defined above). Alternatively, $R^y$ and $R^z$ can be taken together to represent a 3- to 5-membered alkylidene radical which forms a ring (optionally substituted with 1–3 $R^q$ groups as defined above), or a 2- to 4-membered alkylidene radical interrupted by —O—, —S—, —S(O)— or —S(O)$_2$— which forms a ring, said ring being optionally substituted with 1–3 $R^q$ groups as defined above.

The term "sulfur radical" refers to the group: —S(O)$_q$—$R^s$, where q is an integer of from 0 to 2, and $R^s$ is as defined above.

The term "sulfamoyl group" refers to: —SO$_2$N($R^y$)$R^z$, where $R^y$ and $R^z$ are as defined above.

The term "azido" refers to the group: N$_3$.

The term "formamido" refers to the group: —N($R^t$)C(O)H, where $R^t$ is H or $C_{1-4}$ alkyl, the alkyl portion thereof being optionally substituted with 1–3 $R^q$ groups.

The term "alkylcarbonylamino" refers to the group: —N($R^t$)C(O)$^C_{1-4}$ alkyl, the alkyl portion thereof being optionally substituted with 1–3 $R^q$ groups.

The term "alkoxycarbonylamino" refers to the group: —N($R^t$)C(O)OC$_{1-4}$ alkyl, the alkyl portion thereof being optionally substituted with 1–3 $R^q$ groups.

The term "ureido" refers to the group: —N($R^t$)C(O)N($R^y$)$R^z$.

The term "sulfonamido" refers to the group: —N($R^t$)SO$_2$$R^s$.

The terms "formyl" and "acetalized formyl radical" refer to the groups: —C(O)H or —CH(OCH$_3$)$_2$, respectively. Thus, an alkylcarbonyl radical wherein the carbonyl is acetalized is of the formula: —C(OCH$_3$)$_2$ $C_1$–$C_4$ alkyl, where the alkyl is optionally substituted by 1–3 $R^q$ groups.

A "carbonyl radical" is represented by the formula: —C(O)$R^s$.

A "hydroxyiminomethyl" radical in which the oxygen or carbon atom is optionally substituted by a $C_1$–$C_4$ alkyl group is represented by the formula: —(C=NO$R^z$)$R^y$ where $R^y$ and $R^z$ are as defined above, except they may not be joined together to form a ring.

An "alkoxycarbonyl" radical is represented by the formula: —C(O)OC$_{1-4}$ alkyl, where the alkyl is optionally substituted by 1–3 $R^q$ groups.

A "carbamoyl" radical is represented by the formula: —C(O)N($R^y$)$R^z$, where $R^y$ and $R^z$ are as defined.

An N-hydroxycarbamoyl or N($C_1$–$C_4$ alkoxy)carbamoyl radical in which the nitrogen atom may be additionally substituted by a $C_1$–$C_4$ alkyl group is represented by the formula: —C(O)N(O$R^y$)$R^z$, where $R^y$ and $R^z$ are as defined above, except they may not be joined together to form a ring.

A "thiocarbamoyl group" is represented by the structural formula: —C(S)N($R^y$)$R^z$.

A "carboxyl group" is represented by the structural formula: —COO$M^a$ where $M^a$ is as defined above.

The term "tetrazolyl" is a heteroaryl group where the point of attachment is the carbon atom of the tetrazole ring and one of the nitrogen atoms is optionally mono-substituted by an alkali metal or a $C_1$–$C_4$ alkyl optionally substituted by 1–3 $R^q$ groups.

The term "anionic function" refers to the members of the group: phosphono [P=O(O$M^a$)$_2$]; alkylphosphono {P=O(O$M^a$)-[O($C_1$-$C_4$ alkyl)]}; alkylphosphinyl [P=O(O$M^a$)—($C_1$-$C_4$alkyl)]; phosphoramido [P=O(O$M^a$)N($R^y$)$R^z$ and P=O(O$M^a$)NH$R^w$]; sulfino (SO$_2$$M^a$); sulfo (SO$_3$$M^a$); acylsulfonamides selected from: SO$_2$N$M^a$CON($R^y$)$R^z$; and SO$_2$N$M^a$CN, where $R^w$ is phenyl or heteroaryl.

The term "alkali metal cation" refers to positively charged forms of the alkaline earth metals which comprise Group Ia of the periodic table of elements. Examples include sodium and potassium. These charged elemental forms are often in combination with the carboxylate anion, COO—. For example, when necessary to maintain charge balance, such as in many of the intermediates and in the non-quaternary compounds of the invention, the carboxylate anion is in association with an alkali metal cation.

The present invention also provides novel intermediate carbapenem compounds of the formula:

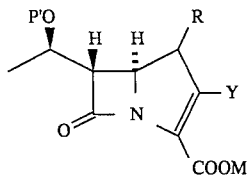

wherein:

Y is as defined above with the following exceptions:
(1) in the Type I definition (c), $R^q$ additionally includes —OP', where P' is as defined below, and $M^a$ and $M^b$ additionally include M, where M is as defined above;
(2) the Type I definition (d) additionally includes a protected hydroxy group, —OP', where P' is as defined below; and the Type I, $R^a$ substituent is optionally balanced with the anionic form of Z, where:

Z is methanesulfonyloxy, trifluoromethane-sulfonyloxy, fluorosulfonyloxy, p-toluenesulfonyloxy, 2,4,6-triisopropyl-benzenesulfonyloxy, p-bromobenzenesulfonyloxy, p-nitro-benzenesulfonyloxy, chloro, bromo or iodo; and P' is a removable hydroxyl protecting group such as trialkylsilyl, aryl(alkyl)alkoxysilyl, alkyldiarylsilyl, alkoxydiarylsilyl, aryldialkylsilyl, alkyloxycarbonyl, substituted alkyloxycarbonyl, benzyloxy-carbonyl, substituted benzyloxycarbonyl, allyloxycarbonyl, or substituted allyloxycarbonyl.

All other substituents are as defined above.

The values of Type I $R^a$ (a) through (e) shown above can be charged or uncharged. The positive charge has been drawn in groups (a) through (e). The positive charge nitrogen-containing group is drawn as having four points of attachment, such as by attachment to the A moiety, ring bonds, $R^c$ group or groups, $R^{10}$, $R^x$, $R^y$ or $R^z$, the nitrogen is considered quaternary and positively charged. When the nitrogen has only three points of attachment, the nitrogen is tertiary and uncharged. Tertiary nitrogen containing groups can be quaternized by standard procedures, such as the Menshutkin reaction. Both charged and uncharged nitrogen-containing compounds are included in the invention.

When the Type I $R^a$ variable(s) contains the group

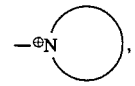

the spacer moiety —A— forms an alkylene chain, optionally interrupted with a heteroatom or functional group, —Q—.

The heterocyclic group

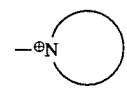

may optionally contain up to three additional nitrogen atoms and up to one oxygen or sulfur atom.

When the Type I $R^a$ variable(s) contains

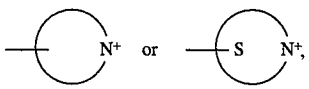

the spacer moiety —A'— is present. The ring structure is bonded to —A'— through an atom other than a ring nitrogen. The heterocycle can be aromatic, partially aromatic or non-aromatic. The ring nitrogen is optionally substituted with one or two groups $R^c$, as desired. When two $R^c$ groups are present on the ring nitrogen which is shown, and the structure is non-aromatic, the nitrogen is positively charged. Also, when the ring is aromatic and one $R^c$ is present on the ring nitrogen, the nitrogen is positively charged. Hence, the nitrogen may have up to two $R^c$ groups present thereon, depending on the particular configuration desired.

Up to three $R^c$ groups may be substituted onto the ring at any available point of attachment.

When the variables and substituent groups are shown with bonds attached, e.g., —A—, —$R^c$, etc., this is to serve as a point of reference for application to the generic structure, and does not indicate that double or triple bonds are intended.

When one of the $R^a$ variables represents group:

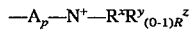   c)

the spacer moiety —A— represents an optional alkylene group, which in turn is optionally interrupted with Q, which may be a heteroatom, substituted amine, sulfonamide or the like. The nitrogen bound to the —A— spacer moiety is either uncharged, such as when $R^y$ is absent, or quaternary by virtue of the $R^x$, $R^y$ and $R^z$ groups present thereon and —A— attached thereto.

Alternatively, $R^x$, $R^y$ and $R^z$ may be taken together to represent a $C_4$ to $C_{10}$ alkanetriyl group, bonded to the nitrogen which is shown. Thus, the nitrogen is quaternary.

When one of the $R^a$ groups represents

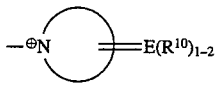   (e)

the nitrogen containing ring

is as defined for Type I(a) except that it is not aromatic. The ring can be saturated or unsaturated. E is attached to the ring by a double bond, and 1–2 $R^{10}$ groups are attached to E. When E represents a carbon atom, two $R^{10}$ groups are present. When E represents N, the N is double bonded to the ring, and one R 10 group is present. When E represents $N^+$, there are two $R^{10}$ groups attached to it.

The bond at position one of the carbapenem nucleus is shown as a wavy line in many of the structures contained herein. This indicates that the configuration of the carbon atom at position one in the carbapenem is alpha or beta, or a mixture of isomers is intended. The preferred configuration is beta.

In the compounds of the present invention, the $R^a$ substituent may contribute to the anti-MSRA/MRCNS activity of the overall molecule, or to the other properties of the molecule.

Some $R^a$ substituents may be distinguishable from others chemically or with respect to the biological properties which they confer. In related compounds, it has been found that the charged compounds may afford greater water solubility and reduced potential for CNS side effects. Substituents which tend to confer improved water solubility on the overall compound have been found useful, since they are contemplated to improve the pharmacokinetics of the compound involved. Although a substantial number and range of $R^a$ substituents has been described herein, all of these are contemplated to be a part of the present invention in connection with the genus of formula I.

In one preferred group of compounds, the nitrogen atom in T, U, V or W is positively charged.

One subgenus of the compounds of the present invention, wherein W is positively charged, is represented by formula Ia:

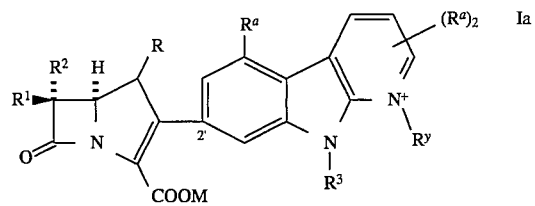

Another subgenus of compounds, wherein W is positively charged, is represented by formula Ib:

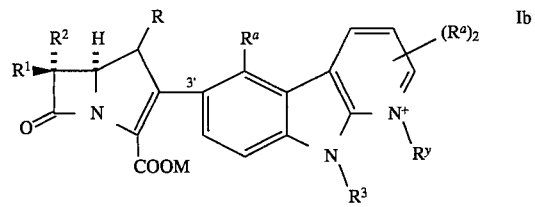

Examples where W represents $N^+R^y$ include the following:

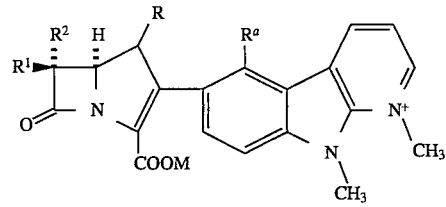

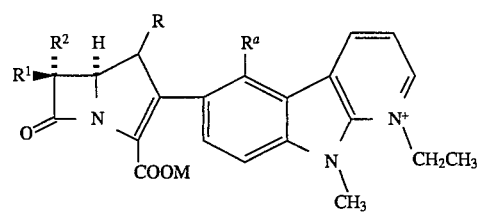

Examples in which W represents N include the following:

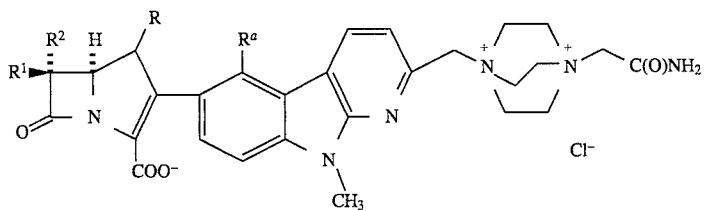

Another subgenus of the compounds of the present invention wherein V is positively charger is represented by formula Ic:

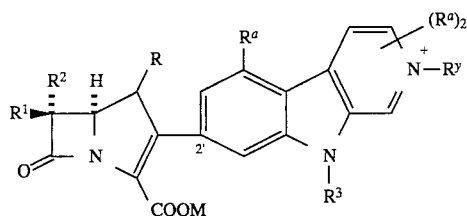

Another subgenus of compounds of the invention wherein V is positively charged is represented by formula Id:

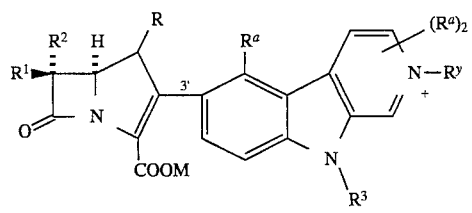

Examples in which V represents N⁺R$^y$ include the following:

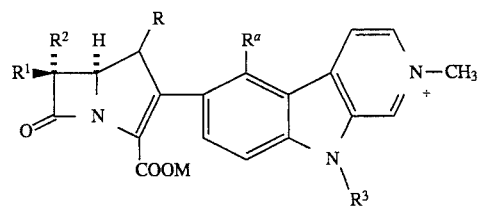

$R^3$ = H or CH₃

The preferred compounds of the invention include compounds wherein $R^1$ and $R^2$ include H and substituted lower alkyl, respectively. Preferred substituent groups include F and hydroxy. Particularly preferred are compounds where one of $R^1$ and $R^2$ is H, and the other is 1-hydroxyethyl.

In the preferred compounds of Formula I, $R^1$ is hydrogen; $R^2$ is (R) CH₃CH(OH)— or (R) CH₃CH(F)—. The designation (R) defines the absolute configuration of the stereocenter.

In the most preferred cases, $R^1$ is hydrogen and $R^2$ is (R) CH₃CH(OH)—.

The substituent R=CH₃ may be of either configuration, i.e., the α or β-stereoisomer, preferably the β-stereoisomer. Additionally, in preferred compounds of Formula I, in total, up to two $R^a$ substituents are other than hydrogen.

When Y is (b), the 3'-carbolinyl substituent is preferably of the configuration:

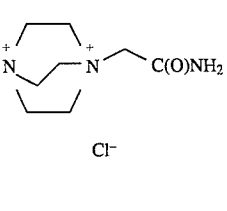

Preferred Type Ia substituents include:

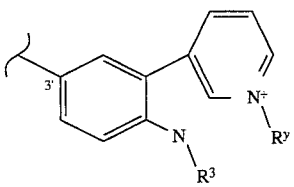

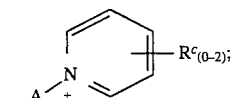

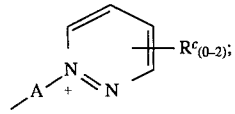

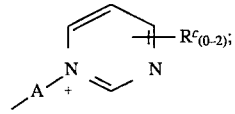

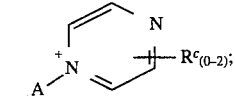

where the ring contains three carbon atoms;

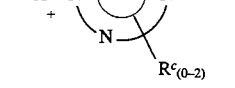

where the ring contains two carbon atoms;

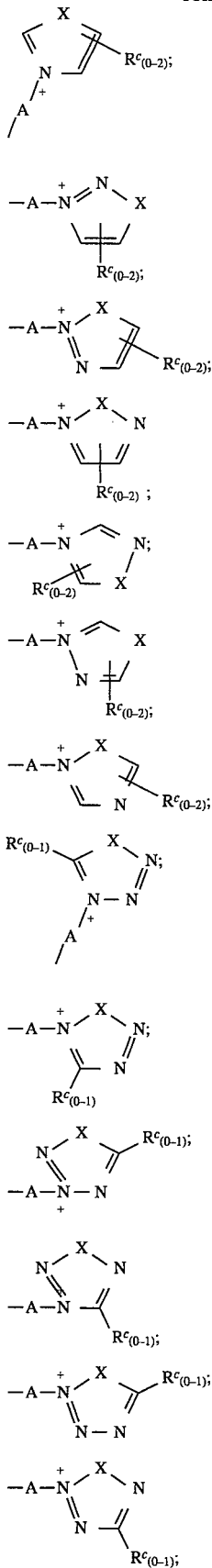
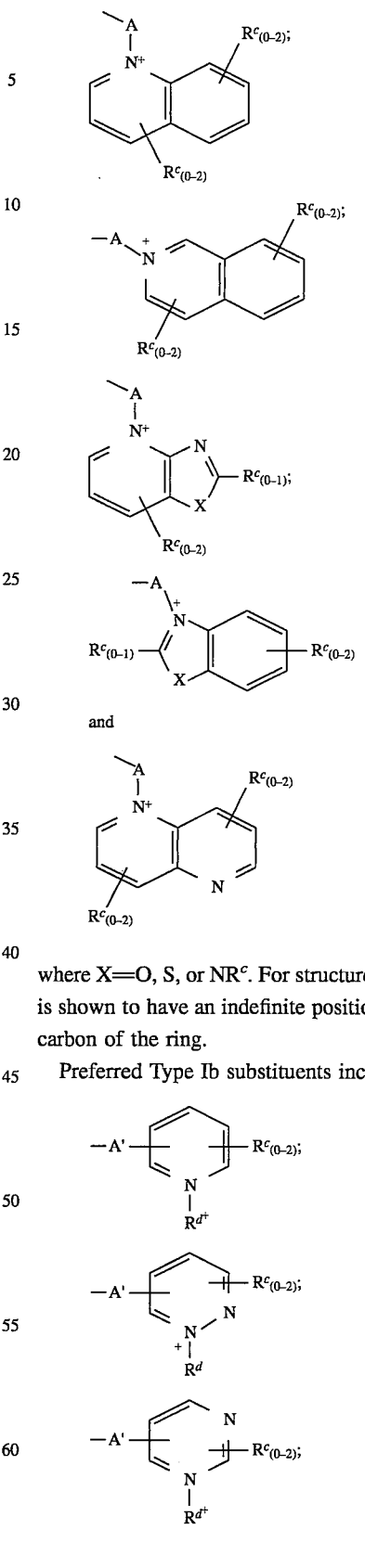
where X=O, S, or NR$^c$. For structures of Type Ia, where R$^c$ is shown to have an indefinite position, it is attached to any carbon of the ring.
Preferred Type Ib substituents include:
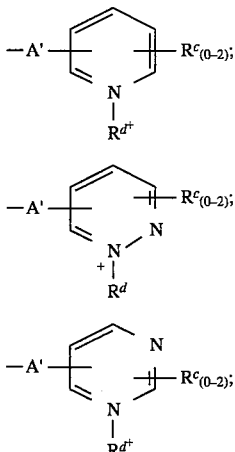

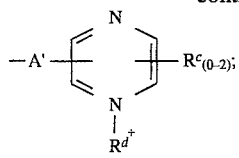
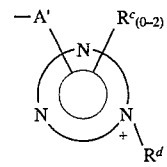
where the ring contains three carbon atoms;
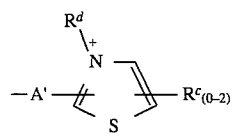
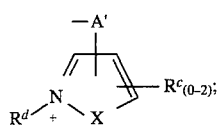
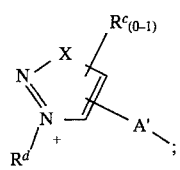
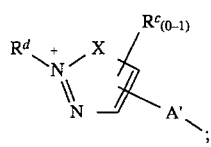
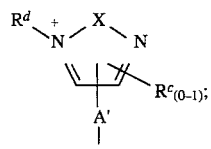
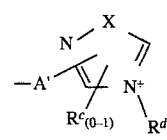
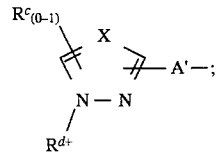
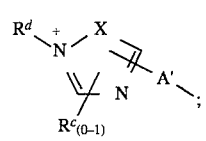
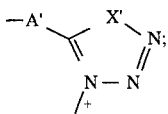
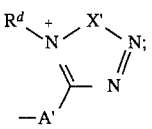
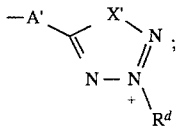
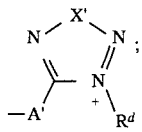
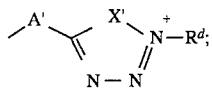
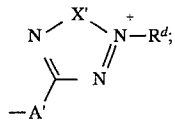
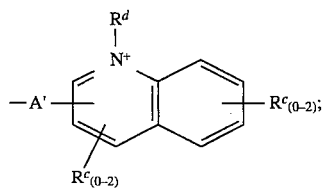
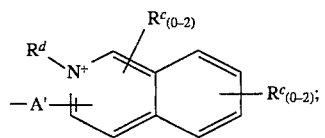
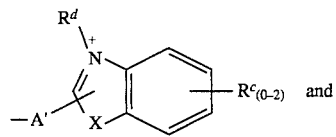
and
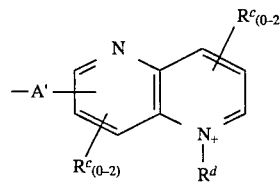
where $X=O$, S, or $NR^c$ and $X'=O$ or S. For structures of Type Ib, where $R^c$ and/or A' are shown to have indefinite positions, they are independently attached to any carbon atom of the ring.
Preferred Type Ic substituents include:
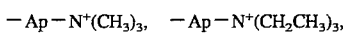

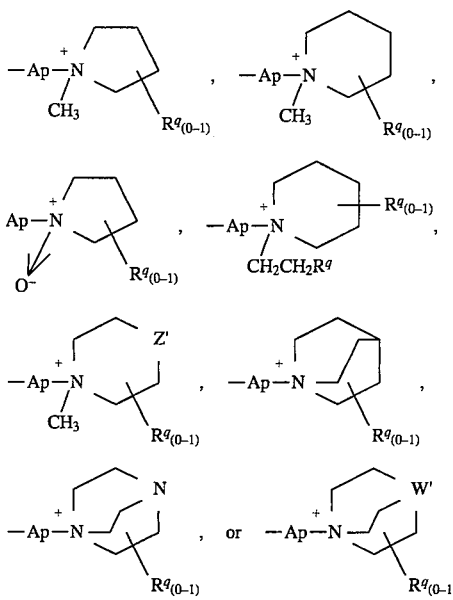

where Z' is O, S, NR$^e$, N(O)R$^e$, SO, SO$_2$ or N$^{+(Re)}$$_2$ and W' is N$^{+Re}$ or NO. For structures of Type Ic, where R$^q$ is shown to have an indefinite position, it may be attached to any carbon atom of the ring.

Preferred Type Id substituents include:

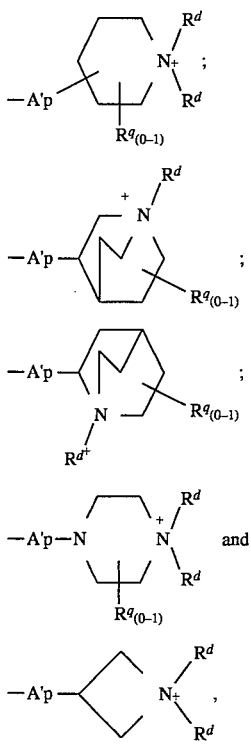

For structures of Type Id, where R$^q$ and/or A'p is shown to have an indefinite position, it may be attached to any carbon atom of the ring.

Preferred groups falling within Type Ie include the following:

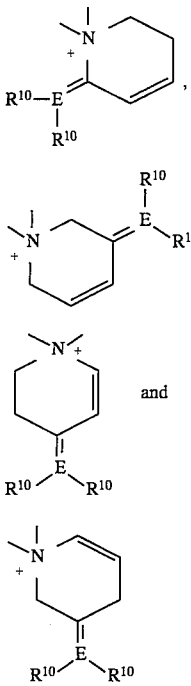

The R$^c$ substituents herein are intended to represent suitable further substitutents on the Type Ia or Ib substitutents for the carboline ring system. As seen above, these Type Ia or Ib substitutents are monocyclic or bicyclic aromatic groups containing heteroatoms. Given this class primary substituent, further suitable substituents may be readily discovered in the carbapenem art. For example, suitable substituents for Type Ia or Ib substituents are generally taught in U.S. Pat. No. 4,729,993 assigned to Merck and Co.

Broadly, R$^c$ may be the same or different and may be selected on an independent basis from the group as defined above. While a single such substitution is preferred, there is occasion to use up to two such substituents on an R$^a$, e.g., where it is desired to enhance the effect of a particular substitutent group by employing multiple substituents. The particular choice of R$^c$ will depend upon the situation. For instance, a specific R$^c$ may lend particular stability to a nitrogen cation. At other times it may be desired to employ a substitutent known to enhance antibacterial activity of the overall molecule against a particular bacterium, for example, while also employing a substituent known to improve some other property such as water solubility or the duration of action of the overall molecule.

The scope of R$^c$ herein includes two specific types of further substitutent attached to the Type Ia or Ib substitutent. A first type of R$_c$ are those attached to a ring carbon and a second type of R$^c$ are those attached to a neutral ring nitrogen. Persons skilled in the art will readily recognize that a wide range of organic substituents are suitably used as R$^c$. Persons skilled in the art will also recognize that some substituents including the —NRyRz substituents, useful for one purpose of R$^c$, i.e. carbon substitution, are not equally useful in the other, i.e. nitrogen substitution.

It is preferred that each Type Ia or Ib substituent have no more that two R$^c$ substituents which are other than hydrogen. Thus, the formula shown above for Type Ia substituents has up two $R^c$ substituents with the remainder of course being hydrogen. Further, the formula for the Type Ib substituents also allows up to two $R^c$. In accordance with these formulae, the previously listed more specific structures should be interpreted to have no more than two $R^c$ for each monocyclic or bicyclic group. Similarly for Type Ic or Id substituents it is preferred that any monocyclic or bicyclic group have no more than a single $R^a$ substituent.

Preferred $R^c$ attached to ring carbon atoms are —$NH_2$, —$SCH_3$, —$SOCH_3$, —$CH_2OH$, —$(CH_2)_2OH$, —$OCH_3$, —$COOM^b$, —$CH_2COOM^b$, —$CH_2CH_2COOM^b$, —$CH_2SOCH_3$, —$CH_2SCH_3$, —$SO_3M^b$, —$CH_2SO_3M^b$, —$CH_2CH_2SO_3M^b$, —Br, —Cl, —F, —I, —$CH_3$, $CH_2CH_3$, $CH_2CONH_2$ and $CH_2CON(C_1-C_4alkyl)_2$ where $M^b$ is defined above. Preferred $R^c$ attached to neutral ring nitrogen atoms are —$CH_2OH$, —$(CH_2)_2OH$, —$CH_2COOM^b$, —$CH_2CH_2COOM^b$, —$CH_2SOCH_3$, —$CH_2SCH_3$, —$CH_2SO_3M^b$, —$CH_2CH_2SO_3M^b$, —$CH_3$, $CH_2CH_3$, $CH_2CONH_2$ and $CH_2CON(C_1-C_4alkyl)_2$ where $M^b$ is defined above.

The $R^d$ substituents are attached to a cationic nitrogen which may or may not be aromatic. Preferred $R^d$ attached to cationic nitrogen atoms are hydrogen, —$CH_3$, $CH_2CH_3$, —$CH_2CH_2CH_3$, —$CH_2COOM^b$, —$CH_2SO_3M^b$, —$NH_2$ and O(−), where $M^b$ is defined above.

Suitable A spacer moieties include —$CH_2$—, —$CH_2$—$CH_2$—, —$CH_2$—$CH_2$—$CH_2$—, —$CH_2$—$CH_2OCH_2$—$CH_2$—, —$OCH_2CH_2$—, —$SOCH_2$—, —$SO_2CH_2$—, —$SCH_2CH_2$—, —$SOCH_2CH_2$—, —$SO_2CH_2CH_2$—, —$NHCH_2CH_2$——$N(CH_3)CH_2CH_2$—, $CH_2N(CH_3)CH_2CH_2$—, —$CONHCH_2CH_2$—, —$SO_2NHCH_2CH_2$—, —$COCH_2$—, —$CH$=$CHCH_2$— and —$CH_2OCH_2CH_2$—. Preferably, where Q is O, S, NH or $N(C_{1-4}alkyl)$, then n is 2-6.

Suitable A' are listed for A above. Further A' may suitable be —O—, —S—, —NH—, —$SO_2$—, —$SO_2NH$—, —CONH—, —CH=CH—, —$CH_2S$—, —$CH_2NH$—, —$CONHCH_2$— or —$SO_2NHCH_2$—.

Preferred $R^a$ groups of Type II include:

—$OCH_3$
—$OCH_2CH_2OH$
—F
—Br
—OH
—$OCONH_2$
—$SOCH_3$
—$SCH_2CH_2OH$ —$SO_2NH_2$
—NHCHO
—$NHCO_2CH_3$
—CN
—$COCH_3$
—CH=NOH
—CH=$NOCH_2CO_2H$
—$SO_2CH_2CH_2OH$
—CH=$NOCMe_2CO_2Me$
—$CONH_2$
—$CON(CH_3)_2$
—$CONHCH_2CONH_2$
—CONHOH
—tetrazoyl
—$SCF_3$
—$CONHSO_2Ph$
—$SO_3Na$
—$SO_2NHCONH_2$
—$OCH_2CO_2Na$
—$CF_3$
—Cl
—I
—$OCOCH_3$
—$SCH_3$
—$SO_2CH_3$
$SOCH_2CH_2OH$
—$SO_2N(CH_3)_2$
—$NHCOCH_3$
—$NHSO_2CH_3$
—CHO
—$COCH_2OH$
—CH=$NOCH_3$
—CH=$NOCME_2CO_2H$
—$CO_2CH_2CH_2OH$
—$CONHCH_3$
—$CONHCH_2CN$
—$CONHCH_2CO_2H$
—$CONCH_3$
—$CO_2Na$
—$PO_3NaH$
—$CONHSO_2NH_2$
—$SO_2NHCN$
—CH=CHCN
—CH=$CHCONH_2$
—C≡C—$CONH_2$
—$CH_2Oh$
—$CH_2CO_2Na$ and
—C≡C—CN
—$CH_2N_3$
—$CH_2I$ Preferred species falling within the invention include the compounds set forth in Tables 1–5 below.

TABLE 1

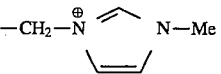

| R | R³ | Rʸ | Rᵃ | Rᵃ Position(s) |
|---|---|---|---|---|
| H | CH₃ | CH₃ | H | 1, 5–7 |
| CH₃ | CH₃ | CH₃ | H | 1, 5–7 |
| H | H | CH₃ | H | 1, 5–7 |
| CH₃ | H | CH₃ | H | 1, 5–7 |
| H | CH₃ | CH₂CH₃ | H | 1, 5–7 |
| CH₃ | CH₃ | CH₂CH₃ | H | 1, 5–7 |
| H | H | CH₂CH₃ | H | 1, 5–7 |
| CH₃ | H | CH₂CH₃ | H | 1, 5–7 |
| H | CH₃ | CH₂CONH₂ | H | 1, 5–7 |
| CH₃ | CH₃ | CH₂CONH₂ | H | 1, 5–7 |
| H | CH₃ | CH₂CH₂OH | H | 1, 5–7 |
| CH₃ | CH₃ | CH₂CH₂OH | H | 1, 5–7 |
| H | CH₃ | CH₃ | CN | 1 |
| CH₃ | CH₃ | CH₃ | CN | 1 |
| H | CH₃ | CH₃ | SMe | 1 |
| CH₃ | CH₃ | CH₃ | SMe | 1 |
| H | CH₃ | CH₃ | SO₂Me | 1 |
| CH₃ | CH₃ | CH₃ | SO₂Me | 1 |
| H | CH₃ | CH₃ | CONH₂ | 1 |
| CH₃ | CH₃ | CH₃ | CONH₂ | 1 |
| H | CH₃ | CH₃ | Br | 1 |
| CH₃ | CH₃ | CH₃ | Br | 1 |
| H | CH₃ | CH₃ | NH₂ | 7 |
| CH₃ | CH₃ | CH₃ | NH₂ | 7 |
| H | CH₃ | Absent¹ | 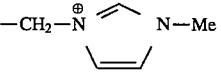 | 7 |
| CH₃ | CH₃ | Absent | 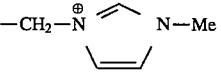 | 7 |
| H | CH₃ | Absent | 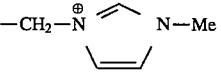 | 6 |
| CH₃ | CH₃ | Absent | 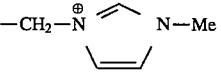 | 6 |
| H | CH₃ | Absent | 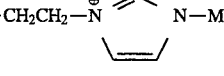 | 7 |
| CH₃ | CH₃ | Absent | 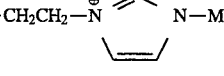 | 7 |
| H | CH₃ | Absent | 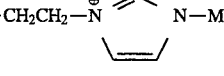 | 6 |
| CH₃ | CH₃ | Absent | 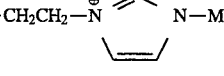 | 6 |
| H | CH₃ | Absent | 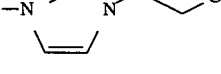 | 7 |

TABLE 1-continued
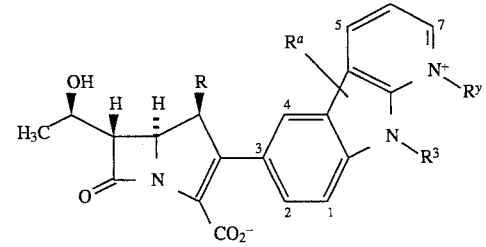
| R | R³ | Rʸ | Rᵃ | Rᵃ Position(s) |
|---|---|---|---|---|
| CH₃ | CH₃ | Absent | 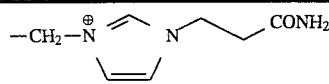 | 7 |
| H | CH₃ | Absent | 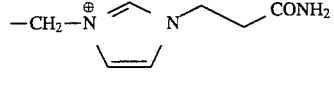 | 6 |
| CH₃ | CH₃ | Absent |  | 6 |
| H | CH₃ | Absent | 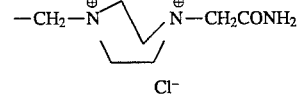 | 7 |
| CH₃ | CH₃ | Absent | 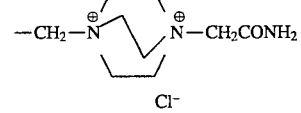 | 7 |
| H | CH₃ | Absent | 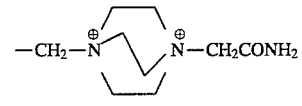 | 6 |
| CH₃ | CH₃ | Absent | 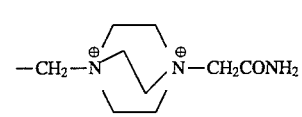 | 6 |
| H | CH₃ | Absent | 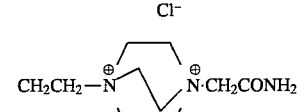 | 7 |
| CH₃ | CH₃ | Absent | 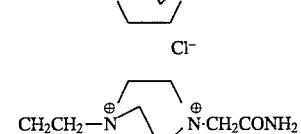 | 7 |
| H | CH₃ | Absent | 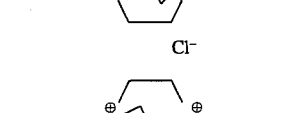 | 6 |

TABLE 1-continued

[Structure: carbapenem core with hydroxyethyl group, linked to a substituted phenyl ring (positions 1-4) bearing NR³ and a pyridinium ring (positions 5-7) with N⁺-Rʸ and Rᵃ substituent]

| R | R³ | Rʸ | Rᵃ | Rᵃ Position(s) |
|---|---|---|---|---|
| CH₃ | CH₃ | Absent | $-CH_2CH_2-\overset{\oplus}{N}\smile\overset{\oplus}{N}-CH_2CONH_2$ ·Cl⁻ (piperazinium) | 6 |
| H | CH₃ | Absent | $-CH_2-\overset{\oplus}{N}(CH_3)\smile\overset{\oplus}{N}-(CH_3)_2$ ·Cl⁻ (piperazinium) | 7 |
| CH₃ | CH₃ | Absent | $-CH_2-\overset{\oplus}{N}(CH_3)\smile\overset{\oplus}{N}-(CH_3)_2$ ·Cl⁻ | 7 |
| H | CH₃ | Absent | $-CH_2-\overset{\oplus}{N}(CH_3)\smile\overset{\oplus}{N}-(CH_3)_2$ ·Cl⁻ | 6 |
| CH₃ | CH₃ | Absent | $-CH_2-\overset{\oplus}{N}(CH_3)\smile\overset{\oplus}{N}-(CH_3)_2$ ·Cl⁻ | 6 |
| H | CH₃ | Absent | $-CH_2-\overset{\oplus}{N}$(4-aminopyridinium)-NH₂ | 7 |
| CH₃ | CH₃ | Absent | $-CH_2-\overset{\oplus}{N}$(4-aminopyridinium)-NH₂ | 7 |
| H | CH₃ | Absent | $-CH_2-\overset{\oplus}{N}$(4-aminopyridinium)-NH₂ | 6 |
| CH₃ | CH₃ | Absent | $-CH_2-\overset{\oplus}{N}$(4-aminopyridinium)-NH₂ | 6 |
| H | CH₃ | Absent | $-CH_2-\overset{\oplus}{N}$(pyridinium)-CH₂SMe | 7 |

TABLE 1-continued

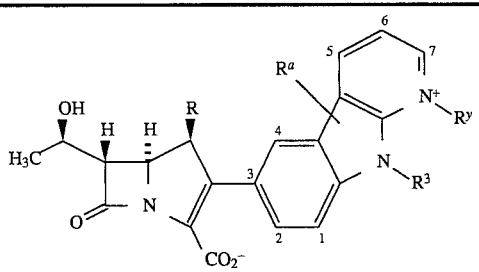

| R | R³ | Rʸ | Rᵃ | Rᵃ Position(s) |
|---|---|---|---|---|
| $CH_3$ | $CH_3$ | Absent | —CH₂—N⁺(pyridyl-CH₂-SMe) | 7 |

[1] When $R^y$ is absent, the N atom to which it is shown attached is non-quaternary.

TABLE 2

| $R^{a1}$ | $R^3$ | $R^Y$ | $R^{a2}$ |
|---|---|---|---|
| CN | H | Absent[1] | —CH₂—N⁺(piperazine)N⁺—CH₂CONH₂ Cl⁻ |
| CN | $CH_3$ | Absent | —CH₂—N⁺(piperazine)N⁺—CH₂CONH₂ Cl⁻ |
| Br | H | Absent | —CH₂—N⁺(piperazine)N⁺—CH₂CONH₂ Cl⁻ |
| Br | $CH_3$ | Absent | —CH₂—N⁺(piperazine)N⁺—CH₂CONH₂ Cl⁻ |
| $SCH_3$ | H | Absent | —CH₂—N⁺(piperazine)N⁺—CH₂CONH₂ Cl⁻ |
| $SCH_3$ | $CH_3$ | Absent | —CH₂—N⁺(piperazine)N⁺—CH₂CONH₂ Cl⁻ |
| $SO_2CH_3$ | H | Absent | —CH₂—N⁺(piperazine)N⁺—CH₂CONH₂ Cl⁻ |

TABLE 2-continued

[Structure: carbapenem core with 4-hydroxyethyl azetidinone fused to pyrroline carboxylate, bearing a phenyl group substituted at positions 1 (R$^{a1}$), 2, 3, 4, with N-R$^3$ and a pyridinium ring at position with R$^y$ on N$^+$ and R$^{a2}$ at position 7]

| R$^{a1}$ | R$^3$ | R$^Y$ | R$^{a2}$ |
|---|---|---|---|
| SO$_2$CH$_3$ | CH$_3$ | Absent | —CH$_2$—N$^+$(CH$_2$CH$_2$)$_2$N$^+$—CH$_2$CONH$_2$ Cl$^-$ (piperazinium) |
| CONH$_2$ | H | Absent | —CH$_2$—N$^+$(CH$_2$CH$_2$)$_2$N$^+$—CH$_2$CONH$_2$ Cl$^-$ |
| CONH$_2$ | CH$_3$ | Absent | —CH$_2$—N$^+$(CH$_2$CH$_2$)$_2$N$^+$—CH$_2$CONH$_2$ Cl$^-$ |
| CN | H | CH$_3$ | —CH$_2$·N$^+$=\\=N—CH$_3$ Cl$^-$ (imidazolium) |
| CN | CH$_3$ | CH$_3$ | —CH$_2$·N$^+$=\\=N—CH$_3$ Cl$^-$ |
| Br | H | CH$_3$ | —CH$_2$·N$^+$=\\=N—CH$_3$ Cl$^-$ |
| Br | CH$_3$ | CH$_3$ | —CH$_2$·N$^+$=\\=N—CH$_3$ Cl$^-$ |
| SMe | H | CH$_3$ | —CH$_2$·N$^+$=\\=N—CH$_3$ Cl$^-$ |
| SMe | CH$_3$ | CH$_3$ | —CH$_2$·N$^+$=\\=N—CH$_3$ Cl$^-$ |
| SO$_2$CH$_3$ | H | CH$_3$ | —CH$_2$·N$^+$=\\=N—CH$_3$ Cl$^-$ |
| SO$_2$CH$_3$ | CH$_3$ | CH$_3$ | —CH$_2$·N$^+$=\\=N—CH$_3$ Cl$^-$ |
| CONH | H | CH$_3$ | —CH$_2$·N$^+$=\\=N—CH$_3$ Cl$^-$ |
| CONH$_2$ | CH$_3$ | CH$_3$ | —CH$_2$·N$^+$=\\=N—CH$_3$ Cl$^-$ |
| CN | H | Absent | —CH$_2$—N$^+$(CH$_3$)(CH$_2$CH$_2$)$_2$N$^+$—Me$_2$ Cl$^-$ |

TABLE 2-continued

[Structure shown: carbapenem core with substituents including OH, CH₃, H, R groups, CO₂⁻, and aromatic ring numbered 1-7 with $R^{a1}$, $R^{a2}$, $R^3$, $R^y$, N⁺ substituents]

| $R^{a1}$ | $R^3$ | $R^Y$ | $R^{a2}$ |
|---|---|---|---|
| CN | CH₃ | Absent | $-CH_2-\overset{+}{\underset{CH_3}{N}}\diagup\diagdown\overset{+}{N}-Me_2$  Cl⁻ |
| Br | H | Absent | $-CH_2-\overset{+}{\underset{CH_3}{N}}\diagup\diagdown\overset{+}{N}-Me_2$  Cl⁻ |
| Br | CH₃ | Absent | $-CH_2-\overset{+}{\underset{CH_3}{N}}\diagup\diagdown\overset{+}{N}-Me_2$  Cl⁻ |
| SMe | H | Absent | $-CH_2-\overset{+}{\underset{CH_3}{N}}\diagup\diagdown\overset{+}{N}-Me_2$  Cl⁻ |
| SMe | CH₃ | Absent | $-CH_2-\overset{+}{\underset{CH_3}{N}}\diagup\diagdown\overset{+}{N}-Me_2$  Cl⁻ |
| SO₂Me | H | Absent | $-CH_2-\overset{+}{\underset{CH_3}{N}}\diagup\diagdown\overset{+}{N}-Me_2$  Cl⁻ |
| SO₂Me | CH₃ | Absent | $-CH_2-\overset{+}{\underset{CH_3}{N}}\diagup\diagdown\overset{+}{N}-Me_2$  Cl⁻ |
| CONH₂ | H | Absent | $-CH_2-\overset{+}{\underset{CH_3}{N}}\diagup\diagdown\overset{+}{N}-Me_2$  Cl⁻ |
| CONH₂ | CH₃ | Absent | $-CH_2-\overset{+}{\underset{CH_3}{N}}\diagup\diagdown\overset{+}{N}-Me_2$  Cl⁻ |
| CN | H | CH₃ | $-CH_2\cdot\overset{+}{N}$(imidazole)$N-CH_2CH_2CONH_2$  Cl⁻ |
| CN | CH₃ | CH₃ | $-CH_2\cdot\overset{+}{N}$(imidazole)$N-CH_2CH_2CONH_2$  Cl⁻ |
| Br | H | CH₃ | $-CH_2\cdot\overset{+}{N}$(imidazole)$N-CH_2CH_2CONH_2$  Cl⁻ |

TABLE 2-continued

Structure (as shown): core bicyclic β-lactam with hydroxyethyl group, substituents labeled $R^{a1}$, $R^3$, $R^y$, $R^{a2}$ on aryl/pyridinium ring; positions 1–7 labeled; $CO_2^-$ group.

| $R^{a1}$ | $R^3$ | $R^Y$ | $R^{a2}$ |
|---|---|---|---|
| Br | CH₃ | CH₃ | $-CH_2\overset{+}{N}$(pyrrole)$N$-CH₂CH₂-CONH₂, Cl⁻ |
| SMe | H | CH₃ | $-CH_2\overset{+}{N}$(pyrrole)$N$-CH₂CH₂-CONH₂, Cl⁻ |
| SMe | CH₃ | CH₃ | $-CH_2\overset{+}{N}$(pyrrole)$N$-CH₂CH₂-CONH₂, Cl⁻ |
| SO₂Me | H | CH₃ | $-CH_2\overset{+}{N}$(pyrrole)$N$-CH₂CH₂-CONH₂, Cl⁻ |
| SO₂Me | CH₃ | CH₃ | $-CH_2\overset{+}{N}$(pyrrole)$N$-CH₂CH₂-CONH₂, Cl⁻ |
| CONH₂ | H | CH₃ | $-CH_2\overset{+}{N}$(pyrrole)$N$-CH₂CH₂-CONH₂, Cl⁻ |
| CONH₂ | CH₃ | CH₃ | $-CH_2\overset{+}{N}$(pyrrole)$N$-CH₂CH₂-CONH₂, Cl⁻ |
| CN | H | CH₂CH₃ | $-CH_2\overset{+}{N}$(pyrrole)$N$-CH₂CH₂-CONH₂, Cl⁻ |
| CN | CH₃ | CH₂CH₃ | $-CH_2\overset{+}{N}$(pyrrole)$N$-CH₂CH₂-CONH₂, Cl⁻ |
| Br | H | CH₂CH₃ | $-CH_2\overset{+}{N}$(pyrrole)$N$-CH₂CH₂-CONH₂, Cl⁻ |
| Br | CH₃ | CH₂CH₃ | $-CH_2\overset{+}{N}$(pyrrole)$N$-CH₂CH₂-CONH₂, Cl⁻ |
| SMe | H | CH₂CH₃ | $-CH_2\overset{+}{N}$(pyrrole)$N$-CH₂CH₂-CONH₂, Cl⁻ |
| SMe | CH₃ | CH₂CH₃ | $-CH_2\overset{+}{N}$(pyrrole)$N$-CH₂CH₂-CONH₂, Cl⁻ |
| SO₂Me | H | CH₂CH₃ | $-CH_2\overset{+}{N}$(pyrrole)$N$-CH₂CH₂-CONH₂, Cl⁻ |
| SO₂Me | CH₃ | CH₂CH₃ | $-CH_2\overset{+}{N}$(pyrrole)$N$-CH₂CH₂-CONH₂, Cl⁻ |

TABLE 2-continued

| $R^{a1}$ | $R^3$ | $R^Y$ | $R^{a2}$ |
|---|---|---|---|
| $CONH_2$ | H | $CH_2H_3$ | $-CH_2\overset{+}{\cdot}N\diagup\diagdown N\diagup CONH_2$  $Cl^-$ |
| $CONH_2$ | $CH_3$ | $CH_2CH_3$ | $-CH_2\overset{+}{\cdot}N\diagup\diagdown N\diagup CONH_2$  $Cl^-$ |

[1] When $R^y$ is absent, the N atom to which it is shown attached is non-quaternary.

TABLE 3

| R | $R^3$ | $R^y$ | $R^a$ | $R^a$ Position(s) |
|---|---|---|---|---|
| H | $CH_3$ | $CH_3$ | H | 1, 5, 6, 8 |
| $CH_3$ | $CH_3$ | $CH_3$ | H | 1, 5, 6, 8 |
| H | H | $CH_3$ | H | 1, 5, 6, 8 |
| $CH_3$ | H | $CH_3$ | H | 1, 5, 6, 8 |
| H | $CH_3$ | $CH_2CH_3$ | H | 1, 5, 6, 8 |
| $CH_3$ | $CH_3$ | $CH_2CH_3$ | H | 1, 5, 6, 8 |
| H | H | $CH_2CH_3$ | H | 1, 5, 6, 8 |
| $CH_3$ | H | $CH_2CH_3$ | H | 1, 5, 6, 8 |
| H | $CH_3$ | $CH_2CONH_2$ | H | 1, 5, 6, 8 |
| $CH_3$ | $CH_3$ | $CH_2CONH_2$ | H | 1, 5, 6, 8 |
| H | $CH_3$ | $CH_2CH_2OH$ | H | 1, 5, 6, 8 |
| $CH_3$ | $CH_3$ | $CH_2CH_2OH$ | H | 1, 5, 6, 8 |
| H | $CH_3$ | $CH_3$ | CN | 1 |
| $CH_3$ | $CH_3$ | $CH_3$ | CN | 1 |
| H | $CH_3$ | $CH_3$ | SMe | 1 |
| $CH_3$ | $CH_3$ | $CH_3$ | SMe | 1 |
| H | $CH_3$ | $CH_3$ | $SO_2Me$ | 1 |
| $CH_3$ | $CH_3$ | $CH_3$ | $SO_2Me$ | 1 |
| H | $CH_3$ | $CH_3$ | $CONH_2$ | 1 |
| $CH_3$ | $CH_3$ | $CH_3$ | $CONH_2$ | 1 |
| H | $CH_3$ | $CH_3$ | Br | 1 |
| $CH_3$ | $CH_3$ | $CH_3$ | Br | 1 |
| H | $CH_3$ | $CH_3$ | $NH_2$ | 6 |
| $CH_3$ | $CH_3$ | $CH_3$ | $NH_2$ | 6 |
| H | $CH_3$ | $CH_3$ | $NH_2$ | 8 |
| $CH_3$ | $CH_3$ | $CH_3$ | $NH_2$ | 8 |
| H | $CH_3$ | Absent[1] | $-CH_2-\overset{\oplus}{N}\diagup\diagdown N-Me$ | 6 |
| $CH_3$ | $CH_3$ | Absent | $-CH_2-\overset{\oplus}{N}\diagup\diagdown N-Me$ | 6 |

TABLE 3-continued

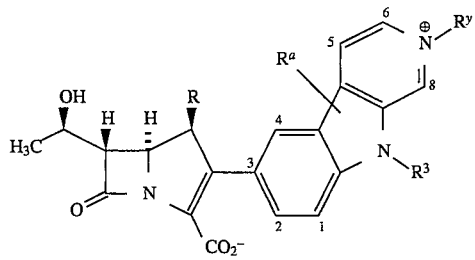

| R | R³ | R^y | R^a | R^a Position(s) |
|---|----|-----|-----|-----------------|
| H | CH₃ | Absent | —CH₂—N⊕⟨imidazole⟩N—Me | 8 |
| CH₃ | CH₃ | Absent | —CH₂—N⊕⟨imidazole⟩N—Me | 8 |
| H | CH₃ | Absent | —CH₂CH₂—N⊕⟨imidazole⟩N—Me | 6 |
| CH₃ | CH₃ | Absent | —CH₂CH₂—N⊕⟨imidazole⟩N—Me | 6 |
| H | CH₃ | Absent | —CH₂CH₂—N⊕⟨imidazole⟩N—Me | 8 |
| CH₃ | CH₃ | Absent | —CH₂CH₂—N⊕⟨imidazole⟩N—Me | 8 |
| H | CH₃ | Absent | —CH₂—N⊕⟨imidazole⟩N—CH₂CH₂CONH₂ | 6 |
| CH₃ | CH₃ | Absent | —CH₂—N⊕⟨imidazole⟩N—CH₂CH₂CONH₂ | 6 |
| H | CH₃ | Absent | —CH₂—N⊕⟨imidazole⟩N—CH₂CH₂CONH₂ | 8 |
| CH₃ | CH₃ | Absent | —CH₂—N⊕⟨imidazole⟩N—CH₂CH₂CONH₂ | 8 |
| H | CH₃ | Absent | —CH₂—N⊕⟨DABCO⟩N⊕—CH₂CONH₂ | 6 |
| CH₃ | CH₃ | Absent | —CH₂—N⊕⟨DABCO⟩N⊕—CH₂CONH₂ | 6 |
| H | CH₃ | Absent | —CH₂—N⊕⟨DABCO⟩N⊕—CH₂CONH₂ | 8 |
| CH₃ | CH₃ | Absent | —CH₂—N⊕⟨DABCO⟩N⊕—CH₂CONH₂ | 8 |

TABLE 3-continued

[Structure shown: A chemical compound with OH, H₃C, H, H, R substituents on a β-lactam ring with CO₂⁻, connected to a benzene ring (positions 1,2,3,4) bearing NR³, and a pyridinium ring (positions 5,6,8) with Rᵃ and N⊕—Rʸ]

| R | R³ | Rʸ | Rᵃ | Rᵃ Position(s) |
|---|---|---|---|---|
| H | CH₃ | Absent | CH₂CH₂—N⊕(ring)N⊕·CH₂CONH₂ | 6 |
| CH₃ | CH₃ | Absent | CH₂CH₂—N⊕(ring)N⊕·CH₂CONH₂ | 6 |
| H | CH₃ | Absent | CH₂CH₂—N⊕(ring)N⊕·CH₂CONH₂ | 8 |
| CH₃ | CH₃ | Absent | CH₂CH₂—N⊕(ring)N⊕·CH₂CONH₂ | 8 |
| H | CH₃ | Absent | —CH₂—N⊕(CH₃)(ring)N⊕—(CH₃)₂ | 6 |
| CH₃ | CH₃ | Absent | —CH₂—N⊕(CH₃)(ring)N⊕—(CH₃)₂ | 6 |
| H | CH₃ | Absent | —CH₂—N⊕(CH₃)(ring)N⊕—(CH₃)₂ | 8 |
| CH₃ | CH₃ | Absent | —CH₂—N⊕(CH₃)(ring)N⊕—(CH₃)₂ | 8 |
| H | CH₃ | Absent | —CH₂—N⊕(pyridinium)—NH₂ | 6 |
| CH₃ | CH₃ | Absent | —CH₂—N⊕(pyridinium)—NH₂ | 6 |
| H | CH₃ | Absent | —CH₂—N⊕(pyridinium)—NH₂ | 8 |
| CH₃ | CH₃ | Absent | —CH₂—N⊕(pyridinium)—NH₂ | 8 |

TABLE 3-continued

[Structure: carbapenem core with OH, H₃C, H, R substituents, aryl ring (positions 1-4) connected to pyridinium-containing group with Rᵃ, Ry, R³ substituents; position 7 N⊕-Ry, position 8]

| R | R³ | Ry | Rᵃ | Rᵃ Position(s) |
|---|----|----|-----|----------------|
| H | CH₃ | Absent | —CH₂—N⊕(pyridinium)—CH₂SMe | 6 |
| CH₃ | CH₃ | Absent | —CH₂—N⊕(pyridinium)—SMe | 6 |
| H | CH₃ | Absent | —CH₂—N⊕(pyridinium)—SMe | 8 |
| CH₃ | CH₃ | Absent | —CH₂—N⊕(pyridinium)—SMe | 8 |

¹When Ry is absent the N atom at position 7 is non-quaternary.

TABLE 4

[Structure: carbapenem core with OH, H₃C, H, R substituents, aryl ring (positions 1-4) with Rᵃ¹ at position 1, N—R³, connected to side chain with Rᵃ³ (=H) at position 6, N⊕-Ry at position 7, Rᵃ² at position 8]

Rᵃ³ represents H

| Rᵃ¹ | R³ | RY | Rᵃ² |
|-----|----|----|------|
| CN | H | Absent¹ | —CH₂—N⁺(piperazinium)N⁺—CH₂CONH₂ Cl⁻ |
| CN | CH₃ | Absent | —CH₂—N⁺(piperazinium)N⁺—CH₂CONH₂ Cl⁻ |

TABLE 4-continued
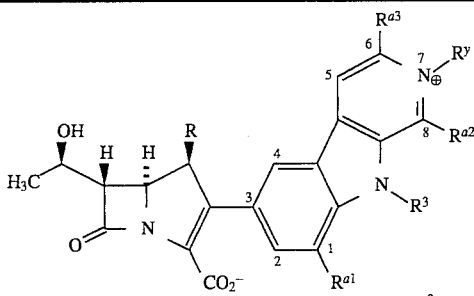
$R^{a3}$ represents H
| $R^{a1}$ | $R^3$ | $R^Y$ | $R^{a2}$ |
|---|---|---|---|
| Br | H | Absent | 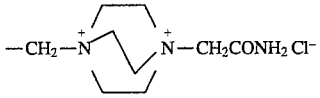 |
| Br | CH$_3$ | Absent | 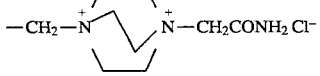 |
| SCH$_3$ | H | Absent | 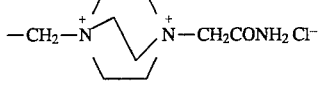 |
| SCH$_3$ | CH$_3$ | Absent | 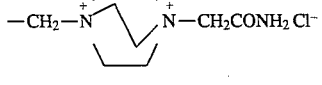 |
| SO$_2$CH$_3$ | H | Absent | 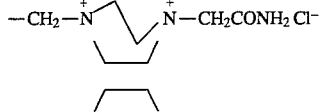 |
| SO$_2$CH$_3$ | CH$_3$ | Absent | 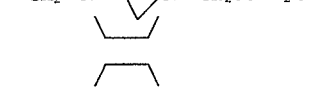 |
| CONH$_2$ | H | Absent | 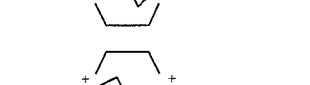 |
| CONH$_2$ | CH$_3$ | Absent | 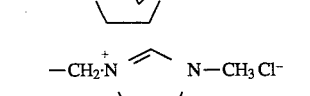 |
| CN | H | CH$_3$ | 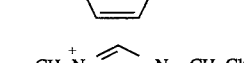 |
| CN | CH$_3$ | CH$_3$ | 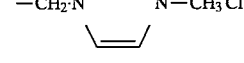 |
| Br | H | CH$_3$ |  |
| Br | CH$_3$ | CH$_3$ | 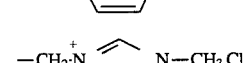 |
| SMe | H | CH$_3$ | 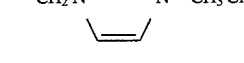 |

TABLE 4-continued

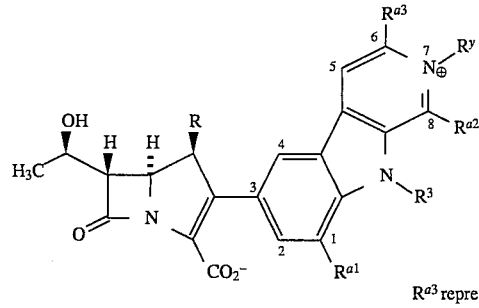

$R^{a3}$ represents H

| $R^{a1}$ | $R^3$ | $R^Y$ | $R^{a2}$ |
|---|---|---|---|
| SMe | $CH_3$ | $CH_3$ | $-CH_2\overset{+}{-}N\underset{\smile}{\overset{\frown}{=}}N-CH_3\ Cl^-$ |
| $SO_2CH_3$ | H | $CH_3$ | $-CH_2\overset{+}{-}N\underset{\smile}{\overset{\frown}{=}}N-CH_3\ Cl^-$ |
| $SO_2CH_3$ | $CH_3$ | $CH_3$ | $-CH_2\overset{+}{-}N\underset{\smile}{\overset{\frown}{=}}N-CH_3\ Cl^-$ |
| $CONH_2$ | H | $CH_3$ | $-CH_2\overset{+}{-}N\underset{\smile}{\overset{\frown}{=}}N-CH_3\ Cl^-$ |
| $CONH_2$ | $CH_3$ | $CH_3$ | $-CH_2\overset{+}{-}N\underset{\smile}{\overset{\frown}{=}}N-CH_3\ Cl^-$ |
| CN | H | Absent | $-CH_2-\underset{CH_3}{\overset{+}{N}}\underset{\smile}{\overset{\frown}{\diagup}}\overset{+}{N}-Me_2\ Cl^-$ |
| CN | $CH_3$ | Absent | $-CH_2-\underset{CH_3}{\overset{+}{N}}\underset{\smile}{\overset{\frown}{\diagup}}\overset{+}{N}-Me_2\ Cl^-$ |
| Br | H | Absent | $-CH_2-\underset{CH_3}{\overset{+}{N}}\underset{\smile}{\overset{\frown}{\diagup}}\overset{+}{N}-Me_2\ Cl^-$ |
| Br | $CH_3$ | Absent | $-CH_2-\underset{CH_3}{\overset{+}{N}}\underset{\smile}{\overset{\frown}{\diagup}}\overset{+}{N}-Me_2\ Cl^-$ |
| SMe | H | Absent | $-CH_2-\underset{CH_3}{\overset{+}{N}}\underset{\smile}{\overset{\frown}{\diagup}}\overset{+}{N}-Me_2\ Cl^-$ |
| SMe | $CH_3$ | Absent | $-CH_2-\underset{CH_3}{\overset{+}{N}}\underset{\smile}{\overset{\frown}{\diagup}}\overset{+}{N}-Me_2\ Cl^-$ |
| $SO_2Me$ | H | Absent | $-CH_2-\underset{CH_3}{\overset{+}{N}}\underset{\smile}{\overset{\frown}{\diagup}}\overset{+}{N}-Me_2\ Cl^-$ |

TABLE 4-continued

[Structure diagram of the compound with positions 1-8 labeled, showing a β-lactam with hydroxyethyl group, pyrrolidine, phenyl ring with substituents $R^{a1}$, $NR^3$, and a vinyl pyridinium/imidazolium group with $R^{a2}$, $R^{a3}$, $R^y$]

$R^{a3}$ represents H

| $R^{a1}$ | $R^3$ | $R^Y$ | $R^{a2}$ |
|---|---|---|---|
| SO$_2$Me | CH$_3$ | Absent | —CH$_2$—N$^+$(CH$_3$)(CH$_2$CH$_2$)$_2$N$^+$—Me$_2$ Cl$^-$ (piperazinium) |
| CONH$_2$ | H | Absent | —CH$_2$—N$^+$(CH$_3$)(CH$_2$CH$_2$)$_2$N$^+$—Me$_2$ Cl$^-$ |
| CONH$_2$ | CH$_3$ | Absent | —CH$_2$—N$^+$(CH$_3$)(CH$_2$CH$_2$)$_2$N$^+$—Me$_2$ Cl$^-$ |
| CN | H | CH$_3$ | —CH$_2$·N$^+$(imidazole)N—CH$_2$CH$_2$CONH$_2$ Cl$^-$ |
| CN | CH$_3$ | CH$_3$ | —CH$_2$·N$^+$(imidazole)N—CH$_2$CH$_2$CONH$_2$ Cl$^-$ |
| Br | H | CH$_3$ | —CH$_2$·N$^+$(imidazole)N—CH$_2$CH$_2$CONH$_2$ Cl$^-$ |
| Br | CH$_3$ | CH$_3$ | —CH$_2$·N$^+$(imidazole)N—CH$_2$CH$_2$CONH$_2$ Cl$^-$ |
| SMe | H | CH$_3$ | —CH$_2$·N$^+$(imidazole)N—CH$_2$CH$_2$CONH$_2$ Cl$^-$ |
| SMe | CH$_3$ | CH$_3$ | —CH$_2$·N$^+$(imidazole)N—CH$_2$CH$_2$CONH$_2$ Cl$^-$ |
| SO$_2$Me | H | CH$_3$ | —CH$_2$·N$^+$(imidazole)N—CH$_2$CH$_2$CONH$_2$ Cl$^-$ |
| SO$_2$Me | CH$_3$ | CH$_3$ | —CH$_2$·N$^+$(imidazole)N—CH$_2$CH$_2$CONH$_2$ Cl$^-$ |
| CONH$_2$ | H | CH$_3$ | —CH$_2$·N$^+$(imidazole)N—CH$_2$CH$_2$CONH$_2$ Cl$^-$ |
| CONH$_2$ | CH$_3$ | CH$_3$ | —CH$_2$·N$^+$(imidazole)N—CH$_2$CH$_2$CONH$_2$ Cl$^-$ |
| CN | H | CH$_2$CH$_3$ | —CH$_2$·N$^+$(imidazole)N—CH$_2$CH$_2$CONH$_2$ Cl$^-$ |

TABLE 4-continued

[Structure diagram showing a carbapenem derivative with labeled positions 1-8, substituents $R^{a1}$, $R^{a2}$, $R^{a3}$, $R^3$, $R^y$, R, OH, $H_3C$, $CO_2^-$, with $N^\oplus$ at position 7]

$R^{a3}$ represents H

| $R^{a1}$ | $R^3$ | $R^Y$ | $R^{a2}$ |
|---|---|---|---|
| CN | $CH_3$ | $CH_2CH_3$ | $-CH_2\overset{+}{-}N\underset{\diagdown\!=\!\diagup}{\diagup\!\!\diagdown}N\diagdown CONH_2$   $Cl^-$ |
| Br | H | $CH_2CH_3$ | $-CH_2\overset{+}{-}N\underset{\diagdown\!=\!\diagup}{\diagup\!\!\diagdown}N\diagdown CONH_2$   $Cl^-$ |
| Br | $CH_3$ | $CH_2CH_3$ | $-CH_2\overset{+}{-}N\underset{\diagdown\!=\!\diagup}{\diagup\!\!\diagdown}N\diagdown CONH_2$   $Cl^-$ |
| SMe | H | $CH_2CH_3$ | $-CH_2\overset{+}{-}N\underset{\diagdown\!=\!\diagup}{\diagup\!\!\diagdown}N\diagdown CONH_2$   $Cl^-$ |
| SMe | $CH_3$ | $CH_2CH_3$ | $-CH_2\overset{+}{-}N\underset{\diagdown\!=\!\diagup}{\diagup\!\!\diagdown}N\diagdown CONH_2$   $Cl^-$ |
| $SO_2Me$ | H | $CH_2CH_3$ | $-CH_2\overset{+}{-}N\underset{\diagdown\!=\!\diagup}{\diagup\!\!\diagdown}N\diagdown CONH_2$   $Cl^-$ |
| $SO_2Me$ | $CH_3$ | $CH_2CH_3$ | $-CH_2\overset{+}{-}N\underset{\diagdown\!=\!\diagup}{\diagup\!\!\diagdown}N\diagdown CONH_2$   $Cl^-$ |
| $CONH_2$ | H | $CH_2CH_3$ | $-CH_2\overset{+}{-}N\underset{\diagdown\!=\!\diagup}{\diagup\!\!\diagdown}N\diagdown CONH_2$   $Cl^-$ |
| $CONH_2$ | $CH_3$ | $CH_2CH_3$ | $-CH_2\overset{+}{-}N\underset{\diagdown\!=\!\diagup}{\diagup\!\!\diagdown}N\diagdown CONH_2$   $Cl^-$ |

[1]When $R^y$ is absent the N atom at position 7 is non-quaternary.

TABLE 5

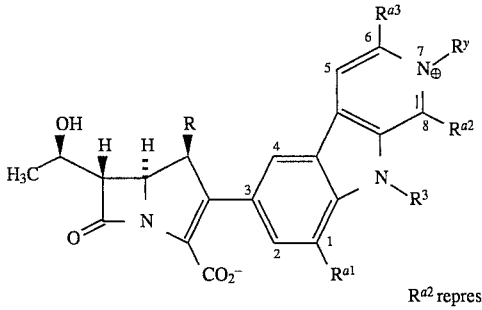

R$^{a2}$ represents H

| R$^{a1}$ | R$^3$ | R$^Y$ | R$^{a3}$ |
|---|---|---|---|
| CN | H | Absent[1] | —CH$_2$—N$^+$(CH$_2$CH$_2$)$_2$N$^+$—CH$_2$CONH$_2$ Cl$^-$ |
| CN | CH$_3$ | Absent | —CH$_2$—N$^+$(CH$_2$CH$_2$)$_2$N$^+$—CH$_2$CONH$_2$ Cl$^-$ |
| Br | H | Absent | —CH$_2$—N$^+$(CH$_2$CH$_2$)$_2$N$^+$—CH$_2$CONH$_2$ Cl$^-$ |
| Br | CH$_3$ | Absent | —CH$_2$—N$^+$(CH$_2$CH$_2$)$_2$N$^+$—CH$_2$CONH$_2$ Cl$^-$ |
| SCH$_3$ | H | Absent | —CH$_2$—N$^+$(CH$_2$CH$_2$)$_2$N$^+$—CH$_2$CONH$_2$ Cl$^-$ |
| SCH$_3$ | CH$_3$ | Absent | —CH$_2$—N$^+$(CH$_2$CH$_2$)$_2$N$^+$—CH$_2$CONH$_2$ Cl$^-$ |
| SO$_2$CH$_3$ | H | Absent | —CH$_2$—N$^+$(CH$_2$CH$_2$)$_2$N$^+$—CH$_2$CONH$_2$ Cl$^-$ |
| SO$_2$CH$_3$ | CH$_3$ | Absent | —CH$_2$—N$^+$(CH$_2$CH$_2$)$_2$N$^+$—CH$_2$CONH$_2$ Cl$^-$ |
| CONH$_2$ | H | Absent | —CH$_2$—N$^+$(CH$_2$CH$_2$)$_2$N$^+$—CH$_2$CONH$_2$ Cl$^-$ |
| CONH$_2$ | CH$_3$ | Absent | —CH$_2$—N$^+$(CH$_2$CH$_2$)$_2$N$^+$—CH$_2$CONH$_2$ Cl$^-$ |
| CN | H | CH$_3$ | —CH$_2$·N$^+$=CH—CH=CH—N—CH$_3$ Cl$^-$ |
| CN | CH$_3$ | CH$_3$ | —CH$_2$·N$^+$=CH—CH=CH—N—CH$_3$ Cl$^-$ |

TABLE 5-continued

[Structure: carbapenem core with (1-hydroxyethyl) substituent, fused β-lactam to pyrroline with CO₂⁻, attached to phenyl ring (positions 1-4) bearing $R^{a1}$ at position 1, NHR³ at position 3-adjacent, and at position 3 another aryl group with atoms 5, 6, N⁺7(Rʸ), 8 and $R^{a3}$ at 6, $R^{a2}$ at 8]

$R^{a2}$ represents H

| $R^{a1}$ | $R^3$ | $R^Y$ | $R^{a3}$ |
|---|---|---|---|
| Br | H | CH₃ | —CH₂-N⁺(=CH-CH=CH-CH=)N—CH₃ Cl⁻ (imidazolium) |
| Br | CH₃ | CH₃ | —CH₂-N⁺(=CH-CH=CH-CH=)N—CH₃ Cl⁻ |
| SMe | H | CH₃ | —CH₂-N⁺(=CH-CH=CH-CH=)N—CH₃ Cl⁻ |
| SMe | CH₃ | CH₃ | —CH₂-N⁺(=CH-CH=CH-CH=)N—CH₃ Cl⁻ |
| SO₂CH₃ | H | CH₃ | —CH₂-N⁺(=CH-CH=CH-CH=)N—CH₃ Cl⁻ |
| SO₂CH₃ | CH₃ | CH₃ | —CH₂-N⁺(=CH-CH=CH-CH=)N—CH₃ Cl⁻ |
| CONH₂ | H | CH₃ | —CH₂-N⁺(=CH-CH=CH-CH=)N—CH₃ Cl⁻ |
| CONH₂ | CH₃ | CH₃ | —CH₂-N⁺(=CH-CH=CH-CH=)N—CH₃ Cl⁻ |
| CN | H | Absent | —CH₂—N⁺(CH₃)(—CH₂CH₂—)₂N⁺—Me₂ Cl⁻ (piperazinium) |
| CN | CH₃ | Absent | —CH₂—N⁺(CH₃)(—CH₂CH₂—)₂N⁺—Me₂ Cl⁻ |
| Br | H | Absent | —CH₂—N⁺(CH₃)(—CH₂CH₂—)₂N⁺—Me₂ Cl⁻ |
| Br | CH₃ | Absent | —CH₂—N⁺(CH₃)(—CH₂CH₂—)₂N⁺—Me₂ Cl⁻ |
| SMe | H | Absent | —CH₂—N⁺(CH₃)(—CH₂CH₂—)₂N⁺—Me₂ Cl⁻ |

TABLE 5-continued
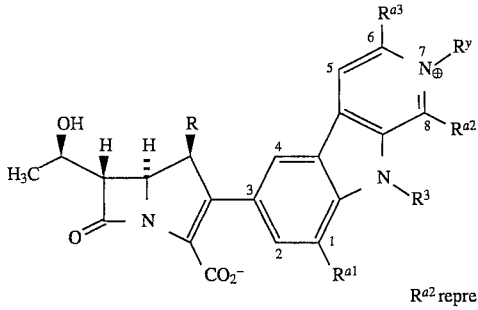
$R^{a2}$ represents H
| $R^{a1}$ | $R^3$ | $R^Y$ | $R^{a3}$ |
|---|---|---|---|
| SMe | CH₃ | Absent | 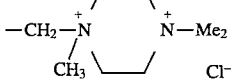 |
| SO₂Me | H | Absent | 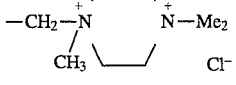 |
| SO₂Me | CH₃ | Absent | 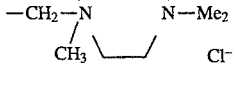 |
| CONH₂ | H | Absent | 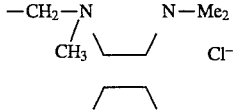 |
| CONH₂ | CH₃ | Absent | 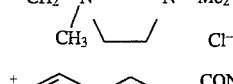 |
| CN | H | CH₃ | 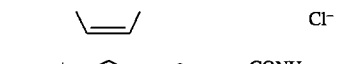 |
| CN | CH₃ | CH₃ | 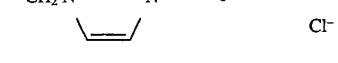 |
| Br | H | CH₃ | 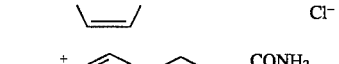 |
| Br | CH₃ | CH₃ | 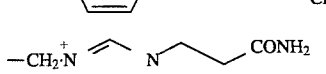 |
| SMe | H | CH₃ | 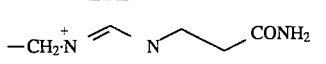 |
| SMe | CH₃ | CH₃ | 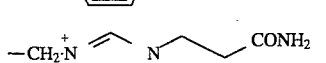 |
| SO₂Me | H | CH₃ | 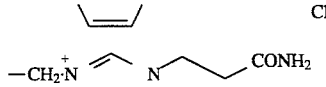 |
| SO₂Me | CH₃ | CH₃ | 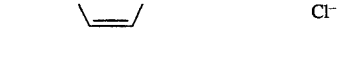 |

TABLE 5-continued

[Structure shown with $R^{a2}$ represents H]

| $R^{a1}$ | $R^3$ | $R^Y$ | $R^{a3}$ |
|---|---|---|---|
| $CONH_2$ | H | $CH_3$ | $-CH_2\overset{+}{N}$⟨imidazole⟩$N$-$CH_2CH_2CONH_2$  $Cl^-$ |
| $CONH_2$ | $CH_3$ | $CH_3$ | $-CH_2\overset{+}{N}$⟨imidazole⟩$N$-$CH_2CH_2CONH_2$  $Cl^-$ |
| CN | H | $CH_2CH_3$ | $-CH_2\overset{+}{N}$⟨imidazole⟩$N$-$CH_2CH_2CONH_2$  $Cl^-$ |
| CN | $CH_3$ | $CH_2CH_3$ | $-CH_2\overset{+}{N}$⟨imidazole⟩$N$-$CH_2CH_2CONH_2$  $Cl^-$ |
| Br | H | $CH_2CH_3$ | $-CH_2\overset{+}{N}$⟨imidazole⟩$N$-$CH_2CH_2CONH_2$  $Cl^-$ |
| Br | $CH_3$ | $CH_2CH_3$ | $-CH_2\overset{+}{N}$⟨imidazole⟩$N$-$CH_2CH_2CONH_2$  $Cl^-$ |
| SMe | H | $CH_2CH_3$ | $-CH_2\overset{+}{N}$⟨imidazole⟩$N$-$CH_2CH_2CONH_2$  $Cl^-$ |
| SMe | $CH_3$ | $CH_2CH_3$ | $-CH_2\overset{+}{N}$⟨imidazole⟩$N$-$CH_2CH_2CONH_2$  $Cl^-$ |
| $SO_2Me$ | H | $CH_2CH_3$ | $-CH_2\overset{+}{N}$⟨imidazole⟩$N$-$CH_2CH_2CONH_2$  $Cl^-$ |
| $SO_2Me$ | $CH_3$ | $CH_2CH_3$ | $-CH_2\overset{+}{N}$⟨imidazole⟩$N$-$CH_2CH_2CONH_2$  $Cl^-$ |
| $CONH_2$ | H | $CH_2CH_3$ | $-CH_2\overset{+}{N}$⟨imidazole⟩$N$-$CH_2CH_2CONH_2$  $Cl^-$ |
| $CONH_2$ | $CH_3$ | $CH_2CH_3$ | $-CH_2\overset{+}{N}$⟨imidazole⟩$N$-$CH_2CH_2CONH_2$  $Cl^-$ |

[1] When $R^y$ is absent the N atom at position 7 is non-quaternary.

When a functional group is "protected" or "blocked", this means that the group is in modified form to preclude undesired side reactions at the protected site. Suitable protecting groups for the compounds of the present invention will be recognized from the present application taking into account the level of skill in the art, and with reference to standard textbooks, such as McOmie, J. (ed) *Protecting Groups in Organic Chemistry* pp. 46–119 (1973).

In the preparation methods described herein, the carboxyl group at the 3-position and the hydroxyl group at the 8-position of the carbapenem can remain blocked until the final product is prepared. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable hydroxyl and carboxyl protecting groups are known in the art. See, e.g., T. W. Greene, *Protective Groups in Organic Synthesis*, John Wiley & Sons, Inc., 1981 (Chapters 2 and 5).

The compounds of the invention and those shown in the reaction schemes are electronically balanced. Since a quaternary or bisquaternary ammonium group is often present, one or two negatively charged counterions $X^-$ and $Z^-$ are also present when appropriate to provide overall electronic balance.

In some of the final compounds, the charge of the bisquaternary ammonium group is balanced by a negatively charged counterion, $X^-$, in conjunction with the negatively charged carboxylate, $CO_2-$, which is contained in the molecule. Counterion $X^-$ is a pharmaceutically acceptable anionic species. The desired counterion $X^-$ may be introduced by standard techniques as described above. It is understood that when the counterion $X^-$ is an anionic species possessing more than one negative charge, then an appropriate amount of $X^-$ is present to result in overall electronic balance in the final compound I. For example, when $X^-$ is a dianionic species, then one-haft of a molar equivalent of $X^-$ is present relative to the carbapenem moiety. Suitable negatively charged counterions, $X^-$, are listed below under the description of pharmaceutically acceptable salts.

The pharmaceutically acceptable salt forms of the carbapenem compound of formula I mentioned above refer to the various possibilities for the charge balancing counterion $X^-$. Anions derived from inorganic or organic acids are suitable. Representative examples of such counterions are the following: acetate, adipate, aminosalicylate, anhydromethylenecitrate, ascorbate, aspartate, benzoate, benzenesulfonate, bisulfate, bromide, titrate, camphorate, camphorsulfonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate/diphosphate, polygalacturonate, propionate, salicylate, stearate, succinate, sulfate, tartrate, tosylate and undecanoate. Other anionic species will be apparent to the ordinarily skilled chemist.

The carbapenem compounds of the present invention are useful in various pharmaceutically acceptable salt forms for the treatment of bacterial infections in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is concerned with pharmaceutical compositions and methods of treating bacterial infections utilizing the carbapenem compound of formula I.

The compound of the invention may be used in a variety of pharmaceutical preparations. Compositions for injection, the preferred route of delivery, may be prepared in unit dosage form in ampoules or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the active ingredient may be in the form of a powder, which can be reconstituted with a suitable carrier such as sterile water, normal saline and the like at the time of administration. The powder can be in lyophillized or non-lyophillized form.

Oral compositions are typically in the form of tablets, capsules, solutions or suspensions. Such compositions may likewise be packaged in unit dose or multidose containers. In these oral compositions, the pharmaceutically acceptable carriers may be comprised of diluents, tabletting and granulating aids, lubricants, disintegrants, buffers, sweeteners, preservatives and the like.

Topical applications may be formulated with a pharmaceutically acceptable carrier in the form of hydrophobic or hydrophilic ointments, creams, lotions, solutions, paints or powders.

The dosage to be administered depends to a large extent upon the condition and size of the subject being treated as well as the route and frequency of administration. The parenteral route (by injection) is preferred for generalized infections. Such matters, however, are typically left to the discretion of the clinician according to principles of treatment well known in the antibacterial arts.

The compositions for human delivery per unit dosage, whether liquid or solid, may contain from about 0.01% to about 99% of active material, the preferred range being from about 10–60%. The composition will generally contain from about 15 mg to about 2000 mg of the active ingredient; however, in general, it is preferable to employ a dosage amount in the range of from about 250 mg to 1000 mg. In parenteral administration, the unit dosage is usually the compound I in a sterile water or saline solution or in the form of a soluble powder intended for solution.

The preferred method of administration of the compound of formula I is parenterally by intravenous (i.v.) infusion. Alternatively, the compound may be administered intramuscularly (i.m.).

For adults, a dose of about 5 to about 50 mg of the formula I antibacterial compound per kg of body weight is administered from 1 to 6 times per day. The preferred dosage ranges from about 250 mg to 1000 mg of the compound given one to four times per day.

More specifically, for mild infections a dose of 250 mg two to four times daily is preferred. For moderate infections against highly susceptible gram positive organisms a dose of 500 mg b.i.d. to q.i.d. is preferred. For severe, life-threatening infections against organisms at the upper limits of sensitivity to the antibiotic, a dose of about 1000–2000 mg two to six times daily is preferred.

For children, a dose of 5–25 mg/kg of body weight given 1 to 4 times per day is preferred; a dose of 10 mg/kg b.i.d., q.i.d. or q.i.d. is recommended.

The compounds of formula I are of the broad class known as carbapenems. Naturally occuring carbapenems are susceptible to attack by a renal enzyme known as dehydropeptidase (DHP). This attack or degradation may reduce the efficacy of the carbapenem antibacterial agent. The compound of the present invention is significantly less subject to such attack, and therefore may not require the use of a DHP inhibitor. However, such use is optional and contemplated to be part of the present invention. Inhibitors of DHP and their use with carbapenem antibacterial agents are disclosed in European Patent Applications No. 79102616.4, filed Jul. 24, 1979 (Patent No. 0 007 614); and No. 82107174.3, filed Aug. 9, 1982 (Publication No. 0 072 014).

The compounds of the present invention may, where DHP inhibition is desired or necessary, be combined or used with the appropriate DHP inhibitor as described in the aforesaid patents and published application. The cited European Patent Application defines the procedure for determining DHP susceptibility of the present carbapenems and disclose suitable inhibitors, combination compositions and methods of treatment.

A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The compounds of the present invention are active against various gram-positive and in some cases gram-negative bacteria, and accordingly find utility in human and veterinary medicine. The compounds are potent anti-MRSA/MRCNS compounds.

Syntheses of compounds of Formula I may be carried out in multi-stage schemes followed by the removal of any protecting groups. The objective of the first stage is to produce a base carboline compound which may be convened to the two- position substituent of the carbapenem. The objective of the second stage is to attach the carboline to the base carbapenem. Finally, the objective of the third stage is to substitute the carboline with the desired Ra group or groups. This third stage may be performed during or after the first or second stages, according to the nature of the various $R^a$ substituents.

STAGE 1 SYNTHESIS

Schemes A–G demonstrate suggested first stage syntheses for the carboline ring system. A general route, outlined in Scheme A, involves the preparation of a suitably substituted and functionalized pyridine compound A-3 or A-8 which contains the functional group needed to form the pyrrolidine ring of the desired carboline ring system, as well as other substituent groups, and the functionality needed for coupling to the carbapenem. Generally, the appropriately attached nitro group is converted to a primary mine, and thereafter cyclized to produce the carboline. By altering the substitution pattern on A-1 and A-2, such as in A-6 or A-7, different carbolines can be obtained and used herein.

Scheme B provides alternative methods for both functionalizing the carboline ring system and substituting on the central carboline ring nitrogen. In contrast to Scheme A, in which the bromine functionality is present in the starting materials prior to carboline formation, the bromine atom can be introduced into the desired position by direct bromination of the carboline ring system as described by K. L. Rinehart, et al. *J, Amer. Chem. Soc.* 1987, 109, 3378. The N-unsubstituted carboline B-2 is treated with sodium hydride and an appropriate methylating agent to provide B-3.

The reactions of Schemes C, D, F and G provide for further substitution and functionalization on the carboline platform prior to attachment to the carbapenem nucleus.

In Scheme C, the bromine functional group is first converted into the requisite trimethyl stannyl functional group and then the nitrogen atom in the six membered ring of compound C-2 or C-5, is quaternized upon reaction with $R^yOTf$, providing C-3 or C-6, respectively, thereby converting N to $N^+R^y$ and generating the triflate anion.

Similarly, in Scheme D, the nitrogen atom in C-1 or C-2 is converted to an N-oxide, D-2 or D-5, by reaction with m-chloroperbenzoic acid before or after introduction of the organostannane functionality.

In Scheme E, the carbolinyl N-oxide E-1 can be methylated to produce the N-methoxide E-2.

Schemes F and G depict synthetic sequences which allow for the introduction of substituents $R^a$. Thus, after N-methoxylation to produce F-2 and G-2, the carboline is treated with KCN to produce F-3 and G-3, respectively, which is thereafter acidified to produce the carboxylic acid G-5. The carboxylic acid can thereafter undergo esterification to produce G-6 and reduction to produce the carboline alkanol G-7. Stannylation provides G-8.

STAGE 2 SYNTHESIS

Schemes H, I, J and K address linkage of the carboline platform to the carbapenem nucleus.

The steps for preparing the 2-oxocarbapenam intermediate, H-1, are well known in the art and are explained in ample detail by D. G. Melillo, et al., *Tetrahedron Letters*, 21, 2783 (1980), T. Salzmann et al., *J. Am. Chem. Soc.*, 102, 6161 (1980), and L. M. Fuentes, et al. *J. Am. Chem. Soc.*, 108, 4675 (1986). The syntheses are also disclosed in U.S. Pat. Nos. 4,269,772, 4,350,631, 4,383,946 and U.S. Pat. No. 4,414,155 all assigned to Merck and Co., Inc.

The second stage synthesis, involving attachment of the carboline platform to the 2-position of the carbapenem, includes a palladium catalyzed cross-coupling reaction between the carbapenem trillate H-2 and a suitably substituted arylstannane C-2, C-3, C-5, C-6, D-3, D-5, E-2, F4 or G-8.

In Schemes H, I, K and L, the 2-oxocarbapenam H-1 is reacted with a suitable trifluoromethanesulfonyl source, such as trifluoromethane-sulfonic anhydride, trifluoromethanesulfonyl chloride and the like, in the presence of an organic nitrogen base, such as triethylamine, diisopropylamine and the like, in a polar aprotic solvent, such as tetrahydrofuran to provide the triflate intermediate H-2. Optionally as depicted in Schemes I, J, K and L, an organic nitrogen base, such as triethylamine or the like, is added to the reaction solution, followed by a silylating agent, such as trimethylsilyl or triethylsilyl trifluoro-methanesulfonate to provide the triflate intermediate I-1. In either instance, intermediates H-2 or I-1 is then processed by the addition of an aprotic polar coordinating solvent, such as DMF, 1-methyl-2-pyrrolidinone or the like. This is followed by the addition of a palladium compound, such as tris(dibenzylideneacetone)dipalladium-chloroform, palladium acetate and the like, optionally a suitably substituted phenylphosphine, such as tris(4-methoxyphenyl)phosphine, tris(2,4,6-trimethoxyphenyl)phosphine and the like, and the stannane C-2, C-3, D-3, D-5, E-2, F-4, G-8 or L-1. A metal halide, such as lithium chloride, zinc chloride and the like, can be added and the reaction solution is warmed to a suitable temperature, such as 0° C. to 50° C., and allowed to stir for a suitable amount of time such as from a few minutes to 48 hours. The carbapenem H-3, I-2, J-1 or K-1 is thereafter obtained by conventional isolation/purification techniques known in the art.

Schemes I, J, K and L address deprotection of the hydroxyethyl side chain at position 6, and the carboxylate group at position 3, which is detailed further below.

STAGE 3 SYNTHESIS

Scheme K addresses the coupling of the carbapenem and carboline groups, in a manner suitable for enabling further substitution s onto the distal ring. Final elaboration of $R^a$ from the immediate precursor may be accomplished by this scheme, which addresses a representative one step process for introducing the Type Ia cationic substituent, utilizing 2.5 equivalents of a nucleophilic nitrogen base to generate the triflate and undergo nucleophilic substitution. Thus, the hydroxymethyl side chain of K-1 can be reacted ill situ with triflic anhydride and N-methylimidazole to produce the methylimidazolium triflate salt K-2, which is then deprotected to produce K-3.

By modifying the position of the hydroxymethyl group on the carboline, or by modifying the group itself, different $R^a$ substituents can be included. In Scheme L, L-2 provides variation in the placement of the hydroxymethyl group.

Generally speaking, the milder conditions of the synthesis allow for a wider range of functional groups $R^a$ to be present when attaching the carboline. However, in certain cases it is advantageous for the $R^a$ substituent(s) of the stannane to be introduced in a protected or precursor form. Elaboration of $R^a$ from a precursor substituent, e.g. hydroxymethyl, is followed by removal of any protecting groups on the Ra substituent, to then provide the final compound of Formula I.

An alternate procedure includes a two step activation of the as hydroxymethyl substituent which is depicted in Scheme L. In this instance, the hydroxyl group is first convened into the corresponding mesylate group utilizing the procedure of Crossland, et al., *J. Org. Chem.* 1970, 35, 3195, which in turn is transformed into the more activated iodide leaving group via a Finkelstein reaction with sodium iodide. Displacement of the iodide is then performed with about 1–2 equivalents of a nitrogen based heterocyclic or heteroaromatic nucleophile to provide the penultimate intermediate, L-3. Deprotection reactions provide the antibiotic types L-4.

In the preparation methods described above, the carboxyl group at the 3-position and the hydroxyl group at the 8-position of the carbapenem typically remain blocked by protecting groups until the final product is prepared. Deblocking may be carded out in a conventional manner. For compounds prepared according to Schemes I–L, deprotection may be carded out first by desilylation using aqueous acidic conditions, such as acetic acid or dilute HCl or the like, in an organic solvent, such as THF, at 0°–50° C., for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$, or buffer such as sodium hydrogen phosphate and a catalyst, such as 10% Pd/C or 5% Rh/C, followed by hydrogenation provides for the removal of the p-nitrobenzyl protecting group and the formation of the final compound of formula I.

SCHEME A

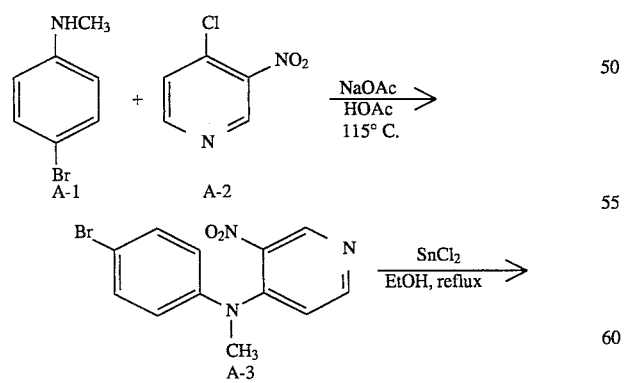

-continued
SCHEME A

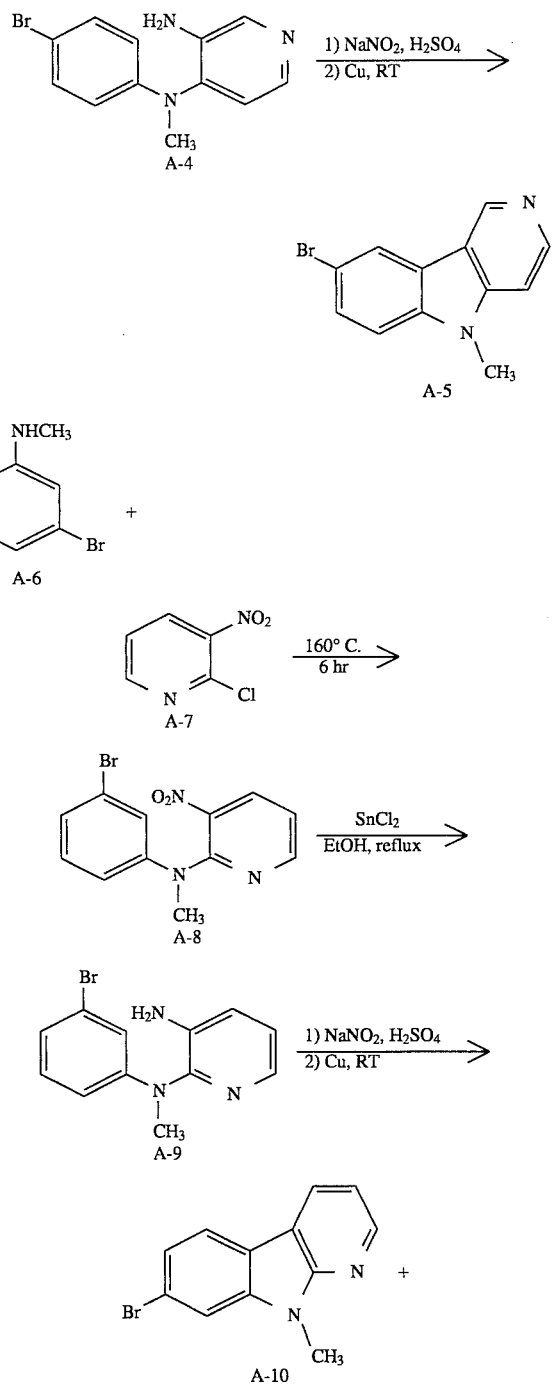

-continued
SCHEME A

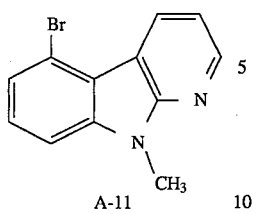

A-11

SCHEME B

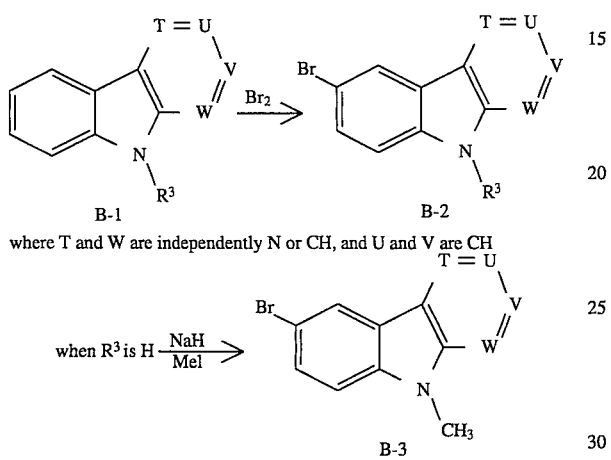

where T and W are independently N or CH, and U and V are CH

SCHEME C

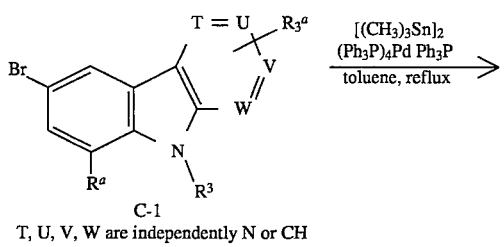

C-1
T, U, V, W are independently N or CH

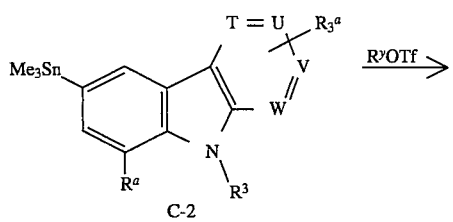

C-2

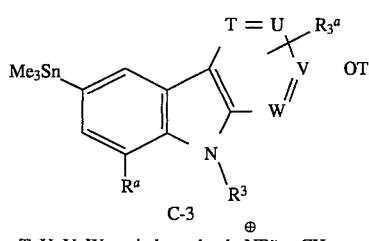

C-3
T, U, V, W are independently NR$^y$ or CH
R$^a$, R$^y$, and R$^3$ are as defined -continued
SCHEME C

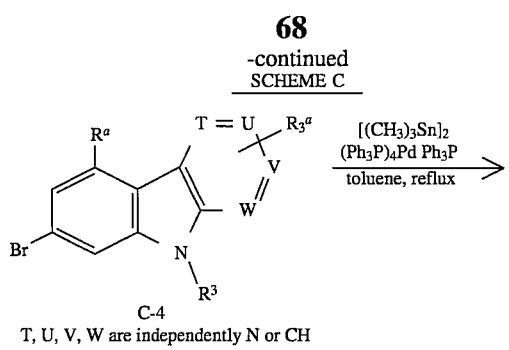

C-4
T, U, V, W are independently N or CH

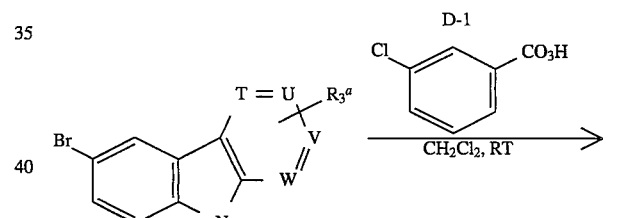

C-5

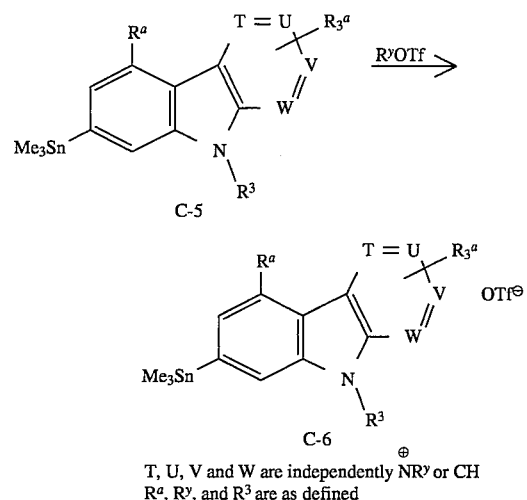

C-6
T, U, V and W are independently NR$^y$ or CH
R$^a$, R$^y$, and R$^3$ are as defined

SCHEME D

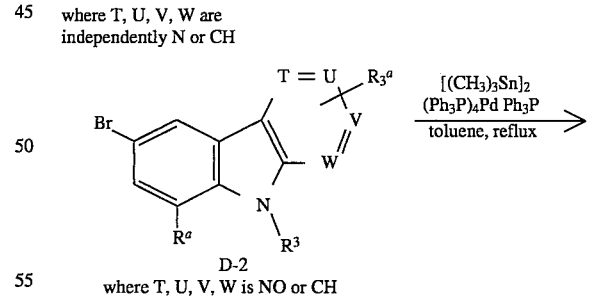

D-2
where T, U, V, W is NO or CH

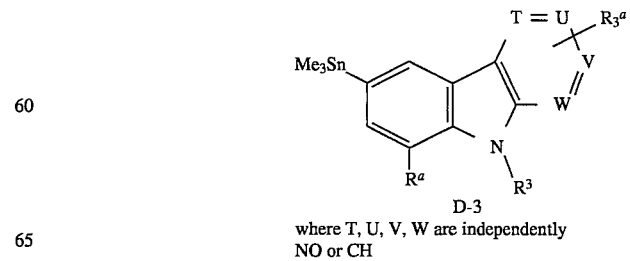

D-3
where T, U, V, W are independently NO or CH

-continued
SCHEME D
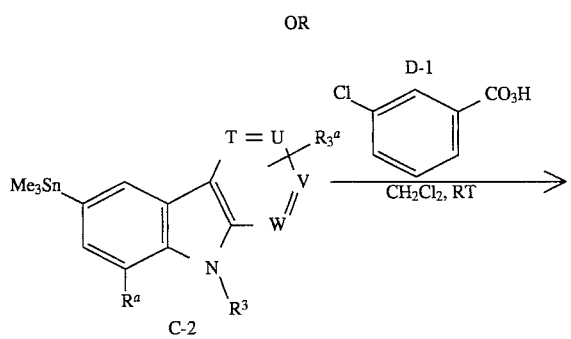
C-2
where T, U, V, W are independently N or CH
OR
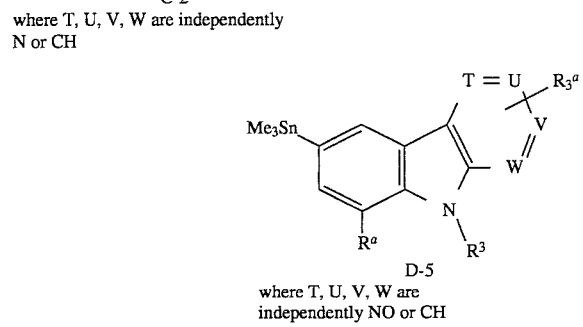
D-5
where T, U, V, W are independently NO or CH
SCHEME E
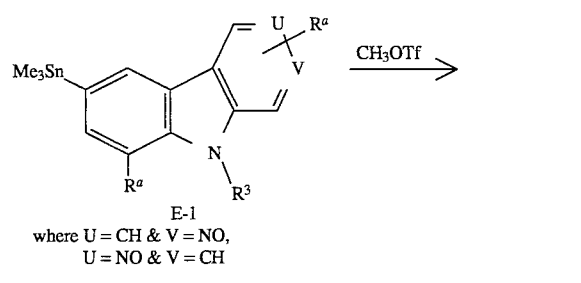
E-1
where U = CH & V = NO,
U = NO & V = CH
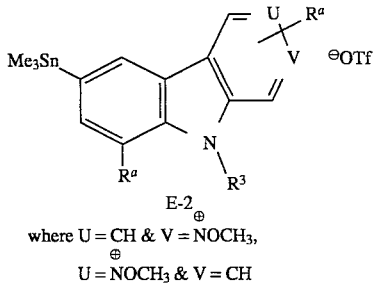
E-2
where U = CH & V = N⊕OCH₃,
U = N⊕OCH₃ & V = CH
SCHEME F
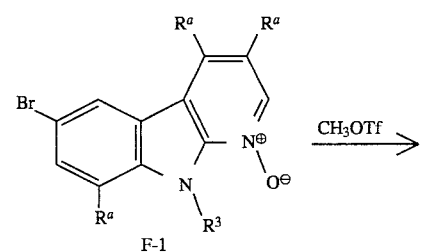
F-1
SCHEME F -continued
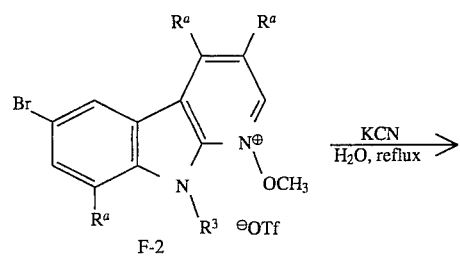
F-2
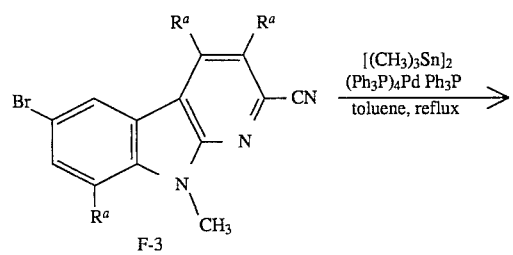
F-3
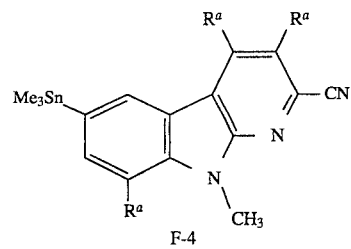
F-4
SCHEME G
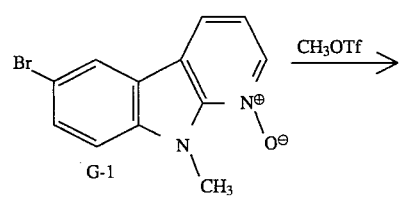
G-1
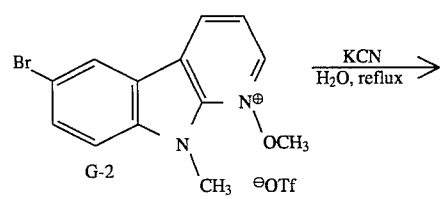
G-2
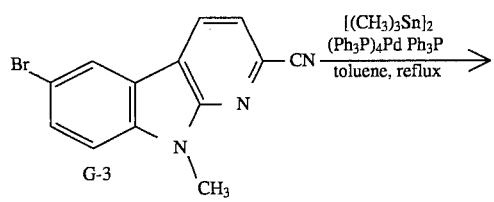
G-3
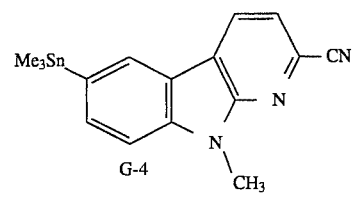
G-4

71
-continued
SCHEME G
72
-continued
SCHEME G
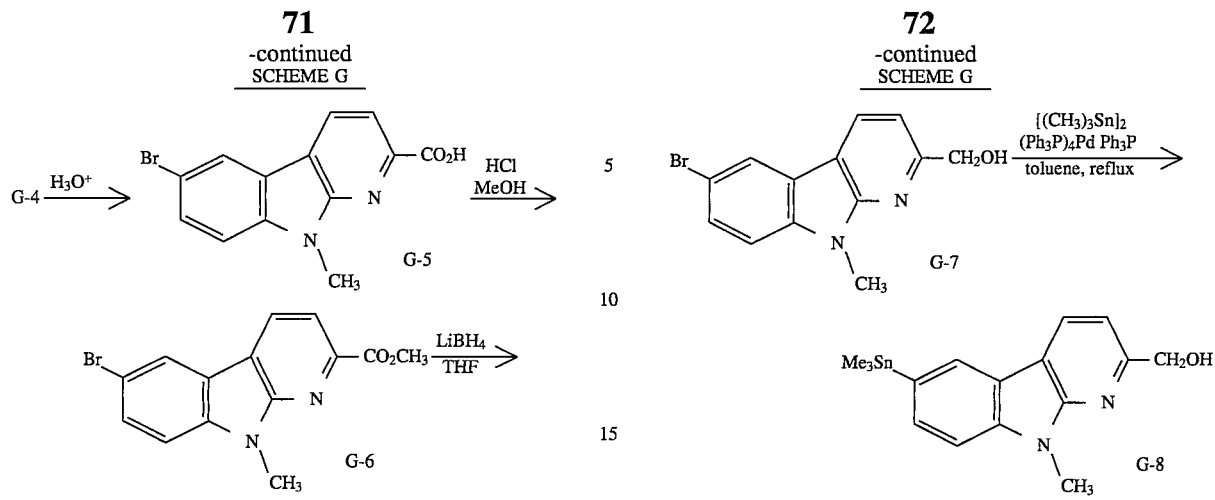
SCHEME H
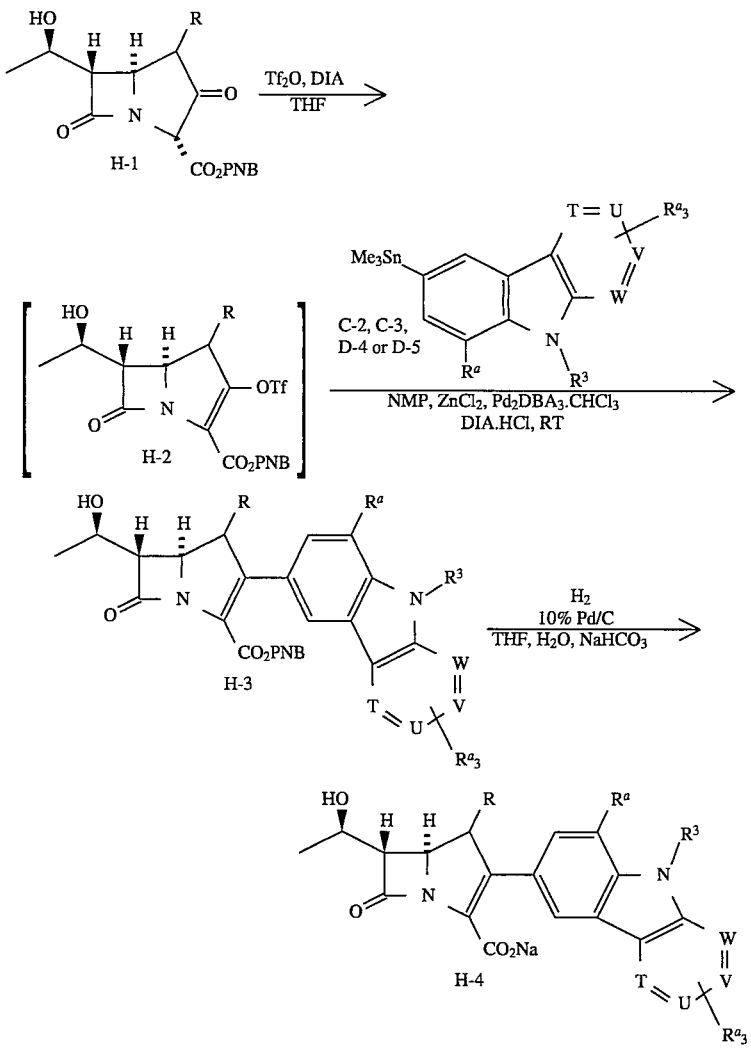
R, $R^a$, and $R^3$ are as defined
T, U, V, W are independently N or CH
$Tf_2O$ is triflic anhydride
NMP is N-methylpyrrolidinone
DIA is diisopropylamine
PNB is p-nitrobenzyl
DBA is dibenzylideneacetone

SCHEME I
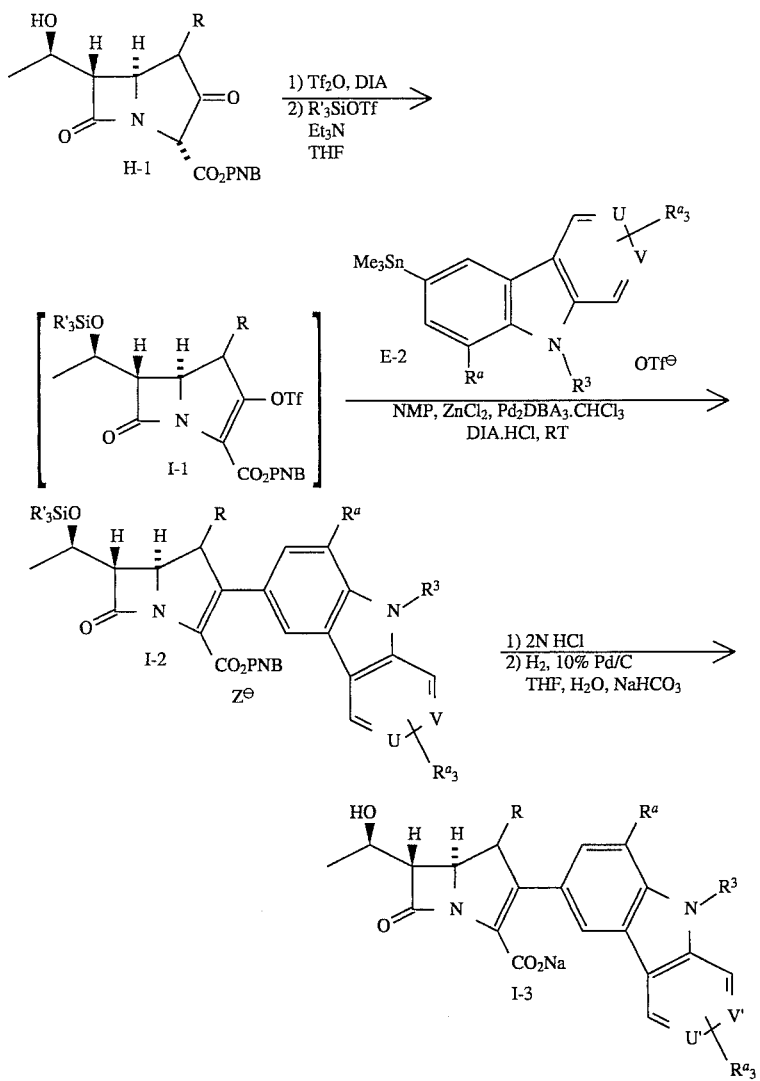
U and V are independently NOCH$_3$ or CH.
U' and V' are independently N or CH
Z is Cl or OTf    R' is CH$_3$ or CH$_3$CH$_2$
SCHEME J
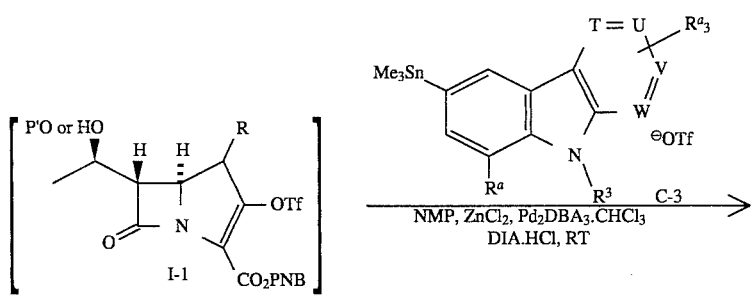

-continued
SCHEME J
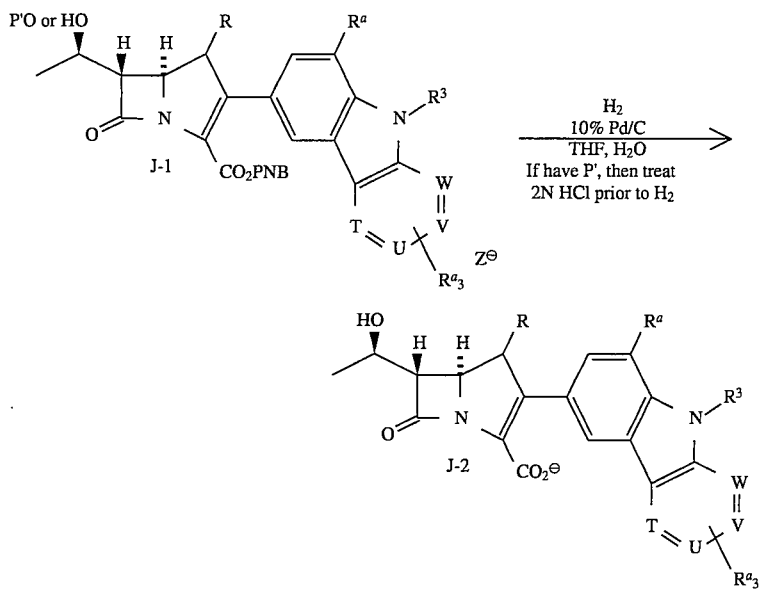
T, U, V, W are independently $\overset{\oplus}{N}R^y$ or CH
SCHEME K
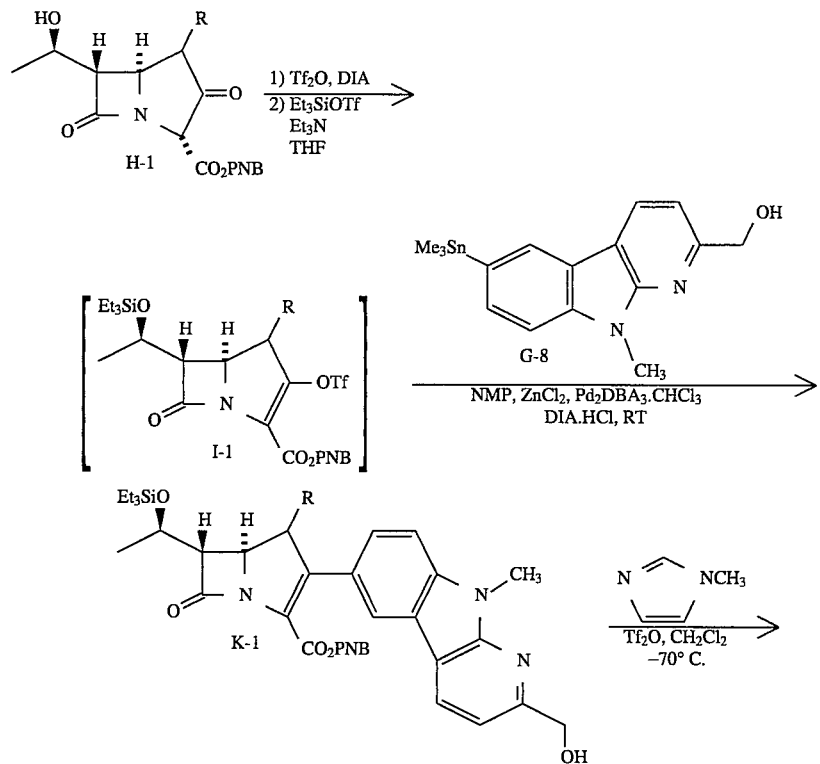

-continued
SCHEME K
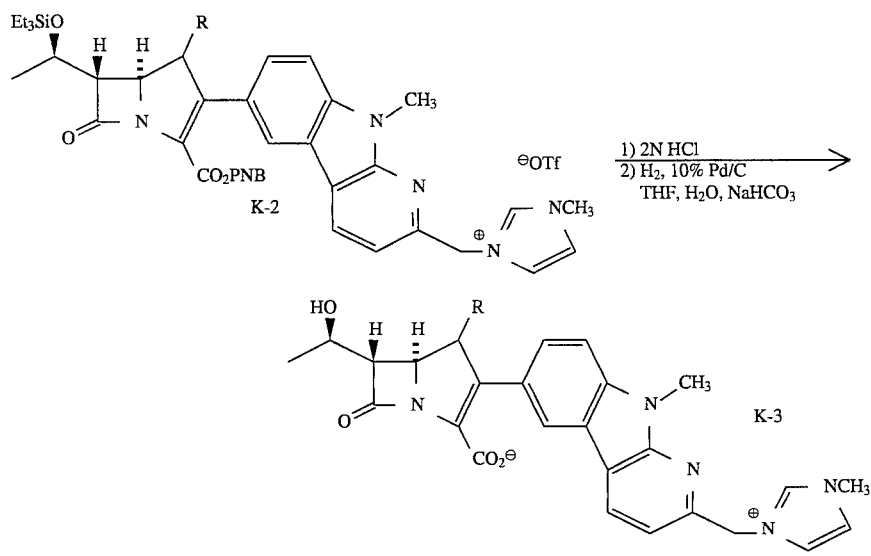
SCHEME L
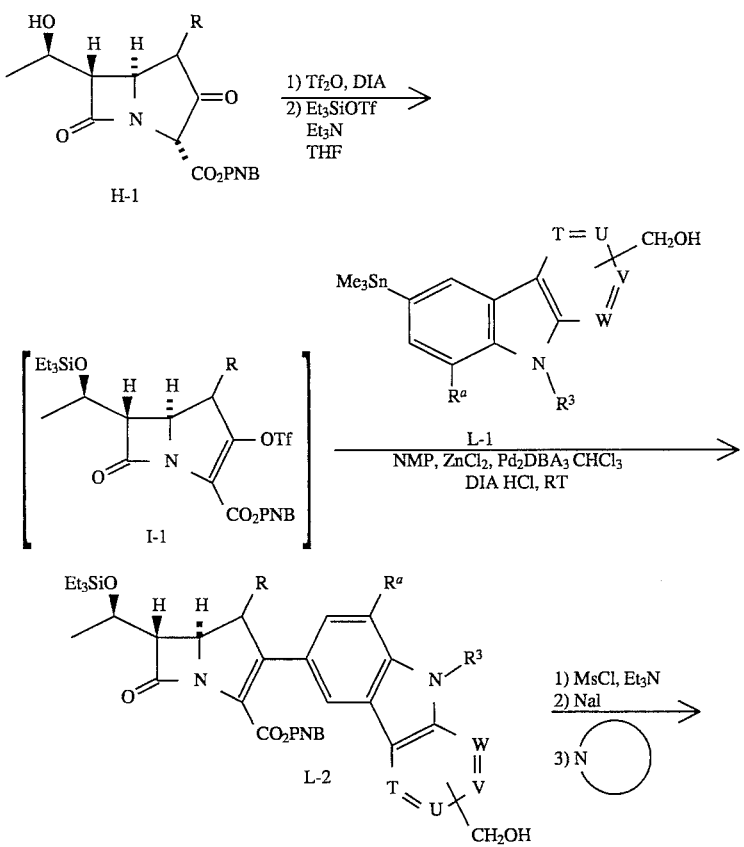

-continued
SCHEME L

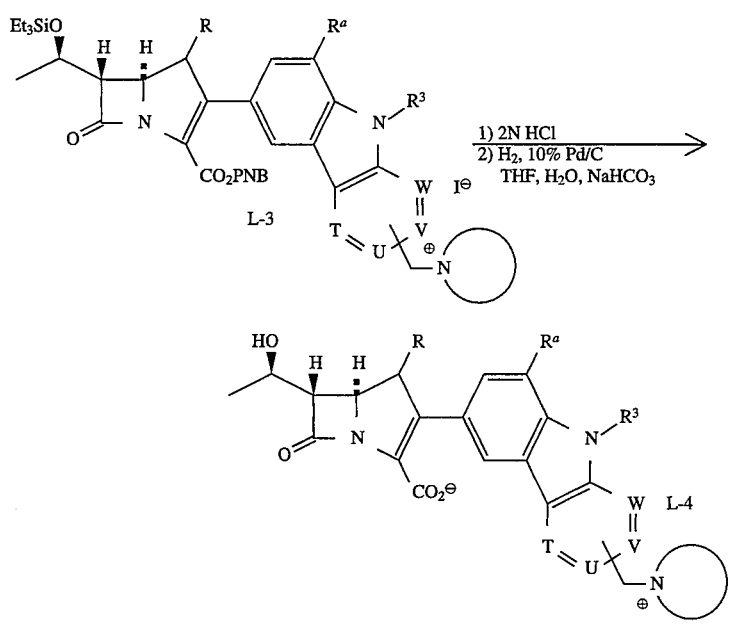

T, U, V, W are independently CH or N

The invention is further described in connection with the following non-limiting examples.

EXAMPLE 1

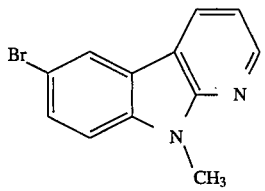

6-Bromo-9-methyl-α-carboline (1)

To a solution of 2.25g (12.3mmol) of 9-methyl-α-carboline in 170ml of THF was added dropwise 1.27mL (24.6mmol) of bromine. After stirring 2 h at room temperature the reaction was treated with 10% aq. $Na_2S_2O_3$. The organic layer was separated and evaporated to a residual oil which was dissolved in EtOAc and washed subsequently with 10% aq. $Na_2CO_3$, brine and dried ($MgSO_4$). Purification on a silica gel column (gradient elution 5 to 30% EtOAc in hexanes) gave 2.16 g of 1, as a light tan solid.

IR: 1767 (β-lactam C=O), 1715 (ester C=O); $^1H$ NMR ($CDCl_3$): δ: 3.96 (s, 3H, N—$CH_3$), 7.20 (dd, 1H, H-3, $J_{2-3}$=2.5 Hz, $J_{3-4}$=4 Hz), 7.36 (d, 1H, H-8, $J_{7-8}$=4 Hz), 7.63 (dd, 1H, H-7, $J_{7-8}$=4 Hz), 8.20 (d, 1H, H-5, $J_{5-7}$=1 Hz) 8.29 (dd, 1H, H-4, $J_{3-4}$=4Hz), 8.53 (dd, 1H, H-2, $J_{2-3}$=2.5 Hz); ms:(FAB) m/e (M+1) 261, 263.

EXAMPLE 2

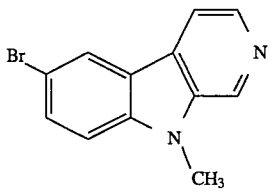

6-Bromo-9-methyl-β-carboline (2)

A solution of 6-bromo-β-carboline (1.0 g, 4.05 mmol) in 12 mL of DMF was stirred in an ice bath and 186 mg (4.65 mmol, 1.15 equiv.) of 60% sodium hydride in mineral oil dispersion was added. Gas evolution was observed and stirring was continued for 1 h at ambient temperature. The homogenous reaction was partitioned between EtOAc and $H_2O$. The organic layer was washed again with $H_2O$ followed by brine. After drying ($MgSO_4$), evaporation gave a pale yellow solid.

ms:(FAB) m/e (M+1)261, 263.

EXAMPLE 3

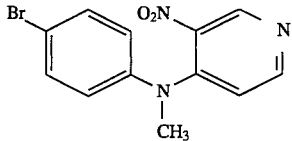

N-methyl-p-bromo-N-(2-nitro-4'-pyridyl)aniline (3)

p-Bromo-N-methylaniline (186 mg, 1.0 mmol) and 4-chloro-3-nitropyridine (158 mg, 1.0 mmol) in 4 mL of acetic acid was treated with 164 mg (2.0 mmol) of sodium acetate and heated at 115° C. for 15 min. The cooled reaction was diluted with H₂O, neutralized with ammonium hydroxide, and extracted with EtOAc. The organic layer was washed with 1N NaOH, dried (MgSO₄) and concentrated to a residual solid. Purification on a silica gel column (3:7 EtOAc:hexane) provided 175 mg of 3 as an orange solid.

ms:(FAB) m/e (M+1)308, 310.

EXAMPLE 4

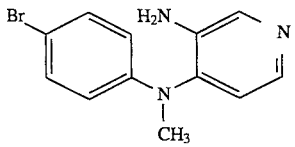

N-methyl-p-bromo,N-(2-amino-4'-pyridyl)aniline (4)

A mixture of the nitro compound 3 (1.0 g, 3.25 mmol) and 2.2 g (9.75 mmol) of stannous chloride dihydrate in 25 mL of absolute ethanol was heated at reflux for 1 h. The ethanol was evaporated and the residual material was partitioned between EtOAc and 5N NaOH. The organic layer was washed with H₂O and brine, then dried (MgSO₄), and concentrated to a residual oil. Purification on a silica gel column (1:1 EtOAc:hexanes) gave 651 mg of 4 as a tan solid.

ms:(FAB) m/e (M+1)278, 280.

EXAMPLE 5

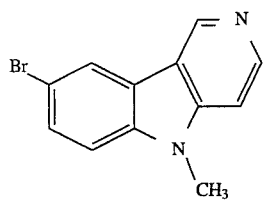

6-Bromo-9-methyl-γ-carboline (5)

A solution of the amine 4 (2.45 g, 8.8 mmol) and 3.7 mL of concentrated sulfuric acid in 45 mL of H₂O was cooled in an ice bath. Sodium nitrite (1.82 g, 26.4 mmol) in 20 mL of H₂O was added dropwise. After 30 min, 1.3 g of urea was added to decompose the excess nitrous acid. After foaming had subsided (5 min), copper powder was added in portions. Stirring under nitrogen was continued for 2 h at room temperature after which time the suspension was basified with ammonium hydroxide and extracted with EtOAc. The organic layer was dried (MgSO₄) and evaporated to a brown residual solid. Purification on a silica gel column (EtOAc) provided 1.54 g of 5.

ms:(FAB) m/e (M+1)261, 263.

EXAMPLE 6

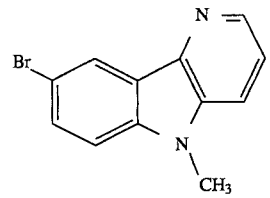

6-Bromo-9-methyl-δ-carboline (6)

9-methyl-δ-carboline Was treated with bromine as in Example 1 to give 6.

ms:(FAB) m/e (M+1)261, 263.

EXAMPLE 7

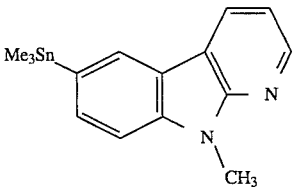

6-(Trimethylstannyl)-9-methyl-α-carboline (7)

A solution of 720 mg (2.76 mmol) of 1 in 28 mL of toluene was treated with 0.63 mL of hexamethylditin, 160 mg (0.138 mmol, 5% mol) of tetrakistriphenylphosphine-palladium and 22 mg (0.083 mmol, 3 mol %) of triphenylphosphine. A stream of nitrogen was bubbled into the solution for 5 min to deoxygenate the solvent. After heating at reflux for 1.25 h the cooled reaction was poured into EtOAc and washed subsequently with saturated NaHCO₃, H₂O and brine; dried (MgSO₄), and evaporated to a residual oil. Purification on a silica gel column (10% EtOAc in hexanes) gave 698 mg of 7 as a white solid.

¹H NMR (CDCl₃): δ: 0.34 (s, 9H, 3—CH₃), 3.96 (s, 3H, N—CH₃), 7.16 (dd, 1H, H-3), 7.46 (d, 1H, H-8), 7,62 (d, 1H, H-7), 8.18 (s, 1H, H-5), 8.33 (dd, 1H, H-4), 8.48 (dd, 1H, H-2).

EXAMPLE 8

The following carbolinyl stannanes were prepared according to the procedure outlined in Example 7.

6-Trimethylstannyl-9-methyl-β-carboline (8) was prepared from the bromide 2 to provide the desired product as a white solid.

6-Trimethylstannyl-9-methyl-γ-carboline (9) was obtained from the bromide 5 to give 9 as a white solid.

6-Trimethylstannyl-9-methyl-δ-carboline (10) was prepared from the bromide 6 to give 10.

6-Trimethylstannyl-9-methyl-1-oxo-α-carboline (12). Stannylation of 11 (see example 9) gave the desired product as a tan solid.

EXAMPLE 9

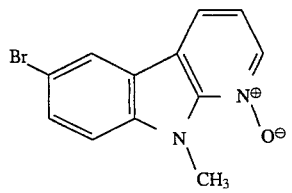

6-Bromo-9-methyl-1-oxo-α-carboline (11)

To a solution of the bromide I (2.61 g, 10 mmol) in 80 mL of dichloromethane was added 4.75 g (22 mmol) of m-chloroperoxybenzoic acid (80%). After stirring at room temperature overnight the reaction was treated with 5% sodium thiosulfate. The organic layer was isolated, washed with 10% sodium carbonate and brine, dried (MgSO₄), and concentrated to a tan solid. Purification through a small plug of silica gel with 10 to 20% EtOAc in methanol as eluent provided 1.70 g of 11 as a white solid.

EXAMPLE 10

In a fashion analogous to that of Example 9, the following N-oxides were prepared:
6-Trimethylstannyl-9-methyl-2-oxo-β-carboline (13) N-oxidation of the stannane 8 gave the desired product.
6-Trimethylstannyl-9-methyl-3-oxo-γ-carboline (14) was prepared from the stannane 9.

EXAMPLE 11

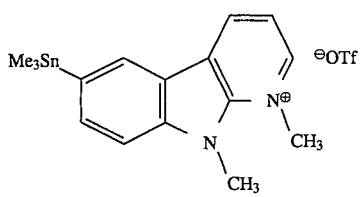

6-Trimethylstannyl-1,9-dimethyl-α-carbolinium triflate (15)

The aryl stannane 7 (80 mg, 0.23 mmol) was dissolved in 2 mL of dichloromethane and cooled in an ice bath. Methyl triflate (29 μL, 0.255 mmol) was added and the resultant solution was stirred for 1 h at 0° C., then warmed to room temperature and stirred overnight. The reaction was concentrated and the yellow solid was triterated with ether and collected by filtration to provide 92 mg of 15 as a yellow solid.

EXAMPLE 12

As described in Example 11, the following N-alkyl quaternary aryl stannanes were prepared.

6-Trimethylstannyl-2,9-dimethyl-β-carbolinium triflate (16)

N-methylation of the stannane 8 provided 16 as a yellow solid.
6-Trimethylstannyl-3,9-dimethyl-β-carbolinium triflate (17) was prepared from the stannane 9 to give the desired product as a yellow solid.
6-Trimethylstannyl-4,9-dimethyl-δ-carbolinium triflate (18) N-methylation of the stannane 10 provided 18 as a yellow solid.
6-Trimethyl-1-ethyl-9-methyl-α-carbolinium triflate (19) was obtained from the stannane 7 using 1.5 equivalents of ethyl triflate and stirring for 2 days at ambient temperature to yield 19.
6-Trimethylstannyl-9-methyl-2-methoxy-β-carbolinium triflate (20) was prepared from the stannane 13 to give 20 as a yellow solid.
6-Trimethylstannyl-9-methyl-3-methoxy-γ-carbolinium triflate (21) was obtained from the stannane 14 to provide the desired product as a white solid.
6-bromo-9-methyl-1-methoxy-α-carbolinium triflate (22). Methylation of the N-oxide 11 gave the product as a tan solid.

EXAMPLE 13

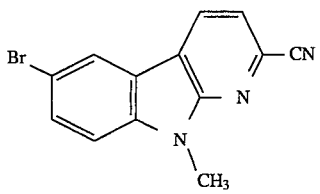

6-Bromo-2-cyano-9-methyl-α-carboline (23)

A suspension of 340 mg (0.79 mmol) of 22 in 10 mL of $H_2O$ was treated with a solution of 136 mg (2.09 mmol) of potassium cyanide in 1mL and then heated at reflux for 3 h. The cooled reaction was filtered and the white solid obtained was rinsed with $H_2O$ and dried to provide 143 mg (0.525 mmol) of 23.

IR: 2300 $cm^{-1}$ (CN).

ms: ($NH_3$/CI) m/e (M+1)288, 286.

EXAMPLE 14

As described in Example 7, the following stannylcarboline was prepared:

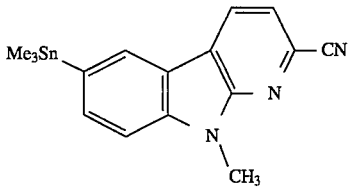

6-Trimethylstannyl-2-cyano-9-methyl-α-carboline (24) was prepared from 23 to give a white solid.

EXAMPLE 15

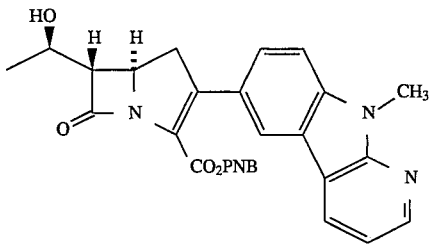

p-Nitrobenzyl-(5R,6S)-2-[6-(9-methyl-α-carbolinyl)]-6-[(1R)-1-hydroxyethyl]-carbapen-2-em-3-carboxylate The bicyclic β-keto ester (88 mg, 0.25 mmol) was dissolved in 1 mL of dry THF and cooled to −78° C. in a dry ice acetone bath. Diisopropylamine (39 μl, 0.28 mmol) was added and stirring was continued for 10 min during which a yellow color was noted. Triflic anhydride (39 μL, 0.28 mmol) was added and stirring at −78° C. was continued for another 20 min before addition of 1 mL of N-methylpyrrolidinone, 5 mg (0.005 mmol, 2 mol %) of $Pd_2(dba)_2 \cdot CHCl_3$, 97 mg (0.28 mmol) of the aryl stannane 7, and 35 mg (0.25 mmol) of diisopropylamine hydrochloride. The reaction was immediately warmed to room temperature. After 1.5 h the reaction was poured into EtOAc, washed three times with $H_2O$, followed by brine. After drying ($MgSO_4$), evaporation gave an oil which was taken up in a small volume of dichloromethane. Additon of ether effected precipitation of 25 as a white solid, 63.4 mg.

IR: cm$^{-1}$: 1767 (βlactam C=O), 1715 (ester C=O); $^1$H NMR (CDCl$_3$):δ: 1.41 (d, 3H, CH$_3$), 3.31 (dd, 1H, H-6), 3.41 (d, 2H, H-1),3.96 (s, 3H, N-CH$_3$), 4.33 (m, 2H, H-5, H-8), 5.29 (q, 2H, OCH$_2$), 7.18 (dd, 1H), 7.43 (m, 3H), 7.58 (dd, 1H), 8.05 (m, 3H), 8.22 (dd, 1H), 8.51 (dd, 1H).

EXAMPLE 15A

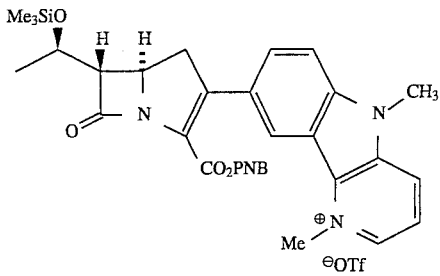

p-Nitrobenzyl-(5R,6S)-2-[6-(4,9-dimethyl-δ-carbolinium)]-6-[(1R)-1-trimethylsilyoxyethyl]-carbapen-2-em-3-carboxylate triflate (26)

To 68 mg (0.195 mmol) of β-ketoester in 0.8 mL of THF, cooled to −78° C., was added 30 μL of diisopropylamine (0.21 mmol) and a yellow color was noted. After 10 minutes triflic anhydride (36 μL, 0.21 mmol) was added and the mixture stirred for 20 minutes. Triethylamine (30 μL, 0.214 mmol) was added followed immediately by 41 μL (0.21 mmol) of trimethylsilyl triflate. After 20 minutes, the reaction was treated with 76 mg (0.15 mmol) of the stannane 18 dissolved in 0.8 mL of NMP, followed by 4 mg (0.0039 mmol, 2 mol%) of Pd$_2$(dba)$_3$CHCl$_3$ and 29.4 mg (0.21 mmol) of diisopropylamine hydrochloride. The reaction was warmed immediately to ambient temperature. After 2 h the reaction was poured into EtOAc and was washed three times with H$_2$O. The organic layer was dried over Na$_{2SO4}$ and concentrated to an amber oil. The oil was taken up in a small volume of CH$_2$Cl$_2$, and Et$_2$O was added to effect precipitation of 72.4 mg of the title compound as a yellow solid.

EXAMPLE 15B

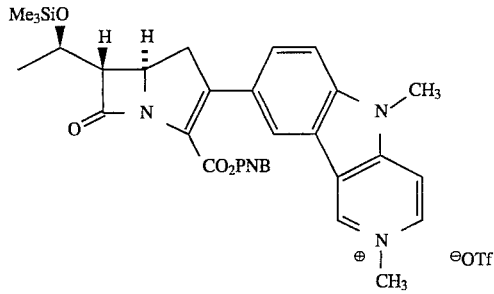

p-Nitrobenzyl-(5R,6S)-2-[6-(3,9-dimethyl-γ-carbolinyl)]-6-[(1R)-1-trimethlysilyloxyethyl]-carbapen-2-em-3-carboxylate (27)

Following the procedure of Example 15A the title compound was prepared from the stannane 17.

EXAMPLE 16

The following compounds were prepared according to Example 15:

p-Nitrobenzyl-(5R,6S)-2-[6-(9-methyl-2-methoxy-β-carbolinyl)]-6[(1R)-1-hydroxyethyl]-carbapen-2-em-3-carboxylate (28) was prepared from the stannane 20 to give the product as a light yellow solid.

p-Nitrobenzyl-(5R,6S)-2-[6-(9-methyl-3-methoxy-γ-carbolinyl)]-6[(1R)-1-hydroxy-ethyl]-carbapen-2-em-3-carboxylate (29) was obtained from the stannane 21 to provide a cream colored solid.

p-Nitrobenzyl-(5R,6S)-2-[6-(9-methyl-δ-carbolinyl)]-6-[(1R )-1-hydroxyethyl]-carbapen-2-em-3-carboxylate (30) was prepared from the stannane 10 to provide a tan solid.

p-Nitrobenzyl-(5R,6S )-2-[6-(1,9-dimethyl-α-carbolinyl)]-6-[(1R)-1 -hydroxyethyl]-carbapen-2-em-3-carboxylate (31) was obtained from the stannane 15.

p-Nitrobenzyl-(5R,6S )-2-[6-(2,9-dimethyl-β-carbolinyl)]-6-[(1R)-1 -hydroxy-ethyl]-carbapen-2-em-3-carboxylate (32). Cross-coupling of the stannane 16 provided 30 as a yellow solid.

p-Nitrobenzyl-(5R,6S )-2-[6-(1-ethyl-9-methyl-α-carbolinyl)]-6-[(1R)- 1-hydroxy-ethyl]-carbapen-2-em-3-carboxylate (33) was prepared from the stannane 19 to give the N-ethyl derivative 33 as a yellow solid.

p-Nitrobenzyl-(5R,6S)-2-[6-(1-oxo-9-methyl-α-carbolinyl)]-6-[(1R)-1-hydroxyethyl]-carbapen-2-em-3-carboxylate (34) was obtained from the stannane 12 to provide the desired product as a yellow solid.

p-Nitrobenzyl-(5R,6S )-2-[6-(2-cyano-9-methyl-α-carbolinyl)]-6-[(1R)- 1-hydroxy-ethyl]-carbapen-2-em-3-carboxylate (35) was prepared from the stannane 24 to give 35 as a light yellow solid.

IR: cm$^{-1}$: 1775 (β-lactam C=O), 1725 (ester C=O).

EXAMPLE 17

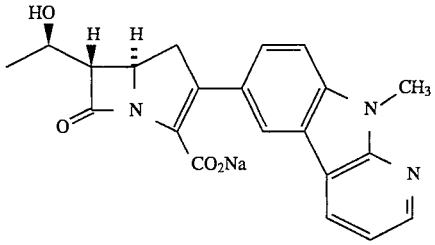

Sodium (5R,6S)-2-[6-(9-methyl-α-carbolinyl)]-6-[(1R)-1 -hydroxyethyl]-carbapen-2-em-3-carboxylate (36)

A solution of 58 mg (0.113 mmol) of 25 from Example 15 in 6 mL of THF and 3 mL of H$_2$O with 122 μL (0.122 mmol) of 1M aqueous NaHCO$_3$ and 6 mg of 10% palladium on carbon was hydrogenated under a balloon filled with hydrogen gas. After 70 min the reaction was filtered over Celite and the filtrate was lyophilized. Purification of the residue on two 1000μ reverse-phase prep plates (1:5 MeCN:H$_2$O) in the cold, followed by elution with (cold 4:1 MeCN:H$_2$O) and washing with cold hexanes, filtration through a 45μ filter and subsequent lyophilization gave 28 mg of 36 as a yellow fluffy solid.

UV: λ$_{max}$ (H$_2$O) 303 nm (NH$_2$OH extinguishable).

EXAMPLE 18

Utilizing the procedure of Example 17, the following carbapenem salts and quaternary derivatives were prepared, with modifications during purification as described below.

Sodium(5R,6S)-2-[6-(9-methyl-β-carbolinyl)]-6-[(1R)-1-hydroxyethyl]-carbapen-2-em-3-carboxylate (37) was prepared from 28 and purified by HPLC: Lobar RP18 column with 14:86 MeCN:H$_2$O as eluent; and lyophilized to a yellow fluffy solid. UV: $\lambda_{max}$ (H$_2$O) 298 nm (NH$_2$OH extinguishable).

Sodium(5R,6S)-2-[6-(9-methyl-γ-carbolinyl)]-6-[(1R)-1-hydroxyethyl]-carbapen-2-em-3-carboxylate (38) was prepared from 29 with HPLC purification (Lobar RP18 column 14:86 MeCN:H$_2$O) followed by lyophilization to provide 38 as a fluffy solid.

UV: $\lambda_{max}$ (H$_2$O) 324 nm (NH$_2$OH extinguishable).

Sodium(5R,6S)-2-[6-(9-methyl-β-carbolinyl)]-6-[(1R)-1-hydroxyethyl]-carbapen-2-em-3-carboxylate (39) was obtained from 30 to provide 39 after lyophilization. UV: $\lambda_{max}$ (H$_2$O) 312 nm (NH$_2$OH extinguishable).

Sodium(5R,6S)-2-[6-(1,9-dimethyl-α-carbolinyl)]-6-[(1R)-1-hydroxyethyl]-carbapen-2-em-3-carboxylate (40). Deblock of 31 with purificaion on reverse phase prep plates using (1:4 MeCN:H$_2$O) followed by lyophilization gave a yellow solid.

UV: $\lambda_{max}$ (H$_2$O) 313 nm (NH$_2$OH extinguishable).

Sodium(5R,6S)-2-[6-(2,9-dimethyl-β-carbolinyl)]-6-[(1R)-1-hydroxyethyl]-carbapen-2-em-3-carboxylate (41) was prepared from 32 with purification on reverse phase prep plates using (1:4 MeCN:H$_2$O) and subsequent lyophilization to a yellow solid.

UV: $\lambda_{max}$ (H$_2$O) 310 nm (NH$_2$OH extinguishable).

Sodium(5R,6S)-2-[6-(1-ethyl-9-dimethyl-α-carbolinyl))]-6-[(1R)-1-hydroxyethyl]-carbapen-2-em-3-carboxylate (42) was prepared from 33 using reverse phase prep plates (1:3 MeCN:H$_2$O) and lyophilization to a yellow fluffy solid.

UV: $\lambda_{max}$ (H$_2$O) 313 nm (NH$_2$OH extinguishable).

Sodium(5R,6S)-2-[6-(1-oxo-9-methyl-α-carbolinyl)]-6-[(1R)-1-hydroxyethyl]-carbapen-2-em-3-carboxylate (43). Deblock of 34 using reverse phase prep plates (1:7 MeCN:H$_2$O) followed by lyophilization gave 43 as a fluffy solid.

UV: $\lambda_{max}$ (H$_2$O) 317 nm (NH$_2$OH extinguishable).

Sodium(5R,6S)-2-[6-(2-cyano-9-dimethyl-α-carbolinyl)]-6-[(1R)-1-hydroxyethyl]-carbapen-2-em-3-carboxylate (44) was obtained from 35 with purification on reverse phase plates (1:4 MeCN:H$_2$O) followed by lyophilization to a yellow fluffy solid.

UV: $\lambda_{max}$ (H$_2$O) 320 nm (NH$_2$OH extinguishable).

EXAMPLE 19

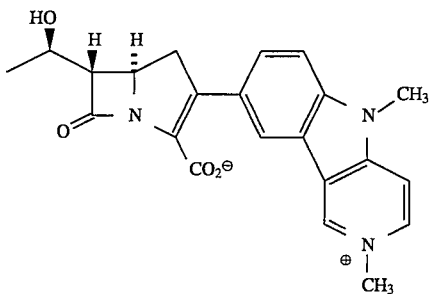

(5R,6S)-2-[6-(3,9-dimethyl-γ-carbolinium)]-6-[(1R)-1-hydroxyethyl]-carbapen-2-em-3-carboxylate (45).

A solution of 40 mg (0.054 mmol) of 27 in 3.5 mL of THF and 1.7 mL of H$_2$O was cooled in an ice bath. To this was added 27 μL (0.027 mmol) of 1N HCl. Desilylation was complete after 20 minutes and 81 μL (0.081 mmol) of 1N NaHCO$_3$ was added, followed by 12 mg of 10% Pd-on-carbon. The reaction was stirred under a H$_2$ balloon for 1.5 h. The catalyst was removed by filtration over Celite, and the filter cake was washed well with water. The filtrate was concentrated and then lyophilized to provide 36 mg of crude product. Purification on a 1000μ reverse phase silica gel plate eluted with 4:1 H$_2$O—MeCN, followed by elution of the product band with cold 4:1 MeCN:H$_2$O, wash with cold hexanes, filtration through a 45μ filter and subsequent lyophilization provided 6.6 mg of 45 as a fluffy solid.

UV: $\lambda_{max}$ (H$_2$O) 330 nm (NH$_2$OH extinguishable).

EXAMPLE 20

Utilizing the procedure from Example 19 the following derivative was prepared:

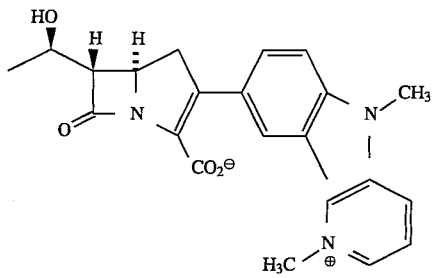

(5R,6S)-2-[6-(4,9-dimethyl-δ-carbolinium)]-6-[(1R)-1-hydroxyethyl]-carbapen-2-em-3-carboxylate (46) was obtained from 26 with purification by HPLC (Lobar RP18 column 14:86 MeCN—H$_2$O) to provide a fluffy yellow solid.

UV: $\lambda_{max}$ (H$_2$O) 308 nm (NH$_2$OH extinguishable).

EXAMPLE 21

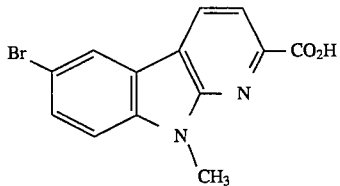

6-Bromo-2-carboxyl-9-methyl-α-carboline (47)

A suspension of 572 mg (2.0 mmol) of 6-bromo-2-cyano-9-methyl-α-carboline (23) in 5.3 mL of 50% by weight aq. NaOH and 1 mL of H$_2$O was heated at reflux. After 2 h an additional 2.6 mL of 50% aq. NaOH was added and heating was continued overnight. The cooled reaction was diluted with 300 mL of H$_2$O and the yellow precipitate was collected by filtration. This material was resuspended in H$_2$O and acidified to pH=5 with acetic acid, then filtered, washed with H$_2$O, azeotroped twice from toluene and vacuum dried at 50° C. to give 500 mg of the title compound as a yellow solid.

ms: (CI/NH$_3$) m/e M+1-CO$_2$=261, 263.

EXAMPLE 22

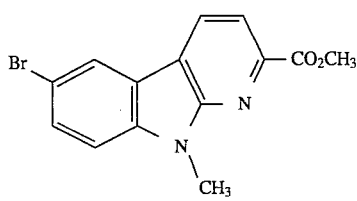

Methyl 6-bromo-9-methyl-α-carbolinly-2-carboxylate (48)

Compound 47 (70 mg, 0.23 mmol) was stirred in a 30 mL solution of HCl/MeOH overnight. The reaction was evaporated twice from MeOH and the solid residue was partitioned between EtOAc and 10% $Na_2CO_3$. The organic layer was separated, washed with brine, dried ($MgSO_4$) and concentrated to provide 58 mg of the title compound as a pale yellow solid.

ms:($CI/NH_3$) m/e (M+1)319, 321

EXAMPLE 23

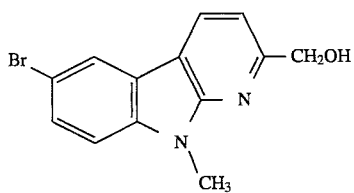

6-Bromo-2-(hydroxymethyl)-9-methyl-α-carboline (49).

A suspension of 205 mg (0.674 mmol) of 48 in 5 mL of dry THF was cooled in an ice bath and 0.67 mL of 2M $LiBH_4$ in THF was added. After 30 min the ice bath was removed and stirring was continued for 4 h at ambient temperature. The reaction was quenched with $H_2O$ and extracted twice with EtOAc. The combined organic layer was washed with brine, dried ($MgSO_4$) and evaporated to furnish 141 mg of 49 as a solid.

ms:(EI) m/e290, 292.

EXAMPLE 24

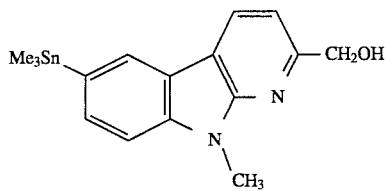

6-Trimethylstannyl-2-(hydroxymethyl)-9-methyl-α-carboline (50)

Compound 49 (175 mg, 0.6 mmol) was suspended in 5 mL of toluene and treated with 0.14 mL (236 mg, 0.72 mmol, 1.2 equiv.) of hexamethylditin, 35 mg (0.03 mmol, 5 mol %) of $Pd(PPh_3)_4$ and 5 mg (0.019 mmol, 3 mol %) of triphenylphosphine. The yellow suspension was purged with $N_2$ and then heated at reflux. After 2 h an additional 20 mg of $Pd(PPh_3)_4$ was added to the black reaction. After a total of 3.5 h the cooled reaction was diluted with EtOAc, washed with 10% $NaHCO_3$, followed by brine and dried ($MgSO_4$). Evaporation provided a residual oil which was purified on a silica gel flash column eluted with initially 20% and then 30% EtOAc in hexanes to provide 105.4 mg of 50 as a white solid.

EXAMPLE 25

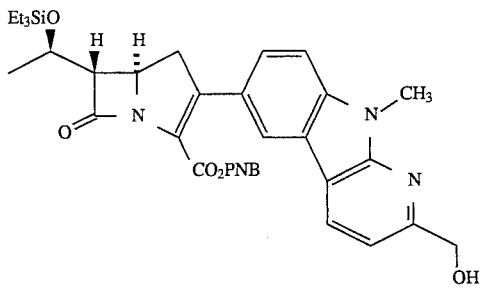

p-Nitrobenzyl-(5R,6S)-2-[6-(2-hydroxymethyl-9-methyl-α-carbolinyl)-6-[(1R)-triethylsilyloxyethyl]-carbapen-2-em-3-carboxylate (51)

The triethylsilyl protected bicyclic β-ketoester (70.7 mg, 0.153 mmol) was dissolved in 0.8 mL of dry $CH_2Cl_2$ and cooled to −78° C. Triethylamine (32 μL, 0.229 mmol) was added and a yellow color was noted. Triflic anhydride (33.5 μL, 0.199 mmol) was added dropwise. Of this solution, 0.3 ml (approximately 0.056 mmol) was transferred to another vessel which was cooled at −78° C. To this was added 0.3 mL of NMP, 10 mg (0.028 mmol) of 50 from Example 24, 0.9 mg of $Pd_2(dba)_3.CHCl_3$, and 31 μL of 1M $ZnCl_2$ in $Et_2O$. The reaction was warmed immediately to ambient temperature and stirred for 30 minutes. After partitioning the reaction between EtOAc and $H_2O$, the organic layer was washed twice with $H_2O$ and then brine. After drying ($MgSO_4$), concentration provided 33 mg of a residual oil. Purification on a silica gel flash column eluting with 2:1, and then 1:1 hexanes:EtOAc gave 10.7 mg of 51 as a yellow solid.

EXAMPLE 26

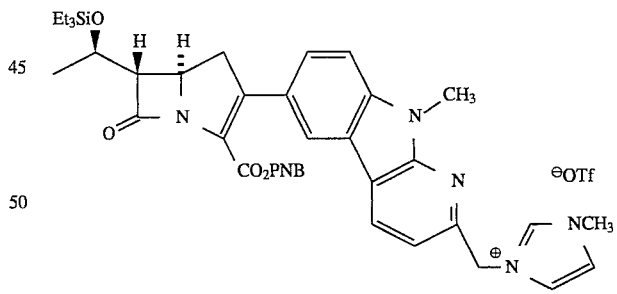

p-Nitrobenzyl-(5R,6S)-2-[6-(2-(N-methyl-imidazolium)methyl-9 -methyl-α-carbolinyl)-6-[(1R)-triethylsilyloxyethyl]-carbapen-2-em-3 -carboxylate triflate (52)

To 8 mg (0.012 mmol) of 51 in 0.2 mL of dry $CH_2Cl_2$ was added 4 μL (0.05 mmol) of N-methylimidazole. The solution was cooled in an ice bath and treated with 4 μL (0.024 mmol) of triflic anhydride. After 30 minutes the reaction was diluted with EtOAc, washed twice with $H_2O$, then dried ($Na_2SO_4$) and evaporated to furnish 8.4 mg of the title compound as a yellow solid.

EXAMPLE 27

Utilizing the procedure from Example 19 the following carbapenem derivative is prepared:

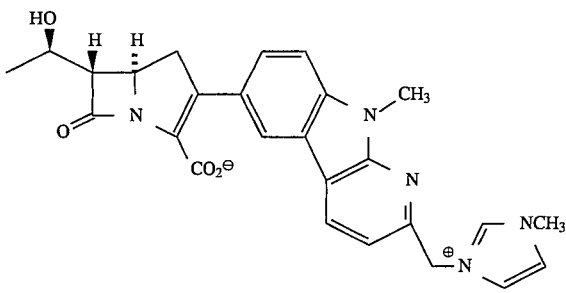

(5R,6S)-2-[6-(2-(N-methyl-imidazolium)methyl-9-methyl-α-carbolinyl)-6-[(1R)-hydroxyethyl]-carbapen-2-em-3-carboxylate (53)

EXAMPLE 28

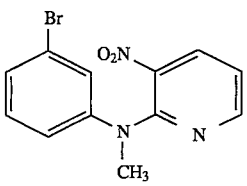

N-methyl-m-bromo-N-(3-nitro-2'-pyridyl)aniline (54)

A mixture of 5.6 g(30 mmol) of N-methyl-m-bromoaniline and 1.6 g(10 mmol) of 2-chloro-3-nitropyridine was heated at 160° C. under an inert atmosphere of nitrogen for 6 h. The mixture was partitioned between EtOAc and saturated aqueous sodium bicarbonate and the organic phase separated, washed again with aqueous bicarbonate solution, dried MgSO₄, and evaporated to give a solid residue. Purification by chromatography on silica gel using hexane-EtOAc(8:1) as eluent gave 2.5 g of the title compound.

EXAMPLE 29

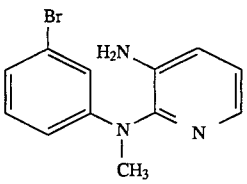

Utilizing the procedure from Example 4 N-methyl-m-bromo-N-(3-amino-2'-pyridyl(aniline (55) was prepared from 54 of Example 28.

EXAMPLE 30

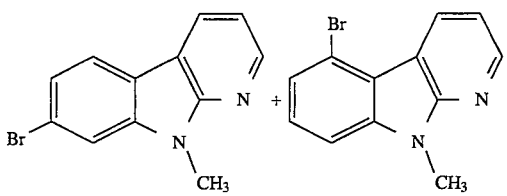

Utilizing the procedure of Example 5 5- and 7-Bromo-9-methyl-α-carbolines(56) and (57) were prepared from 55 of Example 29 in an isolated ratio of 3:2 respectively.

EXAMPLE 31

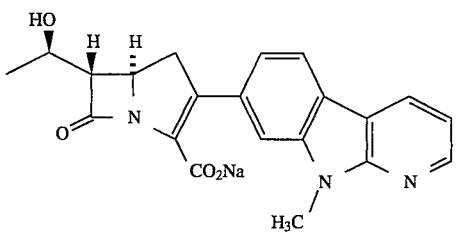

Utilizing the procedures outlined in Examples 7, 15, and 17 Sodium(5R,6S)-2-[7-(9-methyl-α-carbolinyl)]-6-[(1R)-1-hydroxyethyl]-carbapen-2-em-3-carboxylate (58) was prepared from compound 57 of Example 30.

EXAMPLE 32

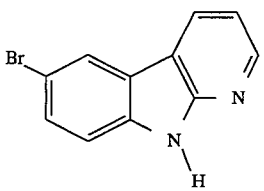

Utilizing the procedure of Example 1 α-carboline was converted into 9-bromo-α-carboline (59)

EXAMPLE 33

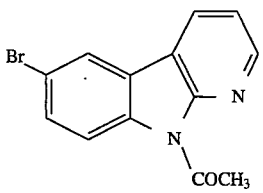

6-Bromo-9-acetyl-α-carboline (60)

A mixture of 408 mg (1.65 mmol) of 59 from Example 32 and 400 μL of acetic anhydride in 4 mL of pyridine was stirred in an inert atmosphere of nitrogen at ambient temperature overnight. A 10% aqueous solution of NaHCO₃ was slowly added until no further effervescence was observed and the resulting solid precipitate was collected by filtration. After washing well with water and pet. ether, drying yielded 380 mg of cream colored product 60.

EXAMPLE 34

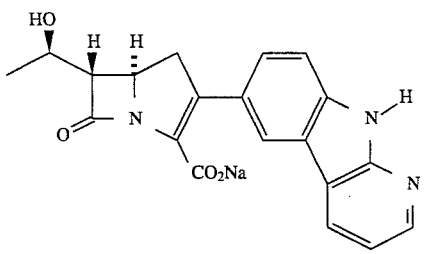

Utilizing the procedures outlined in Examples 7, 15A, and 19 Sodium(5R,6S)-2-[6-α-carbolinyl)]-6-[(1R)-1-hydroxy-ethyl]-carbapen-2-em-3-carboxylate (61) was prepared from compound 60.

What is claimed is:

1. A compound represented by the formula:

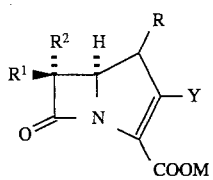 (I)

or a pharmaceutically acceptable salt thereof, wherein:

Y is:

a) 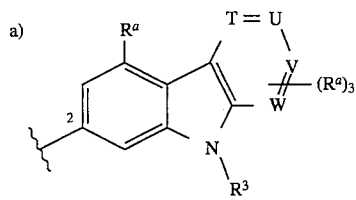

or b) 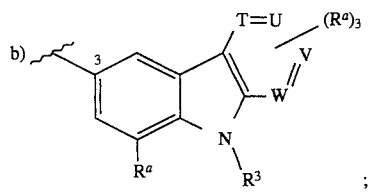

R and $R^3$ represent H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

M is selected from:
 i) hydrogen;
 ii) a pharmaceutically acceptable esterifying group or removable carboxyl protecting group, or
 iii) a negative charge which is balanced by a positively charged group;

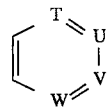

represents an aromatic 6 membered ring;

one of T, U, V and W represents $N^+R^y$ or N, and the others represent C;

$R^y$ is selected from the group consisting of: —H, —O—, —$C_{1-4}$ alkyl, —$OC_{1-4}$ alkyl, —$NH_2$, —$NHC_{1-4}$ alkyl, —$N(C_{1-4}$ alkyl$)_2$, —$C_{1-4}$ alkyl$(R^q)_{1-3}$, —$OC_{1-4}$ alkyl$(R^q)_{1-3}$, —$NHC_{1-4}$ alkyl$(R^q)_{1-3}$ and —$N[C_{1-4}$ alkyl$(R^q)_{1-3}]_2$ wherein $R^q$ is as defined below;

four $R^a$ groups are present, each independently selected from the group consisting of hydrogen, Type I and Type II set forth below, provided that 0–1 $R^a$ groups are selected from Type I and the remaining $R^a$ groups are selected from H and Type II;

Type I substituents are selected from the group consisting of:

(a)

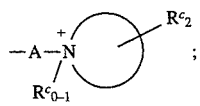

wherein A is $(CH_2)_m$—Q—$(CH_2)_n$, in which m is 0–6, n is 1–6 and Q is selected from the group consisting of: a covalent bond, —O—, —S—, —SO—, —$SO_2$—, —NH—, —$SO_2NH$—, —$NHSO_2$—, —CONH—, —NHCO—, —$SO_2N(C_{1-4}$ alkyl)—, —$N(C_{1-4}$ alkyl)$SO_2$—, —$CON(C_{1-4}$ alkyl)—, —$N(C_{1-4}$ alkyl)CO—, —CH=CH—, —CO—, —OC(O)—, —C(O)O— and —$N(C_{1-4}$ alkyl);

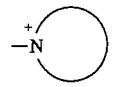

is a 5- or 6-membered monocyclic heterocycle or an 8-, 9- or 10-membered bicyclic heterocycle, said heterocycle containing a first nitrogen in an aromatic 5- or 6-membered first ring, with attachment of the heterocycle to A by way of said first nitrogen, said first nitrogen being tertiary or quaternary, with the first ring containing 0–1 of either O or S, with the first ring containing 0–3 additional nitrogen atoms, with the first ring optionally fused to a 3- or 4-membered moiety to form an optional second ring, with the moiety containing at least one carbon atom, with the moiety containing 0–1 of either O or S, with the moiety containing 0–2 nitrogen atoms, and with the moiety being saturated or unsaturated and the second ring being aromatic or non-aromatic;

each $R^c$ independently represents H or $R^a$ as defined below under Type II;

(b) 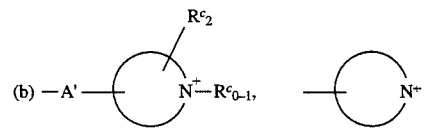

is a 5- or 6-membered monocyclic heterocycle or an 8-, 9- or 10-membered bicyclic heterocycle, the heterocycle containing a first nitrogen in an aromatic 5- or 6-membered first ring, 0–1 of either O or S, and 0–2 additional nitrogen atoms, said first nitrogen being quaternary, with the first ring optionally fused to a 3- or 4-membered moiety to form an optional second ring which is aromatic or non-aromatic, said moiety containing at least one carbon atom, 0–1 of O or S, and 0–2 additional nitrogen atoms, said moiety being saturated or unsaturated;

$R^c$ is as defined above;

A' represents $(CH_2)_m$—Q—$(CH_2)_{n'}$, where m is as defined above and n' independently represents 0–6;

Q is as defined above except that when m and n' are both 0, Q is not a covalent bond;

$$—A_p—N^+—R^xR^y_{(0-1)}R^z \quad (c)$$

where $R^x$ and $R^z$ are as defined under Type II below, or $R^x$ and $R^z$ together represent a $C_{2-4}$ alkylidene radical which forms a ring, optionally substituted with 1–3 groups selected from $R^q$ as defined below, optionally interrupted by $N(O)R^e$ or $N^+(R^e)_2$, where $R^e$ is hydrogen, $C_{1-4}$ alkyl, or $C_{1-4}$ alkyl substituted with 1–3 groups selected from $R^q$ as defined below, when present, $R^y$ is as defined above;

or $R^x$, $R^y$ and $R^z$ are taken together and represent a $C_{5-10}$ tertiary alkylidene radical which with $N^+$ forms a bicyclic ring, said tertiary alkylidene radical being optionally substituted with 1–3 groups selected from $R^q$ as defined below, and the tertiary carbon of the tertiary alkylidene radical is optionally replaced with a member selected from the group consisting of: N, $N^+$-$R^e$, where $R^e$ is as previously defined, and $N^+$-$O^-$;

A is as defined above, and p is 0 or 1;

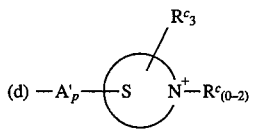

where

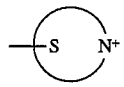

represents a 4-, 5- or 6-membered monocyclic heterocycle or an 8-, 9- or 10-membered bicyclic heterocycle, said heterocycle containing a first nitrogen in a first ring, with the first ring being non-aromatic and either saturated or unsaturated, said first nitrogen being a quaternary nitrogen, said first ring containing in addition to carbon and the first nitrogen, 0 or 1 member selected from the group consisting of N, O, S, S(O), $S(O)_2$ and $NR^e$, where $R^e$ is as defined above, said first non-aromatic ring being optionally fused to a 2-, 3- or 4-membered moiety to form an optional second ring;

A' is defined above;

p is defined above; and $R^q$ is defined below;

and

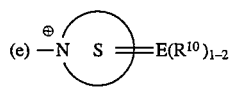

wherein

E represents C, N or $N^+$ attached to the ring by a double bond;

$R^{10}$ represents H, $C_{1-4}$ alkyl or $C_{1-4}$ alkyl substituted with from 1–3 $R^q$ groups, with $R^q$ as defined below;

represents a 4-, 5- or 6-membered monocyclic unsaturated heterocycle, containing a first nitrogen, said first nitrogen being a quaternary nitrogen, said ring further containing 0 or 1 member selected from the group consisting of N, O, S, S(O), $S(O)_2$ and $NR^e$, where $R^e$ is as defined above;

and wherein the Type II substituents are selected from the group consisting of:

a) —$CF_3$;
b) a halogen atom selected from the group consisting of: —Br, —Cl, —F and —I;
c) —$OC_{1-4}$ alkyl, wherein the alkyl is optionally substituted with 1–3 groups selected from $R^q$, wherein $R^q$ represents a member selected from the group consisting of: —OH, —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ where $M^a$ is hydrogen, alkali metal, methyl or phenyl, tetrazolyl, where the point of attachment is the carbon atom of the tetrazole ring and one of the nitrogen atoms is mono-substituted by $M^a$ as defined above, and —$SO_3M^b$, where $M^b$ is hydrogen or an alkali metal;

d) —OH;

e) —O(C=O)$R^s$, where $R^s$ is $C_{1-4}$ alkyl or phenyl, each of which is optionally substituted by 1–3 $R^q$ groups as defined above;

f) —O(C=O)N($R^x$)$R^z$, where $R^x$ and $R^z$ are independently H, $C_{1-4}$ alkyl, optionally substituted by 1–3 $R^q$ groups as defined above, together a 3- to 5-membered alkylidene radical to form a ring, optionally substituted with 1–3 $R^q$ groups as defined above, or together a 2- to 4-membered alkylidene radical, interrupted by —O—, —S—, —S(O)— or —$S(O)_2$— to form a ring, where the ring is optionally substituted with 1–3 $R^q$ groups as defined above;

g) —$S(O)_q$—$R^s$ where q=0–2, and $R^s$ is defined above;

h) —$SO_2N(R^x)R^z$ where $R^x$ and $R^z$ are as defined above;

i) —$N_3$;

j) —N($R^t$)(C=O)H, where $R^t$ is H or $C_{1-4}$ alkyl, and the $C_{1-4}$ alkyl portion thereof is optionally substituted with 1–3 $R^q$ groups, wherein $R^q$ is as defined above;

k) —N($R^t$)(C=O)$C_{1-4}$ alkyl, wherein $R^t$ is as defined above, and the alkyl group is optionally substituted by 1–3 $R^q$ groups, with $R^q$ as defined above;

l) —N($R^t$)(C=O)O$C_{1-4}$ alkyl, wherein $R^t$ is as defined above, and the alkyl portion thereof is optionally substituted with 1–3 $R^q$ groups, with $R^q$ as defined above;

m) —N(R^t)(C=O)N(R^y)R^z wherein R^t, R^y and R^z are as defined above;

n) —N(R^t)SO_2R^s, wherein R^s and R^t are as defined above;

o) —CN;

p) —(C=O)H or —CH(OCH_3)_2;

q) —C(OCH_3)_2C_{1-4} alkyl, wherein the alkyl portion thereof is optionally substituted with 1–3 R^q groups, with R^q as defined above;

r) —(C=O)R^s, wherein R^s is as defined above;

s) —(C=NOR^z)R^y wherein R^y and R^z are as defined above, except they may not be joined together to form a ring;

t) —(C=O)OC_{1-4} alkyl, wherein the alkyl portion thereof is optionally substituted with 1–3 R^q groups, with R^q as defined above;

u) —(C=O)N(R^y)R^z wherein R^y and R^z are as defined above;

v) —(C=O)—N(OR^y)R^z wherein R^y and R^z are as defined above, except they may not be joined together to form a ring;

w) —(C=S)N(R^y)R^z wherein R^y and R^z are as defined above;

x) —COOM^b, wherein M^b is as defined above;

y) —SCN;

z) —SCF_3;

aa) tetrazolyl, where the point of attachment is the carbon atom of the tetrazole ring and one of the nitrogen atoms is mono-substituted by hydrogen, an alkali metal or a C_1–C_4 alkyl optionally substituted by R^q as defined above;

ab) an anionic function selected from the group consisting of: phosphono which is P=O(OM^b)_2; alkylphosphono which is P=O(OM^b)—[O(C_1–C_4 alkyl)]; alkylphosphinyl which is P=O(OM^b)—(C_1–C_4-alkyl); phosphoramido which is P=O(OM^b)N(R^y)R^z or P=O(OM^b)NHR^w; sulfino which is SO_2M^b; sulfo which is SO_3M^b; acylsulfonamide which is selected from the group consisting of: CONM^bSO_2R^w, CONM^bSO_2N(R^y)R^z, SO_2NM^bCON(R^y)R^z and SO_2NM^bCN, where R^w is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally substituted with 1–3 R^q groups, wherein R^q is as defined above; M^b is as defined above; and R^y and R^z are as defined above;

ac) C_5–C_7 cycloalkyl group in which one of the carbon atoms in the ring is replaced by a heteroatom selected from O, S, NH, or N(C_1–C_4 alkyl) and in which one additional carbon may be replaced by NH or N(C_1–C_4 alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C_2–C_4 alkenyl radical, optionally substituted with 1–3 substituents a) to ac) above and phenyl which is optionally substituted by 1–3 R^q groups, with R^q as defined above;

ae) C_2–C_4 alkynyl radical, optionally substituted by one to three of the substituents a) to ac) above;

af) C_1–C_4 alkyl radical;

ag) C_1–C_4 alkyl substituted with 1–3 of the substituents a)–ac) above;

ah) a 2-oxazolidinonyl moiety in which the point of attachment is the nitrogen atom of the oxazolidinone ring, the ring oxygen atom is optionally replaced by a heteroatom selected from S and NR^t, where R^t is as defined above, and one of the saturated carbon atoms of the oxazolidinone ring is optionally mono-substituted by one of the substituents a) to ag) above.

2. A compound in accordance with claim 1 of the formula Ia:

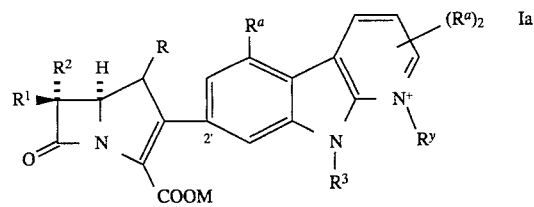

wherein R, R^1, R^2, R^3, R^a, R^y and M are as previously defined.

3. A compound in accordance with claim 1 of the formula Ib:

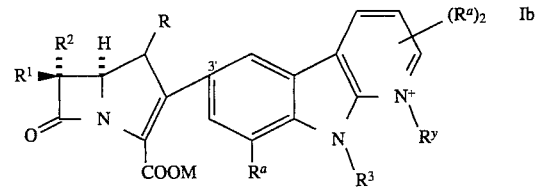

wherein R, R^1, R^2, R^3, R^a, R^y and M are as previously defined.

4. A compound in accordance with claim 3 of the formula:

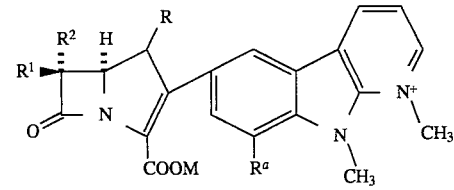

or

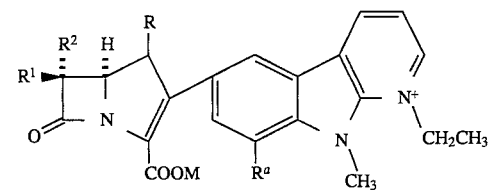

wherein R, R^1, R^2, R^a and M are as previously defined.

5. A compound in accordance with claim 3 of the formula:

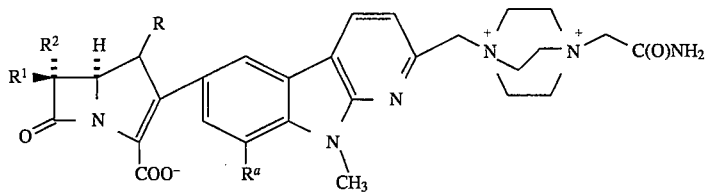

in combination with a suitable counterion, wherein R, $R^1$ and $R^2$ are as previously defined, and $R^a$ represents H or a Type II substituent group.

6. A compound in accordance with claim 1 of the formula Ic:

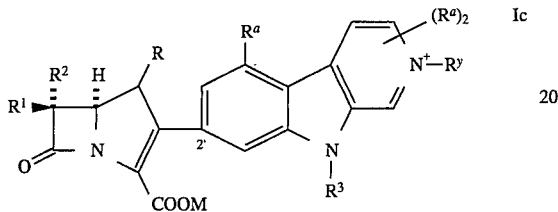

wherein R, $R^1$, $R^2$ $R^3$, $R^a$, $R^y$ and M are as previously defined.

7. A compound in accordance with claim 1 of the formula Id:

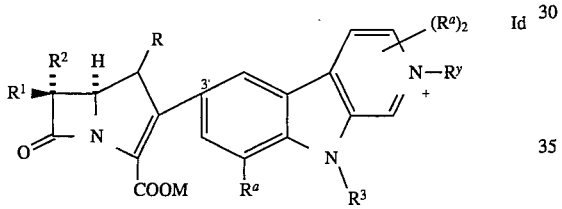

wherein R, $R^1$, $R^2$ $R^3$, $R^a$, $R^y$ and M are as previously defined.

8. A compound in accordance with claim 7 of the formula:

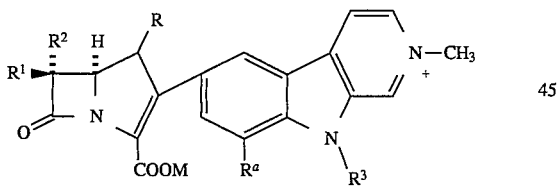

wherein R, $R^1$, $R^2$, $R^a$ and M are as previously defined, and $R^3$ is H or $CH_3$.

9. A compound in accordance with claim 1 wherein one $R^a$ group is of type Ia and is selected from the group consisting of:

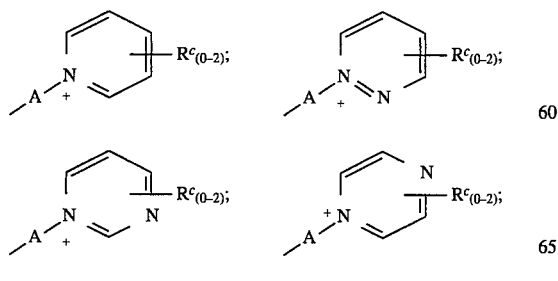

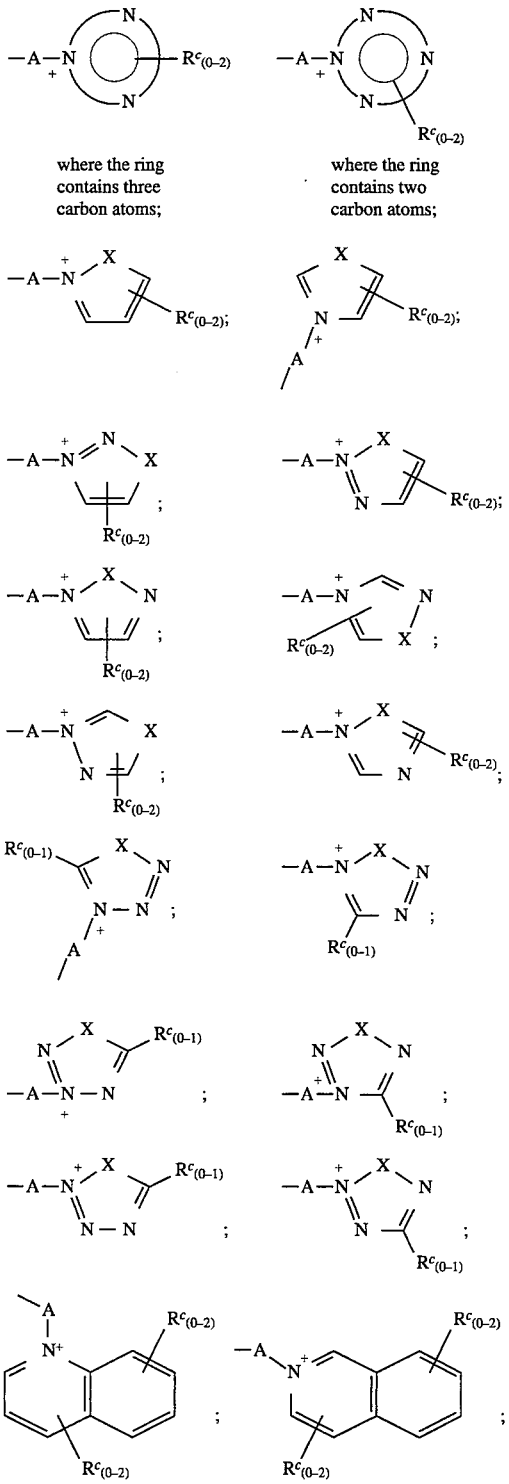

101
-continued

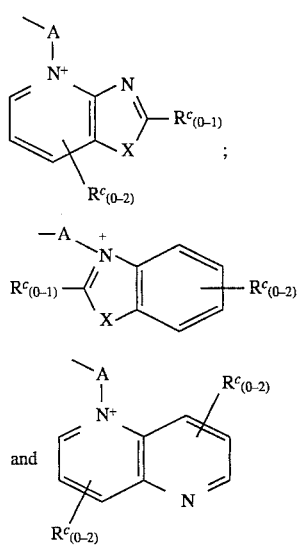

where X represents O, S, or NR$^c$,

A is $(CH_2)_m$—Q—$(CH_2)_n$, in which m is 0–6, n is 1–6 and Q is selected from the group consisting of: a covalent bond, —O—, —S—, —SO—, —SO$_2$—, —NH—, —SO$_2$NH—, —NHSO$_2$—, —CONH—, —NHCO—, —SO$_2$N(C$_{1-4}$alkyl)—, —N(C$_{1-4}$alkyl)SO$_2$—, —CON(C$_{1-4}$alkyl)—, —N(C$_{1-4}$alkyl)CO—, —CH=CH—, —CO—, —OC(O)—, —C(O)O— and —N(C$_{1-4}$ alkyl);

R$^c$ is selected from the group consisting of: —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl)$_2$, —CH$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$ CONH$_2$ and CH$_2$CON(C$_1$-C$_4$alkyl)$_2$, where M$^b$ represents hydrogen or an alkali metal.

10. A compound in accordance with claim 1 wherein one R$^a$ group is of type Ib and is selected from the group consisting of:

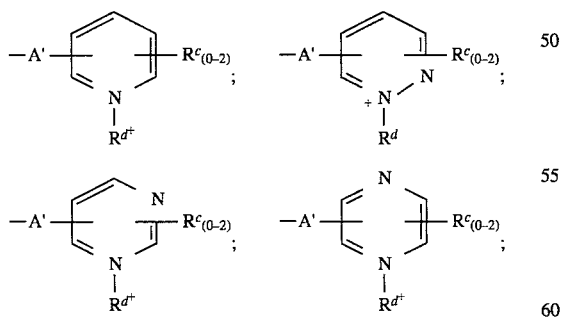

102
-continued

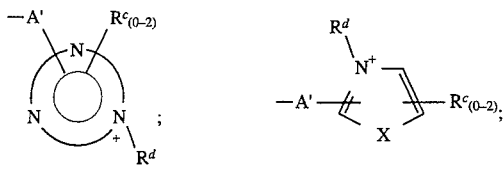

where the ring contains three carbon atoms;

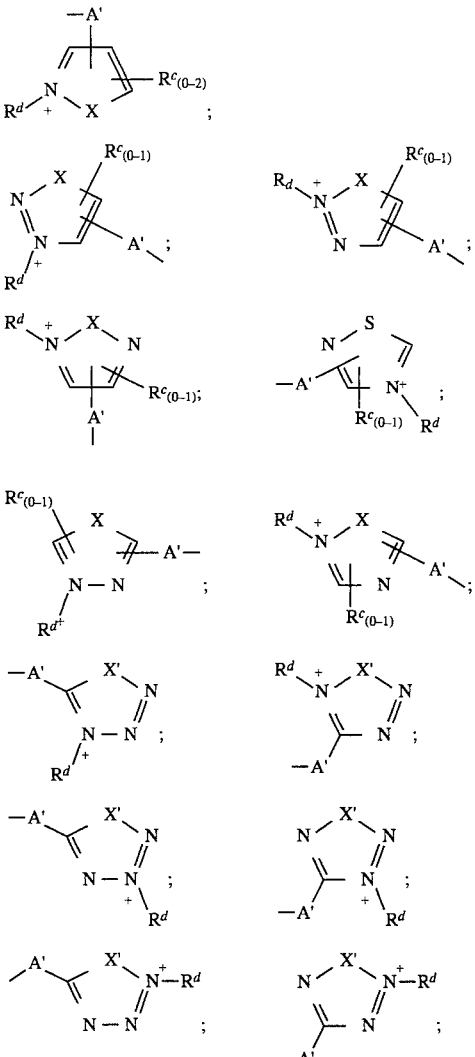

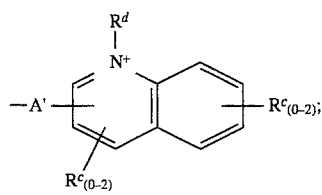

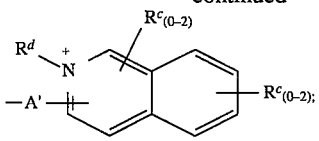

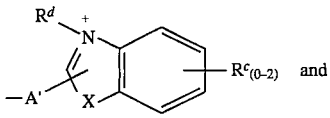

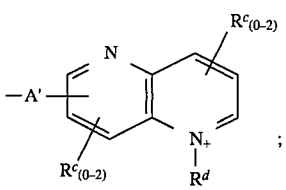

X represents O; S or NR$^c$;

X' represents O or S;

A' represents (CH$_2$)$_m$—Q—(CH$_2$)$_{n'}$, wherein m is 0–6 and n' is 0–6;

Q is selected from the group consisting of: a covalent bond, —O—, —S—, —SO—, —SO$_2$—, —NH—, —SO$_2$NH—, —NHSO$_2$—, —CONH—, —NHCO—, —SO$_2$N(C$_{1-4}$alkyl)—, —N(C$_{1-4}$alkyl)SO$_2$—, —CON(C$_{1-4}$alkyl)—, —N(C$_{1-4}$alkyl)CO—, —CH=CH—, —CO—, —OC(O)—, —C(O)O— and —N(C$_{1-4}$ alkyl)$_2$ except that when n' is 0, Q does not represent a covalent bond;

R$^c$ is selected from the group consisting of: —SCH$_3$, —SOCH$_3$, —CH$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, —CH$_2$CH$_3$, —CH$_2$CONH$_2$ and —CH$_2$CON(C$_1$–C$_4$alkyl)$_2$, —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, —CH$_2$CH$_3$, —CH$_2$CONH$_2$ and —CH$_2$CON(C$_1$–C$_4$alkyl)$_2$, where M$^b$ represents H or an alkali metal;

and R$^d$ represents hydrogen, —CH$_3$, —CH$_2$CH$_3$, —CH$_2$CH$_2$CH$_3$, —CH$_2$COOM$^b$ or —CH$_2$SO$_3$M$^b$, wherein M$^b$ represents H or an alkali metal.

11. A compound in accordance with claim 1 wherein one R$^a$ is of Type Ic and is selected from the group consisting of:

—Ap—N$^+$(CH$_3$)$_3$, —Ap—N$^+$(CH$_2$CH$_3$)$_3$,
—AP—N$^+$(CH$_3$)$_2$CH$_2$R$^q$ —Ap—N$^+$(CH$_2$CH$_3$)$_2$CH$_2$CH$_2$R$^q$,

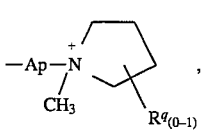 , 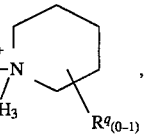 ,

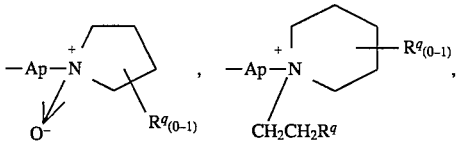

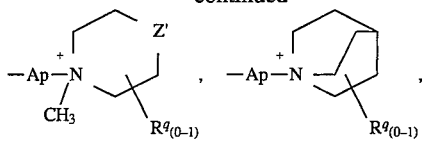

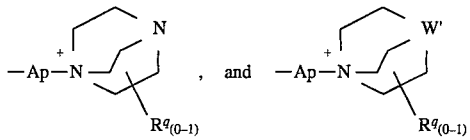

wherein:

W' is N$^+$R$^e$ or NO;

Z' is O, S, NR$^e$, N(O)R$^e$, SO, SO$_2$ or N$^+$(R$^e$)$_2$;

A is (CH$_2$)$_m$—Q—(CH$_2$)$_n$, in which m is 0–6, n is 1–6 and Q is selected from the group consisting of: a covalent bond, —O—, —S—, —SO—, —SO$_2$—, —NH—, —SO$_2$NH—, —NHSO$_2$—, —CONH—, —NHCO—, —SO$_2$ N(C$_{1-4}$alkyl)—, —N(C$_{1-4}$alkyl)SO$_2$—, —CON(C$_{1-4}$alkyl)—, —N(C$_{1-4}$alkyl)CO—, —CH=CH—, —CO—, —OC(O)—, —C(O)O— and —N(C$_{1-4}$ alkyl);

Q is selected from the group consisting of: a covalent bond, —O—, —S—, —SO—, —SO$_2$—, —NH—, —SO$_2$NH—, —NHSO$_2$—, —CONH—, —NHCO—, —SO$_2$N(C$_{1-4}$alkyl)—, —N(C$_{1-4}$alkyl)SO$_2$—, —CON(C$_{1-4}$alkyl)—, —N(C$_{1-4}$alkyl)CO—, —CH=CH—, —CO—, —OC(O)—, —C(O)O— and —N(C$_{1-4}$ alkyl)$_2$ except that when n' is 0, Q does not represent a covalent bond;

R$^q$ represents a member selected from the group consisting of: —OH, —OCH$_3$, —CN, —C(O)NH$_2$, —OC(O)NH$_2$, —CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$, where M$^a$ is hydrogen, alkali metal, methyl or phenyl, tetrazolyl, where the point of attachment is the carbon atom of the tetrazole ring and one of the nitrogen atoms is mono-substituted by M$^a$ as defined above, and —SO$_3$M$^b$ (where M$^b$ is hydrogen or an alkali metal.

12. A compound in accordance with claim 1 wherein one R$^a$ group is of type Id and is selected from the group consisting of:

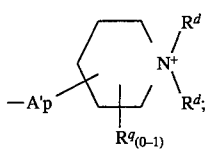

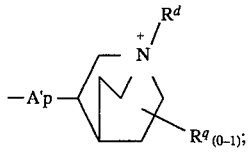

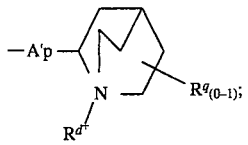

-continued

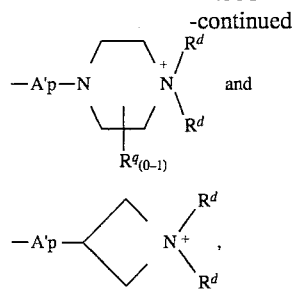

wherein:

A' represents $(CH_2)_m\text{—}Q\text{—}(CH_2)_{n'}$, wherein m is 0–6 and n' independently represents 0–6;

Q is as defined above except that when m and n' are both 0, Q is not a covalent bond;

p is 0 or 1;

$R^d$ represents hydrogen, —$CH_3$, —$CH_2CH_3$, —$CH_2CH_2CH_3$, —$CH_2COOM^b$ or —$CH_2SO_3M^b$, where $M^b$ is H or an alkali metal; and $R^q$ represents a member selected from the group consisting of: —OH, —$OCH_3$, —CN, —$C(O)NH_2$, —$OC(O)NH_2$, —CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$, where $M^a$ is hydrogen, alkali metal, methyl or phenyl, tetrazolyl, where the point of attachment is the carbon atom of the tetrazole ring and one of the nitrogen atoms is mono-substituted by $M^a$ as defined above, and —$SO_3M^b$ where $M^b$ is as defined above.

13. A compound in accordance with claim 9 wherein $R^c$ is selected from the group consisting of: —$NH_2$, —$SCH_3$, —$SOCH_3$, —$CH_2OH$, —$(CH_2)_2OH$, —$OCH_3$, —$COOM^b$, —$CH_2COOM^b$, —$CH_2CH_2COOM^b$, —$CH_2SOCH_3$, —$CH_2SCH_3$, —$SO_3M^b$, —$CH_2SO_3M^b$, —$CH_2CH_2SO_3M^b$, —Br, —Cl, —F, —I, —$CH_3$, —$CH_2CH_3$, —$CH_2CONH_2$ and —$CH_2CON(C_1-C_4 \text{ alkyl})_2$ where $M^b$ is H or an alkali metal.

14. A compound in accordance with claim 10 wherein:

$R^c$ is selected from the group consisting of: —$NH_2$, —$SCH_3$, —$SOCH_3$, —$CH_2OH$, —$(CH_2)_2OH$, —$OCH_3$, —$COOM^b$, —$CH_2COOM^b$, —$CH_2CH_2COOM^b$, —$CH_2SOCH_3$, —$CH_2SCH_3$, —$SO_3M^b$, —$CH_2 SO_3M^b$, —$CH_2CH_2SO_3M^b$, —Br, —Cl, —F, —I, —$CH_3$, —$CH_2CH_3$, —$CH_2 CONH_2$ and —$CH_2CON(C_1-C_4 \text{ alkyl})_2$ where $M^b$ is H or an alkali metal, and $R^d$ is selected from the group consisting of: hydrogen, —$CH_3$, —$CH_2CH_3$, —$CH_2CH_2CH_3$, —$CH_2COOM^b$, —$CH_2SO_3M^b$, —$NH_2$ and O(–), where $M^b$ represents H or an alkali metal.

15. A compound in accordance with claim 13 wherein —A— is selected from the group consisting of: —$CH_2$—, —$CH_2CH_2$—, —$CH_2CH_2CH_2$—, —$CH_2CH_2CH_2CH_2$—, —$OCH_2CH_2$—, —$SOCH_2$—, —$SO_2CH_2$—, —$SCH_2CH_2$—, —$SOCH_2CH_2$—, —$SO_2CH_2CH_2$—, —$NHCH_2CH_2$—, —$N(CH_3)CH_2CH_2$—, —$CH_2N(CH_3)CH_2CH_2$—, —$CONHCH_2CH_2$—, —$SO_2NHCH_2CH_2$—, —$COCH_2$—, —$CH=CHCH_2$— and —$CH_2OCH_2CH_2$—.

16. A compound in accordance with claim 14 wherein A' is selected from the group consisting of: —O—, —S—, —NH—, —$SO_2$—, —$SO_2NH$—, —CONH—, —CH=CH—, —$CH_2S$—, —$CH_2NH$—, —$CONHCH_2$— and —$SO_2NHCH_2$—.

17. A compound in accordance with claim 1 wherein one $R^a$ group is of Type II and is selected from the group consisting of:

| | |
|---|---|
| —$OCH_3$ | |
| —$OCH_2CH_2OH$ | —$OCH_2CO_2Na$ |
| —F | —$CF_3$ |
| —Br | —Cl |
| —OH | —I |
| —$OCONH_2$ | —$OCOCH_3$ |
| —$SOCH_3$ | —$SCH_3$ |
| —$SCH_2CH_2OH$ | —$SO_2CH_3$ |
| —$SO_2NH_2$ | —$SOCH_2CH_2OH$ |
| —NHCHO | —$SO_2N(CH_3)_2$ |
| —$NHCO_2CH_3$ | —$NHCOCH_3$ |
| —CN | —$NHSO_2CH_3$ |
| —$COCH_3$ | —CHO |
| —CH=NOH | —$COCH_2OH$ |
| —CH=$NOCH_2CO_2H$ | —CH=$NOCH_3$ |
| —$SO_2CH_2CH_2OH$ | —CH=$NOCMe_2CO_2H$ |
| —CH=$NOCMe_2CO_2Me$ | —$CO_2CH_2CH_2OH$ |
| —$CONH_2$ | —$CONHCH_3$ |
| —$CON(CH_3)_2$ | —$CONHCH_2CN$ |
| —$CONHCH_2CONH_2$ | —$CONHCH_2CO_2H$ |
| —CONHOH | —$CONHCH_3$ |
| —tetrazolyl | —$CO_2Na$ |
| —$SCF_3$ | —$PO_3NaH$ |
| —$CONHSO_2Ph$ | —$CONHSO_2NH_2$ |
| —$SO_3Na$ | —$SO_2NHCN$ |
| —$SO_2NHCONH_2$ | —CH=CHCN |
| —CH=CHCONH_2 | —CH=$CHCO_2Na$ |
| —C≡C—$CONH_2$ | —C≡C—CN |
| —$CH_2OH$ | —$CH_2N_3$ |
| —$CH_2CO_2Na$ and | —$CH_2I$. |

18. A compound having the structure set forth in Table 1 below:

TABLE 1

[Structure: bicyclic β-lactam with hydroxyethyl group, carboxylate, attached to phenyl ring (positions 1-4) bearing N-R³ and linked to pyridinium ring (positions 5-7) with N⁺-Rʸ, and Rᵃ substituent]

| R | R³ | Rʸ | Rᵃ | Rᵃ Position(s) |
|---|---|---|---|---|
| H | CH₃ | CH₃ | H | 1, 5–7 |
| CH₃ | CH₃ | CH₃ | H | 1, 5–7 |
| H | H | CH₃ | H | 1, 5–7 |
| CH₃ | H | CH₃ | H | 1, 5–7 |
| H | CH₃ | CH₂CH₃ | H | 1, 5–7 |
| CH₃ | CH₃ | CH₂CH₃ | H | 1, 5–7 |
| H | H | CH₂CH₃ | H | 1, 5–7 |
| CH₃ | H | CH₂CH₃ | H | 1, 5–7 |
| H | CH₃ | CH₂CONH₂ | H | 1, 5–7 |
| CH₃ | CH₃ | CH₂CONH₂ | H | 1, 5–7 |
| H | CH₃ | CH₂CH₂OH | H | 1, 5–7 |
| CH₃ | CH₃ | CH₂CH₂OH | H | 1, 5–7 |
| H | CH₃ | CH₃ | CN | 1 |
| CH₃ | CH₃ | CH₃ | CN | 1 |
| H | CH₃ | CH₃ | SMe | 1 |
| CH₃ | CH₃ | CH₃ | SMe | 1 |
| H | CH₃ | CH₃ | SO₂Me | 1 |
| CH₃ | CH₃ | CH₃ | SO₂Me | 1 |
| H | CH₃ | CH₃ | CONH₂ | 1 |
| CH₃ | CH₃ | CH₃ | CONH₂ | 1 |
| H | CH₃ | CH₃ | Br | 1 |
| CH₃ | CH₃ | CH₃ | Br | 1 |
| H | CH₃ | CH₃ | NH₂ | 7 |
| CH₃ | CH₃ | CH₃ | NH₂ | 7 |
| H | CH₃ | Absent | —CH₂—N⁺(imidazole)N—Me | 7 |
| CH₃ | CH₃ | Absent | —CH₂—N⁺(imidazole)N—Me | 7 |
| H | CH₃ | Absent | —CH₂—N⁺(imidazole)N—Me | 6 |
| CH₃ | CH₃ | Absent | —CH₂—N⁺(imidazole)N—Me | 6 |
| H | CH₃ | Absent | —CH₂CH₂—N⁺(imidazole)N—Me | 7 |
| CH₃ | CH₃ | Absent | —CH₂CH₂—N⁺(imidazole)N—Me | 7 |
| H | CH₃ | Absent | —CH₂CH₂—N⁺(imidazole)N—Me | 6 |
| CH₃ | CH₃ | Absent | —CH₂CH₂—N⁺(imidazole)N—Me | 6 |
| H | CH₃ | Absent | —CH₂—N⁺(imidazole)N—CH₂CH₂CONH₂ | 7 |

TABLE 1-continued

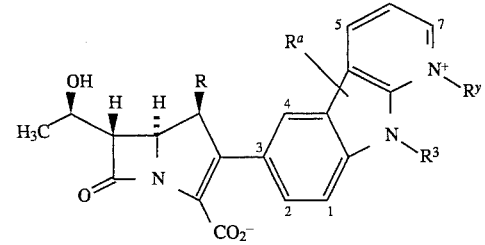

| R | R³ | Rʸ | Rᵃ | Rᵃ Position(s) |
|---|---|---|---|---|
| CH₃ | CH₃ | Absent | 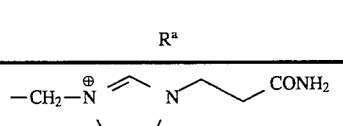 —CH₂—N⁺⟨imidazole⟩—CH₂CH₂CONH₂ | 7 |
| H | CH₃ | Absent | —CH₂—N⁺⟨imidazole⟩—CH₂CH₂CONH₂ | 6 |
| CH₃ | CH₃ | Absent | —CH₂—N⁺⟨imidazole⟩—CH₂CH₂CONH₂ | 6 |
| H | CH₃ | Absent | 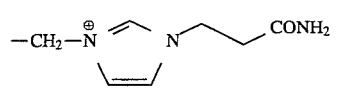 —CH₂—N⁺⟨piperazine⟩N⁺—CH₂CONH₂  X⁻ | 7 |
| CH₃ | CH₃ | Absent | —CH₂—N⁺⟨piperazine⟩N⁺—CH₂CONH₂  X⁻ | 7 |
| H | CH₃ | Absent | —CH₂—N⁺⟨piperazine⟩N⁺—CH₂CONH₂  X⁻ | 6 |
| CH₃ | CH₃ | Absent | —CH₂—N⁺⟨piperazine⟩N⁺—CH₂CONH₂  X⁻ | 6 |
| H | CH₃ | Absent | CH₂CH₂—N⁺⟨piperazine⟩N⁺·CH₂CONH₂  X⁻ | 7 |
| CH₃ | CH₃ | Absent | CH₂CH₂—N⁺⟨piperazine⟩N⁺·CH₂CONH₂  X⁻ | 7 |
| H | CH₃ | Absent | CH₂CH₂—N⁺⟨piperazine⟩N⁺·CH₂CONH₂  X⁻ | 6 |

TABLE 1-continued

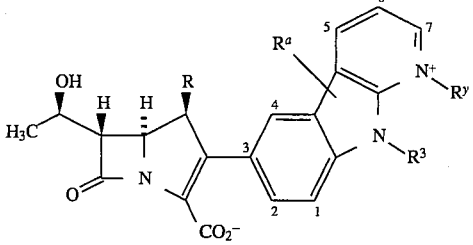

| R | R³ | Rʸ | Rᵃ | Rᵃ Position(s) |
|---|----|----|----|----|
| CH₃ | CH₃ | Absent | 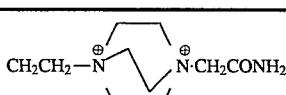 $CH_2CH_2-\overset{\oplus}{N}\underset{\phantom{.}}{\diagup\!\!\!\diagdown}\overset{\oplus}{N}\cdot CH_2CONH_2$  X⁻ | 6 |
| H | CH₃ | Absent | 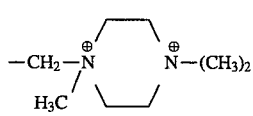 $-CH_2-\overset{\oplus}{\underset{H_3C}{N}}\diagup\!\!\!\diagdown\overset{\oplus}{N}-(CH_3)_2$  X⁻ | 7 |
| CH₃ | CH₃ | Absent | 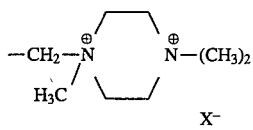 $-CH_2-\overset{\oplus}{\underset{H_3C}{N}}\diagup\!\!\!\diagdown\overset{\oplus}{N}-(CH_3)_2$  X⁻ | 7 |
| H | CH₃ | Absent | 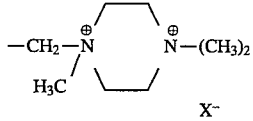 $-CH_2-\overset{\oplus}{\underset{H_3C}{N}}\diagup\!\!\!\diagdown\overset{\oplus}{N}-(CH_3)_2$  X⁻ | 6 |
| CH₃ | CH₃ | Absent | 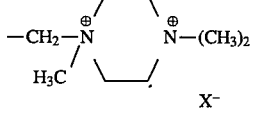 $-CH_2-\overset{\oplus}{\underset{H_3C}{N}}\diagup\!\!\!\diagdown\overset{\oplus}{N}-(CH_3)_2$  X⁻ | 6 |
| H | CH₃ | Absent | 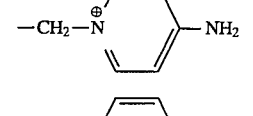 —CH₂—pyridinium-NH₂ | 7 |
| CH₃ | CH₃ | Absent | 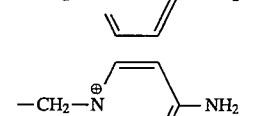 —CH₂—pyridinium-NH₂ | 7 |
| H | CH₃ | Absent | 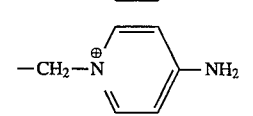 —CH₂—pyridinium-NH₂ | 6 |
| CH₃ | CH₃ | Absent | 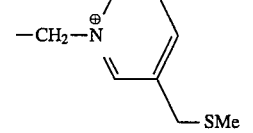 —CH₂—pyridinium-NH₂ | 6 |
| H | CH₃ | Absent |  —CH₂—pyridinium-CH₂SMe | 7 |

TABLE 1-continued

| R | R³ | Rʸ | Rᵃ | Rᵃ Position(s) |
|---|---|---|---|---|
| $CH_3$ | $CH_3$ | Absent | —$CH_2$—N⁺(pyridinium)—$SMe$ | 7 | wherein $X^-$ represents a suitable counterion, R represents H as $CH_3$ and when $R^y$ is absent, the N atom to which it is drawn attached is non-quaternary.

19. A compound having the structure set forth in Table 2 below:

TABLE 2

| $R^{a1}$ | $R^3$ | $R^Y$ | $R^{a2}$ |
|---|---|---|---|
| CN | H | Absent | —$CH_2$—N⁺(piperazine)N⁺—$CH_2CONH_2$ $X^-$ |
| CN | $CH_3$ | Absent | —$CH_2$—N⁺(piperazine)N⁺—$CH_2CONH_2$ $X^-$ |
| Br | H | Absent | —$CH_2$—N⁺(piperazine)N⁺—$CH_2CONH_2$ $X^-$ |
| Br | $CH_3$ | Absent | —$CH_2$—N⁺(piperazine)N⁺—$CH_2CONH_2$ $X^-$ |
| $SCH_3$ | H | Absent | —$CH_2$—N⁺(piperazine)N⁺—$CH_2CONH_2$ $X^-$ |
| $SCH_3$ | $CH_3$ | Absent | —$CH_2$—N⁺(piperazine)N⁺—$CH_2CONH_2$ $X^-$ |

TABLE 2-continued

[Structure shown: β-lactam core with hydroxyethyl group, linked to a pyrroline carboxylate bearing substituent R, connected to a phenyl ring (positions 1-4) with substituents $R^{a1}$, $NR^3$, and a pyridinium ring (positions 5-7) bearing $R^{a2}$ and $N^+R^y$]

| $R^{a1}$ | $R^3$ | $R^Y$ | $R^{a2}$ |
|---|---|---|---|
| $SO_2CH_3$ | H | Absent | $-CH_2-N^+(\text{ring})N^+-CH_2CONH_2$ $X^-$ |
| $SO_2CH_3$ | $CH_3$ | Absent | $-CH_2-N^+(\text{ring})N^+-CH_2CONH_2$ $X^-$ |
| $CONH_2$ | H | Absent | $-CH_2-N^+(\text{ring})N^+-CH_2CONH_2$ $X^-$ |
| $CONH_2$ | $CH_3$ | Absent | $-CH_2-N^+(\text{ring})N^+-CH_2CONH_2$ $X^-$ |
| CN | H | $CH_3$ | $-CH_2-N^+(\text{imidazole})N-CH_3$ $X^-$ |
| CN | $CH_3$ | $CH_3$ | $-CH_2-N^+(\text{imidazole})N-CH_3$ $X^-$ |
| Br | H | $CH_3$ | $-CH_2-N^+(\text{imidazole})N-CH_3$ $X^-$ |
| Br | $CH_3$ | $CH_3$ | $-CH_2-N^+(\text{imidazole})N-CH_3$ $X^-$ |
| SMe | H | $CH_3$ | $-CH_2-N^+(\text{imidazole})N-CH_3$ $X^-$ |
| SMe | $CH_3$ | $CH_3$ | $-CH_2-N^+(\text{imidazole})N-CH_3$ $X^-$ |
| $SO_2CH_3$ | H | $CH_3$ | $-CH_2-N^+(\text{imidazole})N-CH_3$ $X^-$ |
| $SO_2CH_3$ | $CH_3$ | $CH_3$ | $-CH_2-N^+(\text{imidazole})N-CH_3$ $X^-$ |
| $CONH_2$ | H | $CH_3$ | $-CH_2-N^+(\text{imidazole})N-CH_3$ $X^-$ |
| $CONH_2$ | $CH_3$ | $CH_3$ | $-CH_2-N^+(\text{imidazole})N-CH_3$ $X^-$ |

TABLE 2-continued
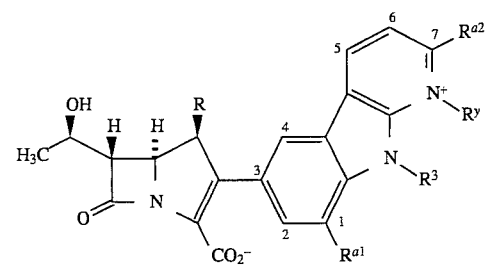
| $R^{a1}$ | $R^3$ | $R^Y$ | $R^{a2}$ |
|---|---|---|---|
| CN | H | Absent | 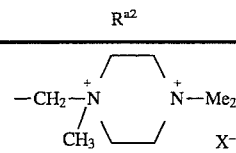 |
| CN | $CH_3$ | Absent | 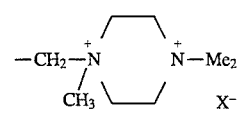 |
| Br | H | Absent | 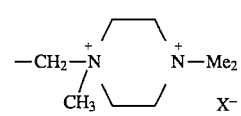 |
| Br | $CH_3$ | Absent | 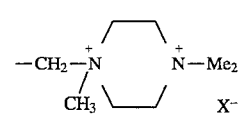 |
| SMe | H | Absent | 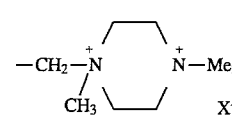 |
| SMe | $CH_3$ | Absent | 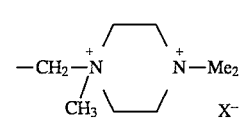 |
| $SO_2Me$ | H | Absent | 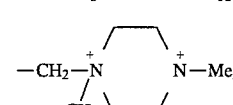 |
| $SO_2Me$ | $CH_3$ | Absent | 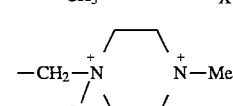 |
| $CONH_2$ | H | Absent | 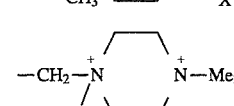 |
| $CONH_2$ | $CH_3$ | Absent | 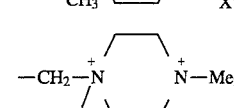 |
| CN | H | $CH_3$ | 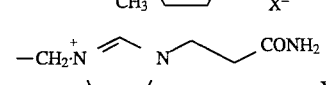 |
| CN | $CH_3$ | $CH_3$ | 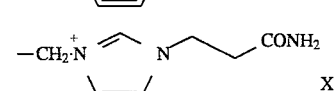 |

TABLE 2-continued

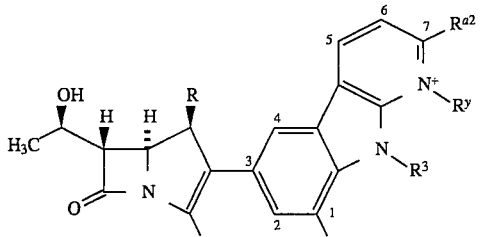

| $R^{a1}$ | $R^3$ | $R^Y$ | $R^{a2}$ |
|---|---|---|---|
| Br | H | $CH_3$ | $-CH_2-\overset{+}{N}$⟨imidazole⟩$N-CH_2CH_2-CONH_2$  $X^-$ |
| Br | $CH_3$ | $CH_3$ | $-CH_2-\overset{+}{N}$⟨imidazole⟩$N-CH_2CH_2-CONH_2$  $X^-$ |
| SMe | H | $CH_3$ | $-CH_2-\overset{+}{N}$⟨imidazole⟩$N-CH_2CH_2-CONH_2$  $X^-$ |
| SMe | $CH_3$ | $CH_3$ | $-CH_2-\overset{+}{N}$⟨imidazole⟩$N-CH_2CH_2-CONH_2$  $X^-$ |
| $SO_2Me$ | H | $CH_3$ | $-CH_2-\overset{+}{N}$⟨imidazole⟩$N-CH_2CH_2-CONH_2$  $X^-$ |
| $SO_2Me$ | $CH_3$ | $CH_3$ | $-CH_2-\overset{+}{N}$⟨imidazole⟩$N-CH_2CH_2-CONH_2$  $X^-$ |
| $CONH_2$ | H | $CH_3$ | $-CH_2-\overset{+}{N}$⟨imidazole⟩$N-CH_2CH_2-CONH_2$  $X^-$ |
| $CONH_2$ | $CH_3$ | $CH_3$ | $-CH_2-\overset{+}{N}$⟨imidazole⟩$N-CH_2CH_2-CONH_2$  $X^-$ |
| CN | H | $CH_2CH_3$ | $-CH_2-\overset{+}{N}$⟨imidazole⟩$N-CH_2CH_2-CONH_2$  $X^-$ |
| CN | $CH_3$ | $CH_2CH_3$ | $-CH_2-\overset{+}{N}$⟨imidazole⟩$N-CH_2CH_2-CONH_2$  $X^-$ |
| Br | H | $CH_2CH_3$ | $-CH_2-\overset{+}{N}$⟨imidazole⟩$N-CH_2CH_2-CONH_2$  $X^-$ |
| Br | $CH_3$ | $CH_2CH_3$ | $-CH_2-\overset{+}{N}$⟨imidazole⟩$N-CH_2CH_2-CONH_2$  $X^-$ |
| SMe | H | $CH_2CH_3$ | $-CH_2-\overset{+}{N}$⟨imidazole⟩$N-CH_2CH_2-CONH_2$  $X^-$ |
| SMe | $CH_3$ | $CH_2CH_3$ | $-CH_2-\overset{+}{N}$⟨imidazole⟩$N-CH_2CH_2-CONH_2$  $X^-$ |
| $SO_2Me$ | H | $CH_2CH_3$ | $-CH_2-\overset{+}{N}$⟨imidazole⟩$N-CH_2CH_2-CONH_2$  $X^-$ |

TABLE 2-continued

[Structure diagram showing a bicyclic core with OH, H₃C, R, CO₂⁻, N⁺Rʸ, Rᵃ², Rᵃ¹, R³ substituents at labeled positions 1–7]

| Rᵃ¹ | R³ | Rʸ | Rᵃ² |
|---|---|---|---|
| SO₂Me | CH₃ | CH₂CH₃ | —CH₂-N⁺=CH-N-CH₂CH₂CONH₂ X⁻ (imidazolium) |
| CONH₂ | H | CH₂CH₃ | —CH₂-N⁺=CH-N-CH₂CH₂CONH₂ X⁻ (imidazolium) |
| CONH₂ | CH₃ | CH₂CH₃ | —CH₂-N⁺=CH-N-CH₂CH₂CONH₂ X⁻ (imidazolium) | wherein X⁻ represents a suitable counterion, R represents H or CH₃ and when Rʸ is absent, the N atom to which it is drawn attached is non-quaternary.

20. A compound having the structure set forth in Table 3 below:

TABLE 3

[Structure diagram with OH, H₃C, H, H, R, CO₂⁻, Rᵃ, N⊕Rʸ, N-R³ at positions 1–8]

| R | R³ | Rʸ | Rᵃ | Rᵃ Position(s) |
|---|---|---|---|---|
| H | CH₃ | CH₃ | H | 1, 5, 6, 8 |
| CH₃ | CH₃ | CH₃ | H | 1, 5, 6, 8 |
| H | H | CH₃ | H | 1, 5, 6, 8 |
| CH₃ | H | CH₃ | H | 1, 5, 6, 8 |
| H | CH₃ | CH₂CH₃ | H | 1, 5, 6, 8 |
| CH₃ | CH₃ | CH₂CH₃ | H | 1, 5, 6, 8 |
| H | H | CH₂CH₃ | H | 1, 5, 6, 8 |
| CH₃ | H | CH₂CH₃ | H | 1, 5, 6, 8 |
| H | CH₃ | CH₂CONH₂ | H | 1, 5, 6, 8 |
| CH₃ | CH₃ | CH₂CONH₂ | H | 1, 5, 6, 8 |
| H | CH₃ | CH₂CH₂OH | H | 1, 5, 6, 8 |
| CH₃ | CH₃ | CH₂CH₂OH | H | 1, 5, 6, 8 |
| H | CH₃ | CH₃ | CN | 1 |
| CH₃ | CH₃ | CH₃ | CN | 1 |
| H | CH₃ | CH₃ | SMe | 1 |
| CH₃ | CH₃ | CH₃ | SMe | 1 |
| H | CH₃ | CH₃ | SO₂Me | 1 |
| CH₃ | CH₃ | CH₃ | SO₂Me | 1 |
| H | CH₃ | CH₃ | CONH₂ | 1 |
| CH₃ | CH₃ | CH₃ | CONH₂ | 1 |
| H | CH₃ | CH₃ | Br | 1 |
| CH₃ | CH₃ | CH₃ | Br | 1 |
| H | CH₃ | CH₃ | NH₂ | 6 |
| CH₃ | CH₃ | CH₃ | NH₂ | 6 |
| H | CH₃ | CH₃ | NH₂ | 8 |
| CH₃ | CH₃ | CH₃ | NH₂ | 8 |

TABLE 3-continued

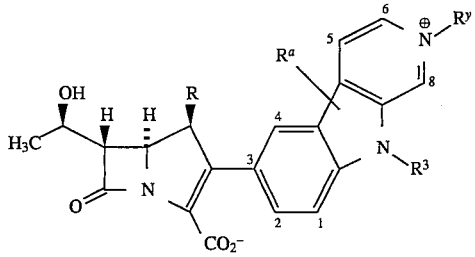

| R | R³ | Rʸ | Rᵃ | Rᵃ Position(s) |
|---|---|---|---|---|
| H | CH₃ | Absent | —CH₂—N⁺⌐=\_N—Me (imidazolium) | 6 |
| CH₃ | CH₃ | Absent | —CH₂—N⁺⌐=\_N—Me | 6 |
| H | CH₃ | Absent | —CH₂—N⁺⌐=\_N—Me | 8 |
| CH₃ | CH₃ | Absent | —CH₂—N⁺⌐=\_N—Me | 8 |
| H | CH₃ | Absent | —CH₂—N⁺⌐=\_N—Me | 6 |
| CH₃ | CH₃ | Absent | —CH₂CH₂—N⁺⌐=\_N—Me | 6 |
| H | CH₃ | Absent | —CH₂CH₂—N⁺⌐=\_N—Me | 8 |
| CH₃ | CH₃ | Absent | —CH₂CH₂—N⁺⌐=\_N—Me | 8 |
| H | CH₃ | Absent | —CH₂—N⁺⌐=\_N—CH₂CH₂CONH₂ | 6 |
| CH₃ | CH₃ | Absent | —CH₂—N⁺⌐=\_N—CH₂CH₂CONH₂ | 6 |
| H | CH₃ | Absent | —CH₂—N⁺⌐=\_N—CH₂CH₂CONH₂ | 8 |
| CH₃ | CH₃ | Absent | —CH₂—N⁺⌐=\_N—CH₂CH₂CONH₂ | 8 |
| H | CH₃ | Absent | —CH₂—N⁺(DABCO)N⁺—CH₂CONH₂  X⁻ | 6 |

TABLE 3-continued

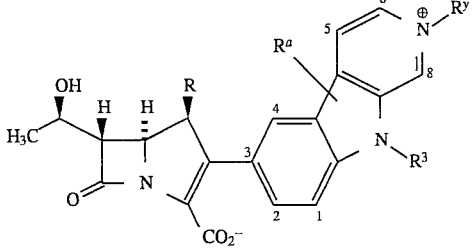

| R | R³ | Rʸ | Rᵃ | Rᵃ Position(s) |
|---|---|---|---|---|
| CH₃ | CH₃ | Absent | —CH₂—N⁺(C₄H₈)N⁺—CH₂CONH₂  X⁻ | 6 |
| H | CH₃ | Absent | —CH₂—N⁺(C₄H₈)N⁺—CH₂CONH₂  X⁻ | 8 |
| CH₃ | CH₃ | Absent | —CH₂—N⁺(C₄H₈)N⁺—CH₂CONH₂  X⁻ | 8 |
| H | CH₃ | Absent | CH₂CH₂—N⁺(C₄H₈)N⁺·CH₂CONH₂  X⁻ | 6 |
| CH₃ | CH₃ | Absent | CH₂CH₂—N⁺(C₄H₈)N⁺·CH₂CONH₂  X⁻ | 6 |
| H | CH₃ | Absent | CH₂CH₂—N⁺(C₄H₈)N⁺·CH₂CONH₂  X⁻ | 8 |
| CH₃ | CH₃ | Absent | CH₂CH₂—N⁺(C₄H₈)N⁺·CH₂CONH₂  X⁻ | 8 |
| H | CH₃ | Absent | —CH₂—N⁺(CH₃)(C₄H₈)N⁺—(CH₃)₂  X⁻ | 6 |
| CH₃ | CH₃ | Absent | —CH₂—N⁺(CH₃)(C₄H₈)N⁺—(CH₃)₂  X⁻ | 6 |

TABLE 3-continued
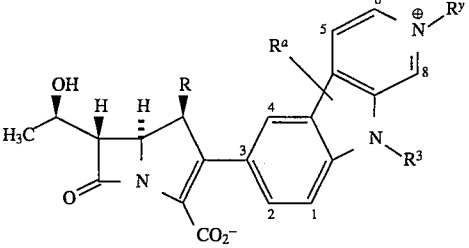
| R | R³ | Rʸ | Rᵃ | Rᵃ Position(s) |
|---|---|---|---|---|
| H | CH₃ | Absent | 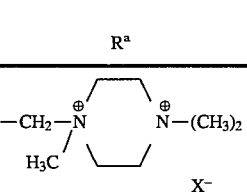 | 8 |
| CH₃ | CH₃ | Absent | 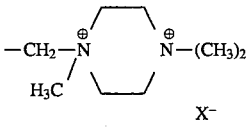 | 8 |
| H | CH₃ | Absent | 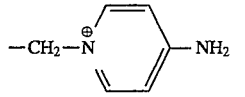 | 6 |
| CH₃ | CH₃ | Absent |  | 6 |
| H | CH₃ | Absent | 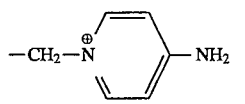 | 8 |
| CH₃ | CH₃ | Absent |  | 8 |
| H | CH₃ | Absent | 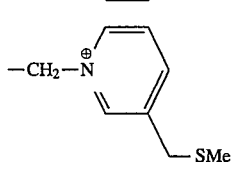 | 6 |
| CH₃ | CH₃ | Absent | 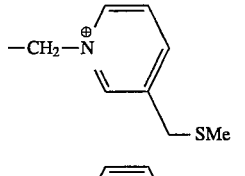 | 6 |
| H | CH₃ | Absent | 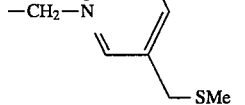 | 8 |

TABLE 3-continued

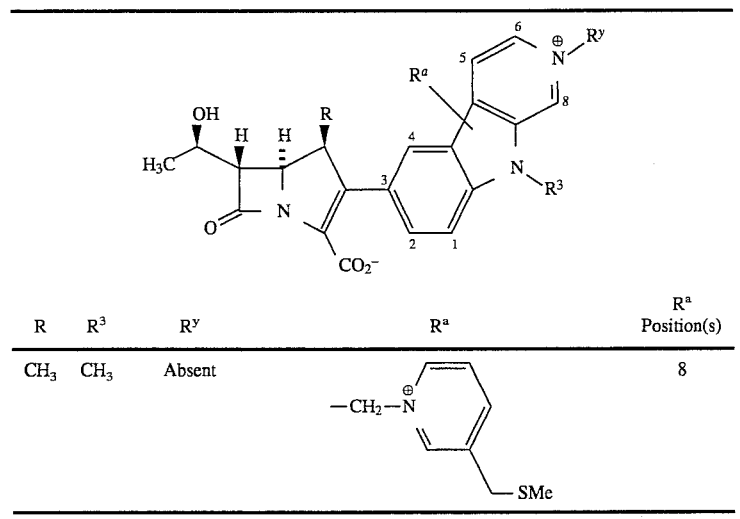

| R | R³ | Rʸ | Rᵃ | Rᵃ Position(s) |
|---|---|---|---|---|
| CH₃ | CH₃ | Absent | —CH₂—N⁺(pyridine)—SMe | 8 | wherein X⁻ represents a suitable counterion and when Rʸ is absent, the N atom to which it is drawn attached is non-quaternary.

21. A compound having the structure set forth in Table 4 below:

TABLE 4

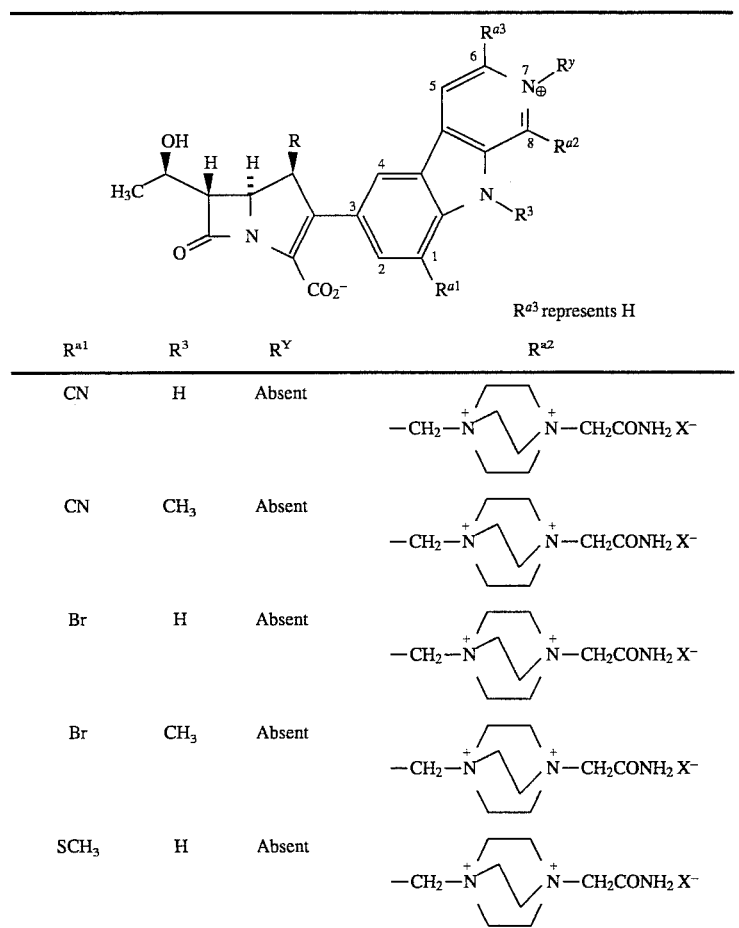

Rᵃ³ represents H

| Rᵃ¹ | R³ | Rʸ | Rᵃ² |
|---|---|---|---|
| CN | H | Absent | —CH₂—N⁺(piperidine)N⁺—CH₂CONH₂ X⁻ |
| CN | CH₃ | Absent | —CH₂—N⁺(piperidine)N⁺—CH₂CONH₂ X⁻ |
| Br | H | Absent | —CH₂—N⁺(piperidine)N⁺—CH₂CONH₂ X⁻ |
| Br | CH₃ | Absent | —CH₂—N⁺(piperidine)N⁺—CH₂CONH₂ X⁻ |
| SCH₃ | H | Absent | —CH₂—N⁺(piperidine)N⁺—CH₂CONH₂ X⁻ |

TABLE 4-continued

[Structure diagram showing the core compound with numbered positions 1-8, substituents $R^{a1}$, $R^{a2}$, $R^{a3}$, $R^{y}$, $R^{3}$, R, OH, H, H$_3$C, CO$_2^-$, and N$^\oplus$]

$R^{a3}$ represents H

| $R^{a1}$ | $R^3$ | $R^Y$ | $R^{a2}$ |
|---|---|---|---|
| SCH$_3$ | CH$_3$ | Absent | $-CH_2-\overset{+}{N}\underset{\diagdown\diagup}{\diagup\diagdown}\overset{+}{N}-CH_2CONH_2\ X^-$ |
| SO$_2$CH$_3$ | H | Absent | $-CH_2-\overset{+}{N}\underset{\diagdown\diagup}{\diagup\diagdown}\overset{+}{N}-CH_2CONH_2\ X^-$ |
| SO$_2$CH$_3$ | CH$_3$ | Absent | $-CH_2-\overset{+}{N}\underset{\diagdown\diagup}{\diagup\diagdown}\overset{+}{N}-CH_2CONH_2\ X^-$ |
| CONH$_2$ | H | Absent | $-CH_2-\overset{+}{N}\underset{\diagdown\diagup}{\diagup\diagdown}\overset{+}{N}-CH_2CONH_2\ X^-$ |
| CONH$_2$ | CH$_3$ | Absent | $-CH_2-\overset{+}{N}\underset{\diagdown\diagup}{\diagup\diagdown}\overset{+}{N}-CH_2CONH_2\ X^-$ |
| CN | H | CH$_3$ | $-CH_2\cdot\overset{+}{N}\underset{\diagdown\diagup}{=\!\!=}N-CH_3\ X^-$ |
| CN | CH$_3$ | CH$_3$ | $-CH_2\cdot\overset{+}{N}\underset{\diagdown\diagup}{=\!\!=}N-CH_3\ X^-$ |
| Br | H | CH$_3$ | $-CH_2\cdot\overset{+}{N}\underset{\diagdown\diagup}{=\!\!=}N-CH_3\ X^-$ |
| Br | CH$_3$ | CH$_3$ | $-CH_2\cdot\overset{+}{N}\underset{\diagdown\diagup}{=\!\!=}N-CH_3\ X^-$ |
| SMe | H | CH$_3$ | $-CH_2\cdot\overset{+}{N}\underset{\diagdown\diagup}{=\!\!=}N-CH_3\ X^-$ |
| SMe | CH$_3$ | CH$_3$ | $-CH_2\cdot\overset{+}{N}\underset{\diagdown\diagup}{=\!\!=}N-CH_3\ X^-$ |
| SO$_2$CH$_3$ | H | CH$_3$ | $-CH_2\cdot\overset{+}{N}\underset{\diagdown\diagup}{=\!\!=}N-CH_3\ X^-$ |
| SO$_2$CH$_3$ | CH$_3$ | CH$_3$ | $-CH_2\cdot\overset{+}{N}\underset{\diagdown\diagup}{=\!\!=}N-CH_3\ X^-$ |

TABLE 4-continued

[Structure: β-lactam compound with OH-CH(CH3)- group, azetidinone ring, connected to phenyl ring (positions 1-4) bearing substituents R^a1 at position 1, CO2- via position 2, linked at position 3 to a diene system with positions 5,6 bearing R^a3 and N⊕-R^y at position 7, and =CH-R^a2 at position 8; N-R^3 on the phenyl ring. R^a3 represents H]

| R^a1 | R^3 | R^Y | R^a2 |
|---|---|---|---|
| CONH$_2$ | H | CH$_3$ | $-CH_2\overset{+}{N}$⟨imidazole⟩$N-CH_3$ X$^-$ |
| CONH$_2$ | CH$_3$ | CH$_3$ | $-CH_2\overset{+}{N}$⟨imidazole⟩$N-CH_3$ X$^-$ |
| CN | H | Absent | $-CH_2-\overset{+}{N}(CH_3)$⟨piperazine⟩$\overset{+}{N}-Me_2$ X$^-$ |
| CN | CH$_3$ | Absent | $-CH_2-\overset{+}{N}(CH_3)$⟨piperazine⟩$\overset{+}{N}-Me_2$ X$^-$ |
| Br | H | Absent | $-CH_2-\overset{+}{N}(CH_3)$⟨piperazine⟩$\overset{+}{N}-Me_2$ X$^-$ |
| Br | CH$_3$ | Absent | $-CH_2-\overset{+}{N}(CH_3)$⟨piperazine⟩$\overset{+}{N}-Me_2$ X$^-$ |
| SMe | H | Absent | $-CH_2-\overset{+}{N}(CH_3)$⟨piperazine⟩$\overset{+}{N}-Me_2$ X$^-$ |
| SMe | CH$_3$ | Absent | $-CH_2-\overset{+}{N}(CH_3)$⟨piperazine⟩$\overset{+}{N}-Me_2$ X$^-$ |
| SO$_2$Me | H | Absent | $-CH_2-\overset{+}{N}(CH_3)$⟨piperazine⟩$\overset{+}{N}-Me_2$ X$^-$ |
| SO$_2$Me | CH$_3$ | Absent | $-CH_2-\overset{+}{N}(CH_3)$⟨piperazine⟩$\overset{+}{N}-Me_2$ X$^-$ |
| CONH$_2$ | H | Absent | $-CH_2-\overset{+}{N}(CH_3)$⟨piperazine⟩$\overset{+}{N}-Me_2$ X$^-$ |
| CONH$_2$ | CH$_3$ | Absent | $-CH_2-\overset{+}{N}(CH_3)$⟨piperazine⟩$\overset{+}{N}-Me_2$ X$^-$ |

TABLE 4-continued

[Structure diagram showing a molecule with labeled positions. $R^{a3}$ represents H]

| $R^{a1}$ | $R^3$ | $R^Y$ | $R^{a2}$ |
|---|---|---|---|
| CN | H | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| CN | $CH_3$ | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| Br | H | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| Br | $CH_3$ | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| SMe | H | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| SMe | $CH_3$ | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| $SO_2Me$ | H | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| $SO_2Me$ | $CH_3$ | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| $CONH_2$ | H | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| $CONH_2$ | $CH_3$ | $CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| CN | H | $CH_2CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| CN | $CH_3$ | $CH_2CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| Br | H | $CH_2CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |
| Br | $CH_3$ | $CH_2CH_3$ | $-CH_2-\overset{+}{N}{\underset{\diagdown\!\!=\!\!\diagup}{\diagup\!\!=\!\!\diagdown}}N-CH_2CH_2CONH_2 \quad X^-$ |

TABLE 4-continued

[Structure: beta-lactam fused to pyrroline with CO2- and phenyl group bearing substituents at positions 1-6, with R^a3 at 6, N⊕-R^y at 7, =CR^a2 at 8, N-R^3 on ring, R^a1 at position 2]

R^a3 represents H

| R^a1 | R^3 | R^Y | R^a2 |
|---|---|---|---|
| SMe | H | CH$_2$CH$_3$ | $-CH_2\overset{+}{\text{-}N}$(imidazole)$N-CH_2CH_2CONH_2$  X$^-$ |
| SMe | CH$_3$ | CH$_2$CH$_3$ | $-CH_2\overset{+}{\text{-}N}$(imidazole)$N-CH_2CH_2CONH_2$  X$^-$ |
| SO$_2$Me | H | CH$_2$CH$_3$ | $-CH_2\overset{+}{\text{-}N}$(imidazole)$N-CH_2CH_2CONH_2$  X$^-$ |
| SO$_2$Me | CH$_3$ | CH$_2$CH$_3$ | $-CH_2\overset{+}{\text{-}N}$(imidazole)$N-CH_2CH_2CONH_2$  X$^-$ |
| CONH$_2$ | H | CH$_2$CH$_3$ | $-CH_2\overset{+}{\text{-}N}$(imidazole)$N-CH_2CH_2CONH_2$  X$^-$ |
| CONH$_2$ | CH$_3$ | CH$_2$CH$_3$ | $-CH_2\overset{+}{\text{-}N}$(imidazole)$N-CH_2CH_2CONH_2$  X$^-$ | wherein X$^-$ represents a suitable counterion, R represents H or CH$_3$ and when R$^y$ is absent, the N atom to which R$^y$ is drawn attached is non-quaternary.

22. A compound having the structure set forth in Table 5 below:

TABLE 5

[Structure similar to above, indole-fused system]

R^a2 represents H

| R^a1 | R^3 | R^Y | R^a3 |
|---|---|---|---|
| CN | H | Absent | $-CH_2-\overset{+}{N}$(DABCO)$\overset{+}{N}-CH_2CONH_2$ X$^-$ |
| CN | CH$_3$ | Absent | $-CH_2-\overset{+}{N}$(DABCO)$\overset{+}{N}-CH_2CONH_2$ X$^-$ |

TABLE 5-continued

[Structure: core bicyclic β-lactam with (1-hydroxyethyl) group, linked to a substituted phenyl ring (positions 1-4 with $R^{a1}$ at position 1, $NR^3$ at position adjacent), which bears a dienyl-ammonium side chain with positions 5, 6, 7, 8; $R^{a3}$ at position 6, $R^y$ on $N^+$ (position 7), $R^{a2}$ at position 8. $R^{a2}$ represents H]

| $R^{a1}$ | $R^3$ | $R^Y$ | $R^{a3}$ |
|---|---|---|---|
| Br | H | Absent | $-CH_2-\overset{+}{N}\smalltriangle\overset{+}{N}-CH_2CONH_2\ X^-$ (piperazinium) |
| Br | $CH_3$ | Absent | $-CH_2-\overset{+}{N}\smalltriangle\overset{+}{N}-CH_2CONH_2\ X^-$ |
| $SCH_3$ | H | Absent | $-CH_2-\overset{+}{N}\smalltriangle\overset{+}{N}-CH_2CONH_2\ X^-$ |
| $SCH_3$ | $CH_3$ | Absent | $-CH_2-\overset{+}{N}\smalltriangle\overset{+}{N}-CH_2CONH_2\ X^-$ |
| $SO_2CH_3$ | H | Absent | $-CH_2-\overset{+}{N}\smalltriangle\overset{+}{N}-CH_2CONH_2\ X^-$ |
| $SO_2CH_3$ | $CH_3$ | Absent | $-CH_2-\overset{+}{N}\smalltriangle\overset{+}{N}-CH_2CONH_2\ X^-$ |
| $CONH_2$ | H | Absent | $-CH_2-\overset{+}{N}\smalltriangle\overset{+}{N}-CH_2CONH_2\ X^-$ |
| $CONH_2$ | $CH_3$ | Absent | $-CH_2-\overset{+}{N}\smalltriangle\overset{+}{N}-CH_2CONH_2\ X^-$ |
| CN | H | $CH_3$ | $-CH_2\text{-}\overset{+}{N}\smalltriangle N-CH_3\ X^-$ (imidazolium) |
| CN | $CH_3$ | $CH_3$ | $-CH_2\text{-}\overset{+}{N}\smalltriangle N-CH_3\ X^-$ |
| Br | H | $CH_3$ | $-CH_2\text{-}\overset{+}{N}\smalltriangle N-CH_3\ X^-$ |
| Br | $CH_3$ | $CH_3$ | $-CH_2\text{-}\overset{+}{N}\smalltriangle N-CH_3\ X^-$ |
| SMe | H | $CH_3$ | $-CH_2\text{-}\overset{+}{N}\smalltriangle N-CH_3\ X^-$ |

TABLE 5-continued

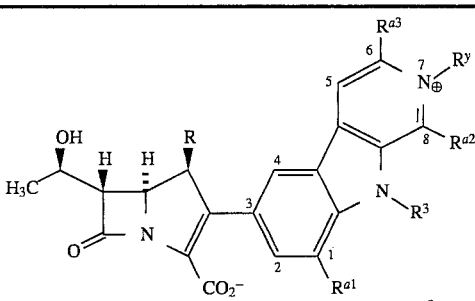

$R^{a2}$ represents H

| $R^{a1}$ | $R^3$ | $R^Y$ | $R^{a3}$ |
|---|---|---|---|
| SMe | CH₃ | CH₃ | —CH₂-N⁺=CH-CH=CH-N—CH₃ X⁻ (imidazolium) |
| SO₂CH₃ | H | CH₃ | —CH₂-N⁺=CH-CH=CH-N—CH₃ X⁻ |
| SO₂CH₃ | CH₃ | CH₃ | —CH₂-N⁺=CH-CH=CH-N—CH₃ X⁻ |
| CONH₂ | H | CH₃ | —CH₂-N⁺=CH-CH=CH-N—CH₃ X⁻ |
| CONH₂ | CH₃ | CH₃ | —CH₂-N⁺=CH-CH=CH-N—CH₃ X⁻ |
| CN | H | Absent | —CH₂—N⁺(CH₃)(—CH₂CH₂—)N⁺—Me₂ X⁻ |
| CN | CH₃ | Absent | —CH₂—N⁺(CH₃)(—CH₂CH₂—)N⁺—Me₂ X⁻ |
| Br | H | Absent | —CH₂—N⁺(CH₃)(—CH₂CH₂—)N⁺—Me₂ X⁻ |
| Br | CH₃ | Absent | —CH₂—N⁺(CH₃)(—CH₂CH₂—)N⁺—Me₂ X⁻ |
| SMe | H | Absent | —CH₂—N⁺(CH₃)(—CH₂CH₂—)N⁺—Me₂ X⁻ |
| SMe | CH₃ | Absent | —CH₂—N⁺(CH₃)(—CH₂CH₂—)N⁺—Me₂ X⁻ |
| SO₂Me | H | Absent | —CH₂—N⁺(CH₃)(—CH₂CH₂—)N⁺—Me₂ X⁻ |

TABLE 5-continued
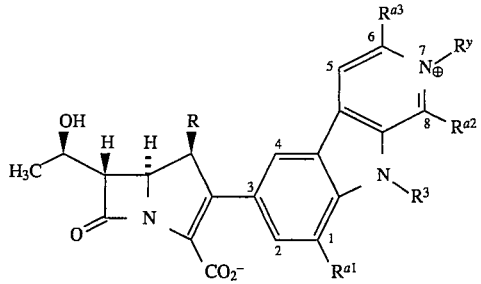
$R^{a2}$ represents H
| $R^{a1}$ | $R^3$ | $R^Y$ | $R^{a3}$ |
|---|---|---|---|
| SO$_2$Me | CH$_3$ | Absent | 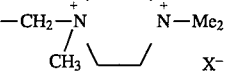 |
| CONH$_2$ | H | Absent | 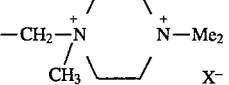 |
| CONH$_2$ | CH$_3$ | Absent |  |
| CN | H | CH$_3$ | 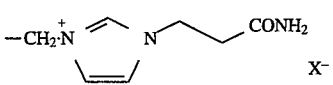 |
| CN | CH$_3$ | CH$_3$ | 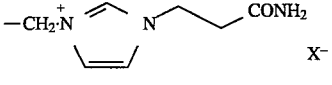 |
| Br | H | CH$_3$ | 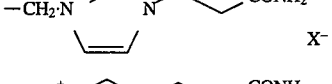 |
| Br | CH$_3$ | CH$_3$ | 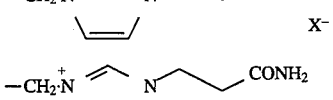 |
| SMe | H | CH$_3$ | 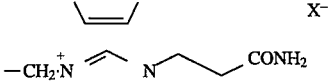 |
| SMe | CH$_3$ | CH$_3$ | 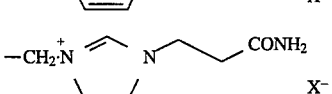 |
| SO$_2$Me | H | CH$_3$ | 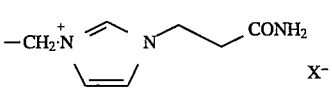 |
| SO$_2$Me | CH$_3$ | CH$_3$ | 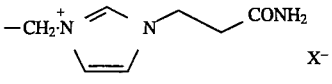 |
| CONH$_2$ | H | CH$_3$ | 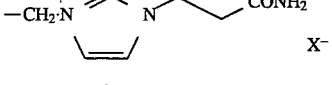 |
| CONH$_2$ | CH$_3$ | CH$_3$ | 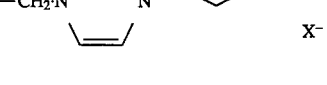 |
| CN | H | CH$_2$CH$_3$ |  |

TABLE 5-continued

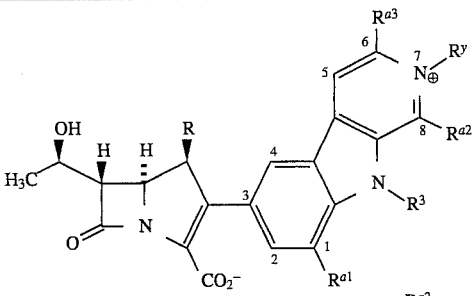

$R^{a2}$ represents H

| $R^{a1}$ | $R^3$ | $R^Y$ | $R^{a3}$ |
|---|---|---|---|
| CN | $CH_3$ | $CH_2CH_3$ | $-CH_2\text{-}\overset{+}{N}\underset{\underline{\phantom{xx}}}{\diagup\!\!\diagdown}N\frown CONH_2 \quad X^-$ |
| Br | H | $CH_2CH_3$ | $-CH_2\text{-}\overset{+}{N}\underset{\underline{\phantom{xx}}}{\diagup\!\!\diagdown}N\frown CONH_2 \quad X^-$ |
| Br | $CH_3$ | $CH_2CH_3$ | $-CH_2\text{-}\overset{+}{N}\underset{\underline{\phantom{xx}}}{\diagup\!\!\diagdown}N\frown CONH_2 \quad X^-$ |
| SMe | H | $CH_2CH_3$ | $-CH_2\text{-}\overset{+}{N}\underset{\underline{\phantom{xx}}}{\diagup\!\!\diagdown}N\frown CONH_2 \quad X^-$ |
| SMe | $CH_3$ | $CH_2CH_3$ | $-CH_2\text{-}\overset{+}{N}\underset{\underline{\phantom{xx}}}{\diagup\!\!\diagdown}N\frown CONH_2 \quad X^-$ |
| $SO_2Me$ | H | $CH_2CH_3$ | $-CH_2\text{-}\overset{+}{N}\underset{\underline{\phantom{xx}}}{\diagup\!\!\diagdown}N\frown CONH_2 \quad X^-$ |
| $SO_2Me$ | $CH_3$ | $CH_2CH_3$ | $-CH_2\text{-}\overset{+}{N}\underset{\underline{\phantom{xx}}}{\diagup\!\!\diagdown}N\frown CONH_2 \quad X^-$ |
| $CONH_2$ | H | $CH_2CH_3$ | $-CH_2\text{-}\overset{+}{N}\underset{\underline{\phantom{xx}}}{\diagup\!\!\diagdown}N\frown CONH_2 \quad X^-$ |
| $CONH_2$ | $CH_3$ | $CH_2CH_3$ | $-CH_2\text{-}\overset{+}{N}\underset{\underline{\phantom{xx}}}{\diagup\!\!\diagdown}N\frown CONH_2 \quad X^-$ | wherein $X^-$ is a suitable counterion, R represents H or $CH_3$ and when $R^y$ is absent, N atom to which $R^y$ is shown attached is non-quaternary.

23. A pharmaceutical composition comprised of a compound in accordance with claim 1 in combination with a pharmaceutically acceptable carrier.

24. A method of treating a bacterial infection in a mammalian patient in need of such treatment comprising administering to said mammal a compound in accordance with claim 1 in an amount which is effective to treat said bacterial infection.

* * * * *

UNITED STATES PATENT AND TRADEMARK OFFICE
CERTIFICATE OF CORRECTION

PATENT NO. : 5,532,261
DATED : July 2, 1996
INVENTOR(S) : DiNinno et al.

It is certified that error appears in the above-indentified patent and that said Letters Patent is hereby corrected as shown below:

In Claim 1, column 94, at line 3:
        After "-H", replace [—O—] with  -O⁻ .

Signed and Sealed this

Eighteenth Day of February, 1997

Attest:

BRUCE LEHMAN

*Attesting Officer*      *Commissioner of Patents and Trademarks*